US007371517B2

(12) United States Patent
Evans et al.

(10) Patent No.: US 7,371,517 B2
(45) Date of Patent: May 13, 2008

(54) HIGH PURITY X-CHROMOSOME BEARING AND Y-CHROMOSOME BEARING POPULATIONS OF SPERMATOZOA

(75) Inventors: Kenneth M. Evans, Fort Collins, CO (US); Erik B. van Munster, Amsterdam (NL)

(73) Assignee: XY, Inc., Fort Collins, CO (US)

( * ) Notice: Subject to any disclaimer, the term of this patent is extended or adjusted under 35 U.S.C. 154(b) by 263 days.

(21) Appl. No.: 10/275,770

(22) PCT Filed: May 9, 2001

(86) PCT No.: PCT/US01/15150

§ 371 (c)(1),
(2), (4) Date: Feb. 7, 2003

(87) PCT Pub. No.: WO01/85913

PCT Pub. Date: Nov. 15, 2001

(65) Prior Publication Data

US 2004/0053243 A1 Mar. 18, 2004

Related U.S. Application Data

(60) Provisional application No. 60/267,571, filed on Feb. 10, 2001, provisional application No. 60/239,752, filed on Oct. 12, 2000, provisional application No. 60/203,089, filed on May 9, 2000.

(51) Int. Cl.
*C12Q 1/68* (2006.01)
(52) U.S. Cl. ........................................................ 435/6
(58) Field of Classification Search ...................... 435/2
See application file for complete search history.

(56) References Cited

U.S. PATENT DOCUMENTS

| | | | |
|---|---|---|---|
| 3,299,354 A | 1/1967 | Hogg | |
| 3,499,435 A | 3/1970 | Rockwell et al. | |
| 3,547,526 A | 12/1970 | Devereux | |
| 3,644,128 A | 2/1972 | Lipner | |
| 3,661,460 A | 5/1972 | Elking et al. | |
| 3,687,806 A | 8/1972 | Van den Bovenkamp | 195/1.3 |
| 3,710,933 A | 1/1973 | Fulwyler et al. | |
| 3,756,459 A | 9/1973 | Bannister | |
| 3,761,941 A | 9/1973 | Robertson | |
| 3,810,010 A | 5/1974 | Thom | |
| 3,826,364 A | 7/1974 | Bonner et al. | |
| 3,829,216 A | 8/1974 | Persidsky | 356/36 |
| 3,833,796 A | 9/1974 | Fetner et al. | |
| 3,877,430 A | 4/1975 | Wieder | |
| 3,893,766 A | 7/1975 | Hogg | |
| 3,894,529 A | 7/1975 | Shrimpton | 128/1 R |
| 3,909,744 A | 9/1975 | Wisner et al. | |
| 3,947,093 A | 3/1976 | Goshima et al. | |
| 3,960,449 A | 6/1976 | Carleton et al. | |
| 3,963,606 A | 6/1976 | Hogg | |
| 3,973,003 A | 8/1976 | Colas | |
| 3,973,196 A | 8/1976 | Hogg | |
| 4,007,087 A | 2/1977 | Ericsson | |
| 4,009,260 A | 2/1977 | Ericsson | 424/105 |
| 4,014,611 A | 3/1977 | Simpson et al. | |
| 4,067,965 A | 1/1978 | Bhattacharya | 424/105 |
| 4,070,617 A | 1/1978 | Kachel et al. | |
| 4,083,957 A | 4/1978 | Lang | 424/78 |
| 4,085,205 A | 4/1978 | Hancock | 424/105 |
| 4,092,229 A | 5/1978 | Bhattacharya | 204/180 R |
| 4,155,831 A | 5/1979 | Bhattacharya | 207/299 R |
| 4,162,282 A | 7/1979 | Fulwyler et al. | |
| 4,178,936 A | 12/1979 | Newcomb | |
| 4,179,218 A | 12/1979 | Erdmann et al. | |
| 4,191,749 A | 3/1980 | Bryant | 424/105 |
| 4,200,802 A | 4/1980 | Satzman et al. | |
| 4,225,405 A | 9/1980 | Lawson | 204/180 R |
| 4,230,558 A | 10/1980 | Fulwyler | |
| 4,255,021 A | 3/1981 | Brunsden | |
| 4,267,268 A | 5/1981 | Nelson, Jr. | |
| 4,274,408 A | 6/1981 | Nimrod | |
| 4,274,740 A | 6/1981 | Eidenschink et al. | |
| 4,276,139 A | 6/1981 | Lawson | 204/180 R |
| 4,302,166 A | 11/1981 | Fulwyler et al. | |
| 4,317,520 A | 3/1982 | Lombardo et al. | |
| 4,318,480 A | 3/1982 | Lombardo et al. | |

(Continued)

FOREIGN PATENT DOCUMENTS

BR        9704313      6/1999

(Continued)

OTHER PUBLICATIONS

Cran DG and Johnson LA (1996) The predetermination of embryonic sex using flow cytometrically separated X and Y spermatozoa Human Reproduction Update 2: 355-363.*

(Continued)

*Primary Examiner*—Robert B. Mondesi
*Assistant Examiner*—Amanda P. Wood
(74) *Attorney, Agent, or Firm*—Santangelo Law Offices, P.C.

(57) ABSTRACT

Isolated non-naturally occurring populations of spermatozoa (15) having high purity and technologies to differentiate spermatozoa (28) based on characteristics such as mass, volume, orientation, or emitted light including methods of analysis and apparatus such as beam shaping optics (30) and detectors (32).

22 Claims, 28 Drawing Sheets

U.S. PATENT DOCUMENTS

| | | | |
|---|---|---|---|
| 4,318,481 A | 3/1982 | Lombardo et al. | |
| 4,318,482 A | 3/1982 | Barry et al. | |
| 4,325,483 A | 4/1982 | Lombardo et al. | |
| 4,327,177 A | 4/1982 | Shrimpton | |
| 4,339,434 A | 7/1982 | Ericsson | 424/105 |
| 4,341,471 A | 7/1982 | Hogg et al. | |
| 4,350,410 A | 9/1982 | Minott | |
| 4,352,558 A | 10/1982 | Eisert | |
| 4,361,400 A | 11/1982 | Gray et al. | |
| 4,362,246 A | 12/1982 | Adair | 209/3.3 |
| 4,395,397 A | 7/1983 | Shapiro | |
| 4,395,676 A | 7/1983 | Hollinger et al. | |
| 4,400,764 A | 8/1983 | Kenyon | |
| 4,422,761 A | 12/1983 | Frommer | |
| 4,448,767 A | 5/1984 | Bryant | 424/85 |
| 4,474,875 A | 10/1984 | Shrimpton | 435/2 |
| 4,487,320 A | 12/1984 | Auer | |
| 4,501,366 A | 2/1985 | Thompson | 209/556 |
| 4,511,661 A | 4/1985 | Goldberg | 436/503 |
| 4,515,274 A | 5/1985 | Hollinger et al. | |
| 4,523,809 A | 6/1985 | Toboada et al. | |
| 4,538,733 A | 9/1985 | Hoffman | |
| 4,559,309 A | 12/1985 | Evenson | |
| 4,573,796 A | 3/1986 | Martin | |
| 4,598,408 A | 7/1986 | O'Keefe | |
| 4,600,302 A | 7/1986 | Sage, Jr. | |
| 4,605,558 A | 8/1986 | Shrimpton | 424/561 |
| 4,631,483 A | 12/1986 | Proni et al. | |
| 4,637,691 A | 1/1987 | Uehara et al. | |
| RE32,350 E | 2/1987 | Bhattacharya | 204/180.1 |
| 4,654,025 A | 3/1987 | Cassou et al. | |
| 4,660,971 A | 4/1987 | Sage et al. | 356/39 |
| 4,673,288 A | 6/1987 | Thomas et al. | |
| 4,680,258 A | 7/1987 | Hammerling et al. | 435/7 |
| 4,683,195 A | 7/1987 | Mullis et al. | |
| 4,683,202 A | 7/1987 | Mullis | |
| 4,691,829 A | 9/1987 | Auer | |
| 4,698,142 A | 10/1987 | Muroi et al. | 204/182.3 |
| 4,702,598 A | 10/1987 | Böhmer | |
| 4,714,680 A | 12/1987 | Civin | |
| 4,744,090 A | 5/1988 | Freiberg | |
| 4,749,458 A | 6/1988 | Muroi et al. | 204/182.3 |
| 4,756,427 A | 7/1988 | Gohde et al. | |
| 4,758,729 A | 7/1988 | Monnin | |
| 4,764,013 A * | 8/1988 | Johnston | 356/484 |
| 4,780,451 A | 10/1988 | Donaldson | |
| 4,790,653 A | 12/1988 | North, Jr. | |
| 4,794,086 A | 12/1988 | Kasper et al. | |
| 4,796,788 A | 1/1989 | Bond | |
| 4,818,103 A | 4/1989 | Thomas et al. | |
| 4,831,385 A | 5/1989 | Archer et al. | |
| 4,836,038 A | 6/1989 | Baldwyn | |
| 4,845,025 A | 7/1989 | Lary et al. | |
| 4,846,785 A | 7/1989 | Cassou | |
| 4,877,965 A | 10/1989 | Dandliker et al. | |
| 4,942,305 A | 7/1990 | Sommer | |
| 4,959,354 A | 9/1990 | Barbetti | |
| 4,965,204 A | 10/1990 | Civin | |
| 4,979,093 A | 12/1990 | Laine et al. | |
| 4,980,277 A | 12/1990 | Junilla | |
| 4,981,580 A | 1/1991 | Auer | |
| 4,983,038 A | 1/1991 | Ohki et al. | |
| 4,987,539 A | 1/1991 | Moore et al. | |
| 4,988,619 A | 1/1991 | Pinkel | 435/30 |
| 4,999,283 A | 3/1991 | Zavos et al. | 435/2 |
| 5,005,981 A | 4/1991 | Schulte et al. | |
| 5,007,732 A | 4/1991 | Ohki et al. | |
| 5,017,497 A | 5/1991 | De Grooth | |
| 5,021,244 A | 6/1991 | Spaulding | 424/561 |
| 5,030,002 A | 7/1991 | North, Jr. | |
| 5,034,613 A | 7/1991 | Denk et al. | |
| 5,055,393 A | 10/1991 | Kwoh et al. | |
| 5,079,959 A | 1/1992 | Miyake et al. | |
| 5,084,004 A | 1/1992 | Ranoux | |
| 5,088,816 A | 2/1992 | Tomioka et al. | |
| 5,098,657 A | 3/1992 | Blackford et al. | |
| 5,101,978 A | 4/1992 | Marcus | |
| 5,127,729 A | 7/1992 | Oetliker et al. | |
| 5,132,548 A | 7/1992 | Borden et al. | |
| 5,135,759 A | 8/1992 | Johnson | 424/561 |
| 5,144,224 A | 9/1992 | Larsen | |
| 5,150,313 A | 9/1992 | Van den Engh et al. | |
| 5,159,397 A | 10/1992 | Kosaka et al. | |
| 5,159,403 A | 10/1992 | Kosaka | |
| 5,162,306 A | 11/1992 | Donaldson | |
| 5,167,926 A | 12/1992 | Kimura et al. | |
| 5,180,065 A | 1/1993 | Touge et al. | |
| 5,182,617 A | 1/1993 | Yoneyama et al. | |
| 5,195,979 A | 3/1993 | Schinkel et al. | |
| 5,199,576 A | 4/1993 | Corio et al. | |
| 5,215,376 A | 6/1993 | Schulte et al. | |
| 5,219,729 A | 6/1993 | Hodgen | |
| 5,247,339 A | 9/1993 | Ogino | |
| 5,259,593 A | 11/1993 | Orme et al. | |
| 5,260,764 A | 11/1993 | Fukuda et al. | |
| 5,298,967 A | 3/1994 | Wells | |
| 5,315,122 A * | 5/1994 | Pinsky et al. | 250/461.2 |
| 5,316,540 A | 5/1994 | McMannis et al. | |
| 5,346,990 A | 9/1994 | Spaulding | 530/350 |
| 5,359,907 A | 11/1994 | Baker et al. | |
| 5,366,888 A | 11/1994 | Fry et al. | |
| 5,367,474 A | 11/1994 | Auer et al. | |
| 5,370,842 A | 12/1994 | Miyazaki et al. | |
| 5,371,585 A | 12/1994 | Morgan et al. | 356/246 |
| 5,412,466 A | 5/1995 | Ogino | |
| 5,437,987 A | 8/1995 | Ten et al. | |
| 5,439,362 A | 8/1995 | Spaulding | 424/185.1 |
| 5,447,842 A | 9/1995 | Simons | |
| 5,452,054 A | 9/1995 | Dewa et al. | |
| 5,461,145 A | 10/1995 | Kudo et al. | |
| 5,466,572 A | 11/1995 | Sasaki et al. | 435/2 |
| 5,467,189 A | 11/1995 | Kreikebaum et al. | |
| 5,471,294 A | 11/1995 | Ogino | |
| 5,471,299 A | 11/1995 | Kaye et al. | |
| 5,480,774 A | 1/1996 | Hew et al. | |
| 5,483,469 A | 1/1996 | Van den Engh et al. | 364/555 |
| 5,492,534 A | 2/1996 | Atheyde | |
| 5,494,795 A | 2/1996 | Guerry et al. | |
| 5,496,272 A | 3/1996 | Chung et al. | |
| 5,503,994 A | 4/1996 | Shear et al. | 436/90 |
| 5,514,537 A | 5/1996 | Chandler | 435/2 |
| 5,523,573 A | 6/1996 | Hanninen et al. | |
| 5,532,155 A | 7/1996 | Ranoux | |
| 5,558,998 A | 9/1996 | Hammond et al. | |
| 5,559,032 A | 9/1996 | Pomeroy et al. | |
| 5,578,449 A | 11/1996 | Fr asch et al. | |
| 5,589,457 A | 12/1996 | Wiltbank | 514/12 |
| 5,596,401 A | 1/1997 | Kusuzawa | |
| 5,601,235 A | 2/1997 | Booker et al. | |
| 5,601,533 A | 2/1997 | Hancke et al. | |
| 5,602,039 A | 2/1997 | Van den Engh | 436/164 |
| 5,602,349 A | 2/1997 | Van den Engh | 73/864.85 |
| 5,622,820 A | 4/1997 | Rossi | |
| 5,641,457 A | 6/1997 | Vardanega | |
| 5,643,796 A | 7/1997 | Van Den Engh et al. | |
| 5,650,847 A | 7/1997 | Maltsev et al. | |
| 5,660,997 A | 8/1997 | Spaulding | 435/7.21 |
| 5,663,048 A | 9/1997 | Winkfein et al. | |
| 5,665,315 A | 9/1997 | Robert et al. | |
| 5,672,880 A | 9/1997 | Kain | |
| 5,675,401 A | 10/1997 | Wangler et al. | |
| 5,684,575 A | 11/1997 | Steen | |
| 5,687,727 A | 11/1997 | Kraus et al. | |
| 5,690,815 A | 11/1997 | Krasnoff et al. | |

| | | | | | | |
|---|---|---|---|---|---|---|
| 5,690,895 | A | 11/1997 | Matsumoto et al. ........... 422/73 | 6,667,830 | B1 | 12/2003 | Iketaki et al. |
| 5,691,133 | A | 11/1997 | Critser et al. | 6,671,044 | B2 | 12/2003 | Ortyn et al. |
| 5,693,534 | A | 12/1997 | Alak et al. | 6,673,095 | B2 | 1/2004 | Nordquist |
| 5,700,692 | A | 12/1997 | Sweet .......................... 436/50 | 6,698,627 | B2 | 3/2004 | Garcia et al. |
| 5,707,808 | A | 1/1998 | Roslaniec et al. | 6,704,313 | B1 | 3/2004 | De Resende et al. |
| 5,708,868 | A | 1/1998 | Ishikawa | 6,729,369 | B2 | 5/2004 | Neas et al. |
| 5,726,364 | A | 3/1998 | Van den Engh ......... 73/864.85 | 6,752,298 | B2 | 6/2004 | Garcia et al. |
| 5,759,767 | A | 6/1998 | Lakowicz et al. | 6,761,286 | B2 | 7/2004 | Py et al. |
| 5,777,732 | A | 7/1998 | Hanninen et al. | 6,761,288 | B2 | 7/2004 | Garcia |
| 5,780,230 | A | 7/1998 | Li et al. | 6,782,768 | B2 | 8/2004 | Buchanan et al. |
| 5,786,560 | A | 7/1998 | Tatah et al. | 6,789,706 | B2 | 9/2004 | Abergel et al. |
| 5,793,485 | A | 8/1998 | Gourley | 6,789,759 | B2 | 9/2004 | Heldt |
| 5,796,112 | A | 8/1998 | Ichie | 6,793,387 | B1 | 9/2004 | Neas et al. |
| 5,799,830 | A | 9/1998 | Carroll et al. | 6,819,411 | B1 | 11/2004 | Sharpe et al. |
| 5,804,436 | A | 9/1998 | Okun et al. | 7,094,527 | B2 | 8/2006 | Seidel et al. |
| 5,815,262 | A | 9/1998 | Schrof et al. | 7,105,355 | B2 | 9/2006 | Kurabayashi et al. |
| 5,819,948 | A | 10/1998 | Van den Engh ............ 209/158 | 7,195,920 | B2 | 3/2007 | Seidel et al. |
| 5,824,269 | A | 10/1998 | Kosaka et al. | 7,208,265 | B1 | 4/2007 | Schenk |
| 5,835,262 | A | 11/1998 | Iketaki et al. | 7,221,453 | B2 | 5/2007 | Sharpe et al. |
| 5,868,767 | A | 2/1999 | Farley et al. | 2002/0096123 | A1 | 7/2002 | Whittier et al. |
| 5,873,254 | A | 2/1999 | Arav | 2002/0113965 | A1 | 8/2002 | Roche et al. |
| 5,876,942 | A | 3/1999 | Cheng et al. | 2002/0119558 | A1 | 8/2002 | Seidel et al. |
| 5,880,457 | A | 3/1999 | Tomiyama et al. ......... 250/207 | 2002/0131957 | A1 | 9/2002 | Gavin |
| 5,888,730 | A | 3/1999 | Gray et al. | 2002/0141902 | A1 | 10/2002 | Ozasa et al. |
| 5,891,734 | A * | 4/1999 | Gill et al. ..................... 436/43 | 2002/0186375 | A1 | 12/2002 | Asbury et al. |
| 5,893,843 | A | 4/1999 | Rodrigues Claro | 2003/0002027 | A1 | 1/2003 | Fritz |
| 5,895,764 | A | 4/1999 | Sklar et al. | 2003/0098421 | A1 | 5/2003 | Ho |
| 5,895,922 | A | 4/1999 | Ho | 2003/0129091 | A1 | 7/2003 | Seidel et al. |
| 5,899,848 | A | 5/1999 | Haubrich | 2003/0157475 | A1 | 8/2003 | Schenk |
| 5,912,257 | A | 6/1999 | Prasad et al. | 2003/0207461 | A1 | 11/2003 | Bell et al. |
| 5,916,144 | A | 6/1999 | Prather et al. | 2003/0209059 | A1 | 11/2003 | Kawano |
| 5,916,449 | A | 6/1999 | Ellwart et al. | 2004/0005582 | A1 | 1/2004 | Shipwast |
| 5,919,360 | A | 7/1999 | Contaxis, III et al. | 2004/0031071 | A1 | 2/2004 | Morris et al. |
| 5,919,621 | A | 7/1999 | Brown | 2004/0049801 | A1 | 3/2004 | Seidel |
| 5,934,885 | A | 8/1999 | Farrell et al. | 2004/0053243 | A1 | 3/2004 | Evans |
| 5,985,216 | A | 11/1999 | Rens et al. .................... 422/73 | 2004/0055030 | A1 | 3/2004 | Maxwell et al. |
| 5,985,538 | A | 11/1999 | Stachecju | 2004/0062685 | A1 | 4/2004 | Norton et al. |
| 6,002,471 | A | 12/1999 | Quake | 2004/0107150 | A1 | 6/2004 | Neas et al. |
| 6,050,935 | A | 4/2000 | Ranoux et al. | 2004/0132001 | A1 | 7/2004 | Seidel et al. |
| 6,071,689 | A | 6/2000 | Seidel et al. .................... 435/2 | 2005/0003472 | A1 | 1/2005 | Muhammad |
| 6,086,574 | A | 7/2000 | Carroll et al. | 2005/0011582 | A1 | 1/2005 | Haug |
| 6,087,352 | A | 7/2000 | Trout | 2005/0064383 | A1 | 3/2005 | Bashkin et al. |
| 6,117,068 | A | 9/2000 | Gourley et al. | 2005/0112541 | A1 | 5/2005 | Durack |
| 6,119,465 | A | 9/2000 | Mullens et al. | 2005/0214733 | A1 | 9/2005 | Graham |
| 6,133,044 | A | 10/2000 | Van den Engh | 2005/0244805 | A1 | 11/2005 | Ludwig et al. |
| 6,140,121 | A | 10/2000 | Ellington et al. | 2005/0282245 | A1 | 12/2005 | Ludwig et al. |
| 6,149,867 | A | 11/2000 | Seidel et al. | 2006/0118167 | A1 | 6/2006 | Neas et al. |
| 6,153,373 | A | 11/2000 | Benjamin et al. | 2006/0147894 | A1 | 7/2006 | Sowter |
| 6,154,276 | A | 11/2000 | Mariella, Jr. ................. 356/337 | 2006/0263829 | A1 | 11/2006 | Evans et al. |
| 6,175,409 | B1 | 1/2001 | Nielsen et al. | 2006/0281176 | A1 | 12/2006 | Seidel et al. |
| 6,177,277 | B1 | 1/2001 | Soini | 2007/0026378 | A1 | 2/2007 | Schenk |
| 6,238,920 | B1 | 5/2001 | Nagai et al. | 2007/0026379 | A1 | 2/2007 | Seidel et al. |
| 6,248,590 | B1 | 6/2001 | Malachowski | 2007/0042342 | A1 | 2/2007 | Seidel et al. |
| 6,263,745 | B1 | 7/2001 | Buchanan et al. | 2007/0092860 | A1 | 4/2007 | Schenk |
| 6,283,920 | B1 | 9/2001 | Eberle et al. | 2007/0099171 | A1 | 5/2007 | Schenk |
| 6,328,071 | B1 | 12/2001 | Austin | 2007/0099260 | A1 | 5/2007 | Seidel et al. |
| 6,357,307 | B2 | 3/2002 | Buchanan et al. | | | | |
| 6,372,422 | B1 | 4/2002 | Seidel et al. | | | FOREIGN PATENT DOCUMENTS | |
| 6,395,305 | B1 | 5/2002 | Buhr et al. | | | | |
| 6,411,835 | B1 | 6/2002 | Modell et al. | CN | | 03109426.0 | 12/2005 |
| 6,463,314 | B1 | 10/2002 | Haruna | DE | | 69028526 | 2/1997 |
| 6,489,092 | B1 | 12/2002 | Benjamin et al. | DE | | 195 49 015 C1 | 4/1997 |
| 6,495,366 | B1 | 12/2002 | Briggs | DE | | 198 82 943.3 | 2/2001 |
| 6,524,860 | B1 | 2/2003 | Seidel et al. | EP | | 0025296 A2 | 3/1981 |
| 6,528,802 | B1 | 3/2003 | Karsten et al. | EP | | 0071538 A1 | 2/1983 |
| 6,534,308 | B1 | 3/2003 | Palsson et al. | EP | | 0140616 | 5/1985 |
| 6,537,829 | B1 | 3/2003 | Zarling et al. | EP | | 0160201 A2 | 11/1985 |
| 6,577,387 | B2 | 6/2003 | Ross, III et al. | EP | | 0288029 B1 | 4/1986 |
| 6,590,911 | B1 | 7/2003 | Spinelli et al. | EP | | 0189702 A1 | 8/1986 |
| 6,604,435 | B2 | 8/2003 | Buchanan et al. | EP | | 0276166 A2 | 7/1988 |
| 6,617,107 | B1 | 9/2003 | Dean | EP | | A-0 366794 | 5/1990 |
| 6,618,679 | B2 | 9/2003 | Loehrlein et al. | EP | | 0461618 | 12/1991 |
| 6,642,018 | B1 | 11/2003 | Koller et al. | EP | | 0468100 A1 | 1/1992 |

| | | | |
|---|---|---|---|
| EP | 0570102 | A1 | 3/1993 |
| EP | 0538786 | A | 4/1993 |
| EP | 606847 | A2 | 7/1994 |
| EP | A-0 478155 | | 1/1998 |
| EP | 0781985 | A3 | 7/1998 |
| EP | 1250897 | A1 | 10/2002 |
| EP | 1403633 | A3 | 4/2004 |
| FR | 2574656 | A1 | 6/1986 |
| FR | A-2 635453 | | 2/1990 |
| FR | 2 647 668 | A | 12/1990 |
| FR | 2699678 | A1 | 6/1994 |
| GB | 1471019 | | 4/1977 |
| JP | 61139747 | A | 6/1986 |
| JP | 61159135 | A | 7/1986 |
| JP | 2024535 | | 1/1990 |
| JP | 4126064 | A | 4/1992 |
| JP | 4126065 | A | 4/1992 |
| JP | 4126066 | A | 4/1992 |
| JP | 4126079 | A | 4/1992 |
| JP | 4126080 | A | 4/1992 |
| JP | 4126081 | A | 4/1992 |
| SU | 1056008 | | 11/1983 |
| SU | 1260778 | A1 | 9/1986 |
| WO | WO 88/07198 | | 9/1988 |
| WO | WO 90/13315 | A1 | 11/1990 |
| WO | 91/05236 | | 4/1991 |
| WO | WO 93/17322 | A1 | 9/1993 |
| WO | WO 96/12171 | | 10/1995 |
| WO | WO 96/31764 | | 10/1996 |
| WO | WO 98/34094 | | 6/1998 |
| WO | WO 99/05504 | | 7/1998 |
| WO | WO 98/48259 | | 10/1998 |
| WO | WO 99/38883 | | 5/1999 |
| WO | WO 99/33956 | | 8/1999 |
| WO | WO 99/42810 | | 8/1999 |
| WO | WO 99/44037 | A1 | 9/1999 |
| WO | WO 00/06193 | | 10/2000 |
| WO | WO 0129538 | | 4/2001 |
| WO | WO 01/37655 | A1 | 5/2001 |
| WO | WO 01/40765 | A2 | 6/2001 |
| WO | WO 01/40765 | A3 | 6/2001 |
| WO | WO 01/51612 | A1 | 7/2001 |
| WO | 0241906 | A2 | 11/2001 |
| WO | WO 01/85913 | A2 | 11/2001 |
| WO | WO 01/85913 | A3 | 11/2001 |
| WO | WO 01/90295 | A1 | 11/2001 |
| WO | WO 01/95815 | A1 | 12/2001 |
| WO | WO 02/19943 | A1 | 3/2002 |
| WO | WO 02/28311 | A2 | 4/2002 |
| WO | WO 02/41906 | A2 | 5/2002 |
| WO | WO 02/43486 | A1 | 6/2002 |
| WO | WO 02/43574 | A2 | 6/2002 |
| WO | 03020877 | A2 | 8/2002 |
| WO | WO 2004/009237 | A1 | 1/2004 |
| WO | WO 2004/009237 | A3 | 1/2004 |
| WO | WO 2004/012837 | A1 | 2/2004 |
| WO | WO 2004/012837 | A3 | 2/2004 |
| WO | WO 2004/017041 | A2 | 2/2004 |
| WO | WO 2004/017041 | A3 | 2/2004 |
| WO | WO 2004/024227 | A2 | 3/2004 |
| WO | WO 2004/059282 | A2 | 7/2004 |
| WO | WO 2004/003697 | A2 | 10/2004 |
| WO | WO 2004/087177 | A1 | 10/2004 |
| WO | WO 2004/088283 | A2 | 10/2004 |
| WO | WO 2004/104178 | A2 | 12/2004 |
| WO | WO 2004/104178 | A3 | 12/2004 |
| WO | WO 2005/094852 | A2 | 10/2005 |
| WO | WO 2005/095590 | A2 | 10/2005 |
| WO | WO 2005/095960 | A1 | 10/2005 |
| WO | WO 2006012597 | A2 | 2/2006 |
| WO | 2006060770 | A2 | 8/2006 |
| WO | 2007/016090 | A2 | 2/2007 |

OTHER PUBLICATIONS

Hamamatsu Photomultiplier Tubes (Dec. 1997) TMPO 0003E01 pp. 4, 28, 70.*
Johnson LA, Welch GR, Rens W (1999) The Beltsville Sperm Sexing Technology: High-Speed Sperm Sorting Gives Improved Sperm Output for In Vitro Fertilization and AI J. Anim. Sci. 77, (Suppl 2) 213-220.*
Peters D, Branscomb E, Dean P, Merrill T, Pinkel D, Van Dilla M, Gray JW (1985) The LLNL High-Speed Sorter: Design Features, Operational characteristics, and Biological Utility Cytometry 6: 290-301.*
Rens W, Welch GR, Houck DW, van Oven CH, Johnson LA Slit-Scan Flow Cytometry for Consistent High Resolution DNA Analysis of X- and Y-Chromosome Bearing Sperm Cytometry 25: 191-199 (1996).*
Schmid RL, Kato H, Herickhoff LA, Schenk JL, McCue PM, Chung YG, Squires EL (Jul. 1998) in Proceedings of 7th Int. Symp. on Equine Reprod. J Reprod. and Fertility, Suppl. 56: 519-525.*
van Munster EB (2002) Interferometry in Flow to Sort Unstained X-Y-Chromosome-Bearing Bull Spermatozoa Cytometry 47: 192-199.*
Amann, R.P. and Seidel, G.E. Jr., 1982. Prospects For Sexing Mammalian Sperm, Animal Reproduction Laboratory College of Veterinary Medicine and Biomedical Sciences, Colorado State University, Fort Collins, CO, 80523, 1982.
Baker, R.D., et al., H.W. 1968. Effect of volume of semen, number of sperm and drugs on transport of sperm in artificially inseminated gilts. J. Anim. Sci. 27:88-93.
Beyhan, Z., et al., "Sexual dimorphism in IVF bovine embryos produced by sperm sorted by high speed flow cytometry", Theriogenology 49(1):359. abstr. 1998.
Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.
Purdy, P.H. et al., Effect of Adding Cholesterol to Bull Sperm Membranes on Sperm Capacitation, the Acrosome Reaction, and Fertility, Biology of Reproduction 71, 522-527 (2004).
Purdy, P. H. et al., Effect of cholesterol-loaded cyclodextrin on the cryosurvival of bull sperm, Cryobiology 48 (2004) 36-45.
Moce E., et al., Cholesterol-loaded cyclodextrins added to fresh bull ejaculates improve sperm cryosurvival, J. Anim. Sci, 2006, 84:826-833.
Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.
Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.
Bavister, B.D. et al., The effects of Sperm Extracts and Energy Sources on the Motility and Acromosome Reaction of hamster Spermatozoa in vitero; Biology of Reporduction 16, 228-237 (1997).
Fattouh, El-S.M. et al., Effect of Caffine on the Post-Thaw Motility of Buffalo Spermatozoa; Theriogenology, Jul. 1991, vol. 36 No. 1.
Koh-ichi Hamano, et al., Gender Preselection in Cattle with Intracytoplasmically injected, flow cytometrically sorted sperm heads, Biology of Reproduction 60, 1194-1197 (1990).
Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.
Nikkei Biotech, Supplement, Latest Information of Biological Instruments and Reagents, 1988, pp. 93-94.
Parallel Korean Application No. 10-2002-7015074;Office Action dated Apr. 2, 2007.
Parallel European Regional Phase Application No. EP 01 93 7288; Search Report dated Jan. 18, 2007.

Parallel New Zealand Application No. 545311, Office Action dated Mar. 16, 2007.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Using of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926, Aug. 2002, vol. 85, No. 8.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E. Suppl.): E120-E130; 2004 American Dairy Science Assoc.

Arathy D.S., et al., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84:2413-2418, (2001).

Dransfield, M.B.G., et al., Timing of Inseminatio for Dairy Cows Identified in Estrus by a Radiotelemetric Etrus Detection System. 1998 J Dairy Sci. 81: 1874-1882.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination of Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times Al of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (*Anser anser* L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et al. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

IP Office of China—First Notification of Office Action; Appl. No. 01810748.6, dated Apr. 16, 2004; 4 pages.

IP Office of China—Second Notification of Office Action, Appl. No. 01810748.6; dated Mar. 11, 2005; 5 pages.

IP Office of New Zealand—Examination Report; Appl. No. 551401 dated Jul. 19, 2007; 3 pages.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Parallel Chinese Application No. 01810748.6, Office Action dated Oct. 19, 2007.

Parallel Korean Application No. 10-2002-7015074, Office Action dated Oct. 30, 2007.

Beyhan, Z., et al., "Sexual Dimorphism in IVF Bovine Embryos Produced by Sperm Sorted by High Speed Flow Cytometry", abstr. Therio. 49(1): 359 (1998).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilisation of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Autralian Patent Application No. 2001263039; Examination Report dated Jun. 24, 2005.

Indian Patent Application No. IN/PCT/2002/01393; First Examination Report dated Jan. 12, 2005.

New Zealand Patent Application No. 522613; Examination Report dated May 12, 2003.

New Zealand Patent Application No. 522613; Examination Report dated Oct. 28, 2004.

New Zealand Patent Application No. 522613; Examination Report dated Jun. 28, 2005.

New Zealand Patent Application No. 522613; Grant of Patent No. 522613 dated Dec. 30, 2005.

New Zealand Patent Application No. 535812; Examination Report dated Oct. 14, 2004.

Russian Patent Application No. 2002132899/13 (034947); Official Action dated Apr. 13, 2005.

Russian Patent Application No. 2002132899/13 (034947); Official Action dated Oct. 21, 2005.

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye, S., "Biotechnological Advances in Goat Reproduction", J. Anim. Sci. 75(2): 578-585. (1996).
Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a Flow Cytometer," University of Washington Feb. 19, 1996.
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beef", J. Anim. Sci. 69:1403. (1991).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215 (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterolle Prior to Puberty in Beef Heifers". J. Anim. Sci. 49:1276. (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., Et Al., 1999 Sexual Dimorphism In IVM-IVF Bovine Embryos Produced from X and Y Chromosome-Bearing Spermatozoa By High Speed Flow Cytometry. Theriogenology. 52: 35-48.
BigosBigos, Martin "Nine Color Eleven Parameter Immunophenotyping Using Three Laser Flow Cytometry," Stanford University Dec. 22, 1998.
Bioxcell, Bovine Sperm Preservation, Advertisment Jun. 28, 2005.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III. Culling Strategies and Nontraditional Management-Systems", J. Anim. Sci. 65:963. 1987.
Bracher, V. and Allen, W.R., "Videoendoscopic Examination of the Mare's Uterus: I. Findings in Normal Fertile Mares", Equine Veterinary Journal, vol. 24, p. 274-278. 1992.
Braselton, W. E. and McShan, W. H., "Purification and Properties of Follicle Stimulating and Luteinizing Hormones From Horse Pituitary Glands" Arch. Biochem. Biophys. 139:45-48. 1970.
Braun, J. et al, "Effect of Different Protein Supplements on Motility and Plasma Membrane Integrity of Frozen- Thawed Stallion Spermatozoa", Cryobiology (1995) 32:487-492.
Brethour, J. R. and Jaeger, J. R., "The Single Calf Heifer System", Kansas Agric. Sta. Rep of Progress 570. 1989.

Brinsko, S.P. et al., "Artificial Insemination and Preservation of Semen." Veterinary Clinics of North America:Equine Practice vol. 8 No. 1 Apr. 1992 pp. 205-218.
Bristol, F. "Breeding Behavior of a Stallion at Pasture With 20 Mares in Synchronized Oestrus" J. Reprod. Fertil. Suppl. 32:71. 1982.
Brookes, A. J. and O'Byrne, M., "Use of Cow-Heifers in Beef Production" J. of the Royal Agricultural Society of England 126:30. 1965.
Buchanan, B.R. "Pregnancy Rates in Mares Following a Single Insemination with a Low Number of Spermatozoa into the Tip of the Uterine Horn" Theriogenology p. 395 vol. 51, Iss. 1, Jan. 1, 1999.
Burns, P. D. and Spitzer, J.C., "Influence of Biostimulation on Reproduction in Postpartum Beef-Cows", J. Anim. Sci. 70:358. 1992.
Burwash, L. D., et al., "Relationship of Duration of Estrus to Pregnancy Rate in Normally Cycling, Non Lactating Mares" J.A.V.M.A. 165:714-716. 1974.
Byerley, D. J., et al., "Pregnancy Rates of Beef Heifers Bred Either on Puberal or Third Estrus". J Anim. Sci. 65:645. 1987.
Caslick, E. A., "The Vulva and the Vulvo-Vaginal Orifice and its Relation to Genital Health of the Thoroughbred Mare", Cornell Veterinarian, vol. 27, p. 178-187. 1937.
Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.
Cave-Penney, Tony, "Sexed Semen Offers Faster Genetic Gain", Farming News, Livestock Supplement, Feb. 1997, p. 28.
*Celestron: Telescope Basics*: www.celestron.com/tb-2ref/htm: 4 pages—no publication info available.
Intentionally left blank.
Chandler, J. E., et al, "Bovine Spermatozoal Head Size Variation and Evaluation of a Separation Technique Based on this Size", Therio. 52, p. 1021-1034. 1999.
Chen, S.H. "Effects of Oocyte Activation and Treatment of Spermatozoa on Embryonic Development Following Intracytoplasmic Sperm Injection in Cattle" Theriogenology 48:1265-1273, 1997.
Chen, Y. et al., Survival of Bull Spermatozoa Seeded and Frozen at Different Rates in Egg Yolk-Tris and Whole Milk Extenders, 1993 J Dairy Sci 76:1028-1034.
Chin, W. W. and Boime, I. 1990. In Glycoprotein Hormones. Serona Symp. Norwell, MA. pp. 19-20.
Choi, Y.H. "Developmental Cappacity of Equine Oocytes Matured and Cultured in Equine Trophoblast-Conditioned Media" Theriogenoogy 56: 320-339, 2001.
Clement, F., et al., "Which Insemination Fertilizes When Several Successive Inseminations are Performed Before Ovulation" 7th Int. Symp. Eq. Repro. 151. 1998 abstr.
Cran, D. G., et al., "The Predetermination of Embryonic Sex Using Flow Cytometrically Separated X and Y Spermatozoa" Human Reproduction Update 1996, vol. 2 (4) p. 355-363.
Crowley, J.P. "The facts of Once-Bred Heifer Production" School of Agric., Univ. of Aberdeen, Scotland. 1973.
Curran, S. "Fetal Gender Determination" in *Equine Diagnostic Ultrasonography* 1 st ed. Rantanen, N.W. and McKinnon A.O. (eds.) Williams and Williams, 1998, p. 165-169.
da Silva, Coutinho M.A.."Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.
*DakoCytomation, "MoFlo® Sorters"* http://www.dakocytomation.us/prod_productrelatedinformation?url=gprod_moflo_index.htm one page, printed Jun. 26, 2003.
Database up 1 BR9704313 (Alves, De Resende et al) Jun. 4, 1999.
de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Demick, D.S., et al. "Effect of Cooling, Storage, Glycerization and Spermatozoal Numbers on Equine Fertility" J Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado Sate University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation, "Coat-A-Count"* http://www. Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (*Panthera tigris*)" J. Reprod. Fertil. 107:53-58. 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203, 1999.

Dresser D.W. et at. Analysis of DNAcontent ofLiving Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertile. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves",Ohio State University Dept. of Animal Scieneces. 1966 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do ? Why Are They Important?" Proc of the NAAB Tech. Conf. On Artificial Insemination and Reproduction, 62-70 (1984).

Francon, M. and Yamamoto, T., "Un Noveau et tres simple dispositif interferentiel applicable as microscope" Optica Acta 9, p. 395-408. 1962.

Fuller, Robert R. "Characterizing Submicron Vesicles With Wavelenth-Restored Fluorescence in Flow Cytometry," University of Illinois, May 13, 1996.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gombe, S. and Hansel, W. "Plasma Luteinizing☐Hormone (LH) and Progesterone Levels in Heifers on Restricted Energy Intakes." J. Anim. Sci. 37:728. 1973.

Goppert-Mayer, "Uber Elementarakle mit zwei Quantensprugen Von Maria Copper -Mayer" p. 273 Article in German no pub date available.

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility, Abstract, Vet Clin North Am. Equire Pract. Apr. 1996, vol. 12(1), p. 119-130.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal☐Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Hall, J. B., et al., "Effect of Age and Pattern of Gain on Induction of Puberty with a Progestin in Beef Heifers." J. Anim. Sci. 75:1606 (1997).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. .J. "System of Production of Beef From Once Calved Heifers." In: J.C. Taylor (Ed.) *The Early Calving of Heifers and its Impact on Beef Production*. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117; SciAm. 1976, 161.234.

Hilton, G. G., et al., "An Evaluation of Current and Alternative Systems for Quality Grading Carcasses of Mature Slaugher Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Coception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine." 140ct. 1977, Science, vol. 198.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (*Mustela putorious furo*) and Pregnancies After Laparoscopic Intrauterine Insemination With Frozen-Thawed Spermatozoa." J. Reprod. Fertile. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc. 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 989, p. 181-190.

IMV Technologies, Protocol of Bioxcell with Fresh Semen, 1 page, 2000.

IMV Technologies, Protocol of Bioxcell with Fresh Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production.* 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-660.

Johnson, A. L. "Pulsatile Administration of Gonadotropin Releasing Hormone Advances Ovulation in Cycling Mares", Biol. Reprod. 35:1123-1130, (1986).

Johnson, A. L., et al., "Use of Gonadotropin-Releasing Hormone (GnRH) Treatment to Induce Multiple Ovulations in the Anestrous Mare" Eq. Vet. Sci. 8:130-134, (1988).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Sex Preselection by Flow Cytometric Separation of X and Y Chromosome Bearing Spermatozoa Based on DNA Difference: a Review." Reprod. Fertil. Dev. 7:893-903. (1995).

Johnson, L.A., et al., "Flow Sorting of X and Y Chromosome-Bearing Spermatozoa into Two Populations", Gamete Res. 16:203-212. (1987).

Joseph, R. L. "Carcass composition and meal quality in once calved heifers." In: J.C. Taylor (Ed.) *The Early Calving of Heifers and its Impact on Beef Production.* 143. (1975).

Joseph, R. L. and J. P. Crowley. "Meat Quality of Once-Calved Heifers." Irish J. of Agric. Research 10:281. (1971).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al., "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Lightwave Electronics, "Xcyte," www.LightwaveElecronics.com, no publication date info avail.

Lindsey, A. C., et al., "Low Dose Insemination of Mares Using Non-Sorted and Sex-Sorted Sperm" Animal Reproduction Science 68 p. 279-89 (2001).

Lindsey, A., et al., "Hysteroscopic Insemination of Mares with Nonfrozen Low-dose Unsexed or Sex-sorted Spermatozoa", pp. 1-15 currently unpublished, no publication info avail.

Linge, F. "Faltforsok med djupfrost sperma (Field Trials With Frozen Sperm)." Farskotsel. 52:12-13. (1972).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. abstr., vol. 52, p. 1353-1362, 1999.

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug In Dairy Cattle?", Animal Reserach Station, Private Bag, Hamilton, New Zealand, Therio. vol. 18, No. 3, p. 245-253 (1982.

Manni, Jeff. "To-Photon Excitation Expands the Capabilities of Laser-Scanning Microscopy," no publication info available.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production.* (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internet. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. *Equine Reproduction.* Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo prduction with four bovine sperm preparation protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991, vol. 30, pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-422. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 54:548, (Apr. 1971).

Molinia, F. C., et al., "Successful Fertilization After Superovulation and Laparoscopic Intrauterine Insemination of the Brushtail Possum *Trichosurus vulpecula*, and Tammar Wallaby, *Macropus eugenii*." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-362 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Method in Enzymology vol. 155 p. 335-350 (1978).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Su;;l. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female—A Means of Increasing Meat Production." Proc. Symp. on the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M.M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 23:115-121. (1975).

Parrish, J. J., et al., "Capacitation of Bovine Sperm by Heparin", Department Of Meat and Animal Science, Biology of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W, et al., "Factors Influencing the Fertility of Stallion Spermatozoa in an A. I. Program." Proc. 8th International Congress Anim. Reprod. A. I. Krakow, Poland. 4:1046-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al., "Sex Preselection in Mammals? Separation of Sperm Bearing the Y and "O" Chromosomes in the Vole *Microtus oregoni*", Science vol. 218, p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, et al, "Revival of Spermatozoa After Vitrification and Dehydration at Low Temperatures," Nature, 164:666 (1994).

Prokofiev M.I. Regoulyatsia Razmnozhenia Selskokhozyastvennykh Zhivotnykh, Leningrad, NAOUKA Publishing House, 1983, pp. 181-195.

Providence, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rathi, R. et al., "Evaluation of In Vitro Capacitation of Stallion Spermatozoa", Biology of Reproduction 2001, vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al. "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-2051, 1996.

Rieger, D., et al., "The Relationship Between the Time of First Cleavage of Fertilized Cattle Oocytes and Their Development to the Blastocyte Stage", Therio. 1999, p. 190.

Rigby, S. L., et al., "Pregnancy Rates in Mares Following Hysteroscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Vitro Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Roy, J. H., "Rearing Dairy-Herd Replacements." Journal of the Society of Dairy Technology 31:73-79 (1978).

Rutter, L. M., et al., "Effect of Abomasal Infusion of Propionate on the GnRH-Induced.Luteinizing Hormone Release in Prepuberal Heifers." J. Anim. Sci. 56:1167 (1983).

Salamon, S., *Artificial Insemination of Sheep*, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) (1961 & 1978 Combined) Chapters 16 and 17 are the complete article.

Schenk, J. L. "Applying Semen Sexing Technology to the AI Industry", the 18th Technical Conference on Artificial Insemination & Reproduction, 2000.

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al., "Effects of Nutrition and Season on the Onset of Puberty in the Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34 Sep. 2001.

Seidel, G. E. Jr. Sexing mammalian spermatozoa and embryos-state of the art Journal of Reproduction and Fertility Supp 54, 477-487 1999.

Seidel, G. E. Jr et al., "Current Status of Sexing Mammalian Spermatozoa," Society for Reproduction and fertility, p. 733-743, 2002.

Seidel, G. E. Jr., "Commercilizing Reproductive Biotechnology—The Approach used by XY, Inc.," Theriogenology, p. 5, 1999.

Seidel, G. E. Jr., et al, "Insemination of Heifers With Low Numbers Of Frozen Spermatozoa", CSU, Atlantic Breeders Cooperative, Lancaster, PA, DUO Dairy, Loveland, CO, Jul. 1996.

Seidel, G. E. Jr., et al, "Sexing Mammalian Sperm—Overview", Therio. 52:1264-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20., Oct. 1988.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horiculture and Food Research Institute of New Zealand Ltd., Hamilton, New Zealand (PNS) Nov. 12, 1997 Abstract.

Sharpe, Jonathan, Thesis; "An Introduction of Flow Cytometry", Ch. 2-2.2, 1997.

Sharpe, Jonathan, Thesis; "Gender Preselection-Principle Scienctific Options," Ch. 3.4-3.4.8, 1997.

Sharpe, Jonathan, Thesis; "Sperm Sexing using Flow Cytometry," Ch. 3.5-3.5.8, 1997.

Sharpe, Jonathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress on Anim. Repro. and A. I. 204-208. (1976).

Shorthose, W. R. and P. V. Harris. "Effects of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al., "USDA Maturity Indexes and Palatability of Beef Rib Steaks." J. Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002, no publication date avail.

Spectra-Physics Products, "Fcbar" http://www.splasers.com/products/oem_products/ov_fcbar.html two pages printed Nov. 14, 2002, no publication date avail.

Spectra-Physics, The Solid State Laser Company, Vanguard 2000-HMD 532, www.specra-physics.com, no publication date avail.

Spectra-Physics, The Solid State Laser Company, Vanguard 350-HMD 355, www.specra-physics.com, no publication date avail.

Squires, E. L, et al., "Effect of Dose of GnRH Analog on Ovulation in Mares." Therio. 41:757-769. (1994).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Proceedings for Handling Frozen Equine Semen for Maximum Reproductive Efficiency", pp. 1, 39-41, 81-89, no publication date available.

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commerical Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparlurient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrus Periods." J.A.V.M.A. 162:895-898. (1973).

Swanson, E. W. "Future Research on Problems of Increasing Meat Production by Early Calving." In: J.C. Taylor (ed.) *The Early Calving of Heifers and Its Impact on Beef Production.* (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440. , Anim. Proc. (1985) vol. 40.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE—100—XHP"*, www.tbsp.com, 2 pages, Jan. 2002.

Unruh, J. A. "Effects of Endogenous and Exogenous Growth-Promising Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

Van Munster, E. B., et al, "Difference in Sperm Head Volume as a Theoretical Basis for Sorting X & Y-Bearing Spermatozoa: Potentials and Limitations", Therio 52, pp. 1281-1293 (1999).

Van Munster, E. B., et al, "Difference in Volume of X- and Y-chromosome Bearing Bovine Sperm Heads Matches Difference in DNA Content" Cytometry vol. 35 p. 125-128 (1999).

Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

Van Munster, E. B., et al, "Reconstruction of Optical Pathlength Distributions From Images Obtained by a Wide Field Differential Interference Contrast Microscope", J. of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J., et al., "Development of a Non-surgical Deep Intra Uterine Insemination Technique", Boar Semen Preservation IV, IVth International Conference on Boar Semen Preservation, Maryland, pp. 262-263.

Vazquez, J., et al., "Successful low dose insemination by a fiber optic Endoscope technique in the Sow" Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservation of Spermatozoa and the Assessment of Their Post-Thawing Function," Reprod. Fertil. Dev. 7:871-891 (1995) Abstract.

Wheeler, T. L., et al., "Effect of Marbling Degree on Beef Palatability in *Bos-taurus* and *Bos-indicus* cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Wintzer Et al.:"Krankheiten des Pferdes Ein Leitfaden fur Studium und Praxiz," 1982, nParey, Berlin Hamburg XP002281450.

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, no publication info avail.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al., "Sex-Sorting and Re-cryopreservation of Frozen-Thawed Ram Sperm for In Vitro Embryo Production" Theriogenology , vol. 59. (2003) pp. 209.

Dhali et al. Vitrification of Buffalo (*Bubalus bubalis*)Oocytes, Embryo Theriogenology vol. 53, pp. 1295-1303 (2000).

Borini et al. Cryopreservation of Mature Oocytes: The use of a trypsin inhbitor enhances fertilization and obtained embryos rates, Fertil. Steril. (1997), vol. 68 (Suppl.).

Cran et al. The predetermination of embryonic sex using flow cytometrically separated X and Y spermatozoa, Human Reproduction Update 1996, vol. 2, No. 4 pp. 355-363.

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science, vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resolution DNA analysis of X- and Y- chromosome bearing sperm, Cytometry 25:191-199 (1996).

van Munster, E. B. Inferometry in flor to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/Isrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenck J. L., Embryo production from superovulated cattle following insemination of sexed sperm, Theriogenology, 65 (2006) 299-307.

Garner, D. L., Flow cytometric sexing of mammalian sperm, Theriogenology, (2006) pp. 15.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Buchanan, B.R., et al, "Insemination of Mares with Low Numbers of Either Unsexed or Sexed Spermatozoa", Theriogenology, vol. 53, pp. 1333-1344, (2000).

Catt, et al., "Assessment of Ram and Boar Spermatozoa During Cell-Sorting by Flow Cytometry", Reproduction Dom Animal, vol. 32, pp. 251-258 (1997).

Chandler, J.E., "Videomicroscopic Comparison of Bull Sperm and Leukocyte Chromosome Areas as Related to Gender", J Dairy Sci 73, p. 2129-2135. 1990.

Chandler, J.E., et al, "Bovine Spermatozoal Head Size Variation and Evaluation of a Separation Technique Based on this Size", Theriogenology 52, p. 1021-1034. 1999.

Chung, Y.G., et al., 1998. Artificial insemination of superovulated heifers with 600,000 sexed sperm. J Anim. Sci. Suppl. 1. 836:215. abstr.

Cran, D.G., et al. 1997. Production of Lambs by Low Dose Intrauterine Insemination With Flow Cytometrically Sorted and Unsorted Semen, Scottish Agricultural College, UK, Theriogenology, p. 267.

Cran, D.G., et al., 1993. Production of Bovine Calves Following Separation Of X-Chromosome and Y-Chromosome Bearing Sperm And In Vitro Fertilization. Vet. Rec. 132:40-41.

Cran, D.G., et al., "Sex Preselected in Cattle: A Field Trial", Veterinary Record 136, 1995, p. 495-496.

Cui, K., "Size Differences between human X and Y Spermatozoa and prefertilization diagnosis", Molecular Human Reproduction, vol. 3, No. 1, pp. 61-67. 1997.

Cui, K., "X Larger than Y", Nature 366, p. 177-118, 1993.

Day, B.N., et al., 1998. Birth of piglets preselected for gender following in vitro fertilization of in vitro matured pig oocytes by X and Y bearing spermatozoa sorted by high speed flow cytometry. Theriogenology. 49(1):360. abstr.

Dean, P.N., et al., 1978. Hydrodynamic orientation of spermatozoa heads for flow cytometry. Biophys. J. 23:7-13.

Foulkes, J.A., et al., 1977. Artificial insemination of cattle using varying numbers of spermatozoa. Vet. Rec. 101:205.

Fugger, E.F., "Clinical Experience with Flow Cytometric Separation of Human X- and Y- Chromosome Bearing Sperm", Theriogenology, vol. 52, pp. 1435-1440 (1999).

Fulwyler, M.J. 1965. Electronic separation of biological cells by volume. Science. 150:910.

Fulwyler, M.J. 1977. Hydrodynamic orientation of cells. J Histochem. Cytochem. 25:781-783.

Garner, D.L., et al., 1983. Quantification of the X and Y chromosome-bearing spermatozoa of domestic animals by flow cytometry. Biol. Reprod. 28:312-321.

Gledhill, B.L. 1988. Gender preselection: historical, technical and ethical perspective. Sernin Reprod. Endocrinol. 6:385-395.

Gurnsey, M.P., and Johnson, L.A., "Recent improvements in efficiency of flow cytometric sorting of X and Y- chromosome bearing sperm of domestic animals: a review", 1998, New Zealand Society of Animal Protection, three pages.

"Hamamatsu, Photomultiplier Tubes", web page, http://www.optics.org/hamamatsu/pmt.html, printed out on Apr. 15, 2000, 4 pages total, no publication date available.

"Hamamatsu, Technical Information", web page, http://www.optics.org/hamamatsu/photodiode.html, printed out on Apr. 15, 2000, 6 pages total, publication date originally Mar. 3, 1997.

Hamano, K., et al., "Gender Preselection in Cattle with Intracytoplasmically Injected, Flow Cytometrically Sorted Sperm Heads", Biology of Reproduction 60, pp. 1194-1197. 1999.

Jafar, et al., "Sex Selection in Mammals: A Review", Theriogenology, vol. 46, pp. 191-200 (1996).

Johnson, L., "Sex Preselection in Swine: Flow Cytometric Sorting of X- and Y- Chromosome Bearing Sperm to Produce Offspring", Boar Semen Preservation IV, 2000, pp. 107-114.

Johnson, L..A., "Sex Preselection in Rabbits: Live Births from X and Y Sperm Separated by DNA and Cell Sorting" Biology of Reproduction, vol. 41, pp. 199-203 (1989).

Johnson, L..A., "Sex Preselection in Swine: Altered Sex Ratios in Offspring Following Surgical Insemination of Flow Sorted X- and Y- Bearing Sperm", Reproduction in Domestic Animals, vol. 26, pp. 309-314 (1991).

Johnson, L.A. 1994. Isolation of X- and Y-bearing spermatozoa for sex preselection. *In* : Oxford Reviews of Reproductive Biology. Ed. HH Charlton. Oxford University Press. 303-326.

Johnson, L.A. 1997. Advances in gender preselection in swine. J. Reprod. Fert. Suppl. 52:255-266.

Johnson, L.A., "Gender preselection in Mammals: An overview", Deutsch, Tierarztl. Wschr, vol. 103, pp. 288-291 (1996).

Johnson, L.A., "Flow cytometric determination of spermatozoa sex ratio in semen purportedly enriched for X or Y bearing spermatozoa" Theriogenology. 29:265. abstr., vol. 29, Issue 1, Jan. 1988.

Johnson, L.A., "Gender preselection in domestic animals using flow cytometrically sorted sperm" J Anim. Sci. Suppl 1.70:8-18. 1992.

Johnson, L.A., "The safety of sperm selection by flow cytometry" Harn. Reprod. 9(5):758, 1994.

Johnson, L.A., et al. "Sex Preselection: High-speed flow cytometric sorting of X and Y sperm for maximum efficiency", Theriogenology, vol. 52, (1999), pp. 1323-1341.

Johnson, L.A., et al., "Enhanced flow cytometric sorting of mammalian X and Y sperm: high speed sorting and orienting nozzle for artificial insemination", Theriogenology. 49(1):361. abstr., 1988.

Johnson, L.A., et al., "Improved flow sorting resolution of X- and Y- chromosome bearing viable sperm separation using dual staining and dead cell gating" Cytometry 17 (suppl 7) 83, 1994.

Johnson, L.A., et al. "Modification of a Laser-Based flow Cytometer for High-Resolution DNA Analysis of Mammalian Spermatozoa", Cytometry 7, pp. 268-273 (1986).

Johnson, L.A.., "Flow cytometry of X- and Y- chromosome bearing sperm for DNA using an improved preparation method and staining with Hoechst" 333-42. Garn. Res. 17:203-212, 1987.

Johnson, L., "Successful Gender Preselection in Farm Animals", Agricultural Biotechnology, p. 439-452. (1998).

Kachel, et al., "Uniform Lateral Orientation, Cause by Flow Forces, of Flat Particles in Flow-Through Systems", The Journal of Histochemistry and Cytochemistry, 1997, vol. 25, No. 7, pp. 774-780.

Lapin, D.R. and Ginther, O.J. 1977. Induction of ovulation and multiple ovulations in seasonally anovulatory and ovulatory mares with an equine pituitary extract. J. Anim. Sci. 44:834-842.

Levinson, G., et al., 1995. DNA-based X-enriched sperm separation as an adjunct to preimplantation genetic testing for the preparation of X-linked disease. Mol. Human Reprod. 10:979-982.

Lu, K.H., et al., "In Vitro Fertilization with Flow-Cytometrically-Sorted Bovine Sperm", Therio 52, p. 1393-1405. (1999).

Maxwell, W.M.C., et al., 1993. Fertility of Superovulated Ewes after Intrauterine or Oviductal Insemination with Low Numbers of Fresh or Frozen-Thawed Spermatozoa. Reprod. Fertil. Dev. 5:57-63.

Martinez, E.A., et al., "Successful Low-Dose Insemination by a Fiberoptic Endoscope Technique in the Sow", Proceedings Annual Conference of the International Embryo Transfer Society, Netherlands, Theriogenology, vol. 53, Jan. 2000, pp. 201.

McNutt, et al., "Flow Cytometric Sorting of Sperm: Influence on Fertilization and Embryo/Fetal Development in the Rabbits", Molecular Reproduction and Development, vol. 43, pp. 261-267 (1996).

Merton, J., et al., "Effect of Flow Cytometrically Sorted Frozen/Thawed Semen on Success Rate of In Vitro Bovine Embryo Production", Theriogenology 47, p. 295. (1997).

Munne, S. 1994. Flow cytometry separation of X and Y spermatozoa could be detrimental to human embryos. Hum. Reprod. 9(5):758.

Pinkel, D., et al, "Flow Cytometric Determination of the Proportions of X- and Y- Chromosome-Bearing Sperm in Samples of Purportedly Separated Bull Sperm", Journal of Animal Science, vol. 60, pp. 1303-1307 (1998).

Pinkel, D., et al., 1985b. High resolution DNA measurements of mammalian spermatozoa. Cytometry. 3:1-9.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquistion and Processing V, p. 1-11 (1998).

Rath, D., et al., "Low Dose Insemination Technique in the Pig", Boar Semen Preservation IV, 2000, pp. 115-118.

Rath, D., et al., "Production of Piglets Preselected for Sex Following in Vitro Fertilization with X and Y Chromosome-Bearing Spermatozoa Sorted by Flow Cytometry", Theriogenology, 47, pp. 795-800 (1997).

Rens, W., et al., "A Novel Nozzle for More Efficient Sperm Orientation to Improve Sorting Efficiency of X and Y Chromosome-Bearing Sperm", Technical Notes, Cytometry 33, 1998, pp. 476-481.

Rens, W., et al., "Improved Flow Cytometric Sorting of X- and Y-Chromosome Bearing Sperm: Substantial Increase in Yield of Sexed Semen", Molecular Reproduction and Development, 1999, pp. 50-56.

Rowley, H-S., et al., 1990. Effect of insemination volume on embryo recovery in mares. J. Equine Vet. Sci. 10:298-300.

Schenk, J.L., "Cryopreservation of flow-sorted bovine spermatozoa", Theriogenology, vol. 52, 1375-1391 (1999).

Schenk, J.L. and Seidel, Jr., G.E., "Imminent Commercialization of Sexed Bovine", Proceedings The Range Beef Cow Symposium XVL, 1999, pp. 89-96.

Schmid R.L., et al, "Fertilization with Sexed Equine Spermatozoa Using Intracytoplasmic Sperm Injection and Oviductal Insemination", 7th International Symposium on Equine Reproduction, pp. 139(Abstract) (1998).

Seidel, G., et al, "Sexing Mammalian Sperm—Overview", Theriogenology 52: 1267-1272, (1999).

Seidel, G., "Status of Sexing Semen for Beef Cattle", Texas A&M Univeristy 45th Annual Beef Cattle Short Course and Trade Show Proceedings, Aug. 9-11, pp. 11124-11127, (1999).

Seidel, G., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G.E. Jr, et al., "Artificial Insemination of Heifers with Cooled, Unfrozen Sexed Semen", Theriogenology, vol. 49 pp. 365 (Abstract) (1998).

Seidel, G.E. Jr, et al., "Insemination of Heifers with Sexed Sperm", Theriogenology, vol. 52, pp. 1407-1421 (1999).

Seidel, G.E. Jr., "Uterine Horn Insemination of Heifers With Very Low Numbers of Nonfrozen and Sexed Spermatozoa", Atlantic Breeders Cooperative, Theriogenology 48: pp. 1255-1264, (1997).

Seidel, G.E. Jr.,et al., 1999. Insemination of heifers with sexed frozen or sexed liquid semen. Theriogenology. 51. (in press). abstr.

Seidel, Jr., G. E., "Artificial Insemination With X-and Y-Bearing Bovine Sperm", Animal Reproduction and Biotechnology Laboratory, Colorado State University, (1996).

Seidel, Jr., G. E., et al, "Insemination of Holstein Heifers With Very Low Numbers Of Unfrozen Spermatozoa", Colorado State University, Atlantic Breeders Cooperative, (1995).

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, pp. 127-130 (1996).

Sumner, A.T. and Robinson, J.A., "A Difference in Dry mass between the heads of X and Y-bearing human Spermatozoa", J Reprod Fert 48, p. 9-15 (1976).

U.S. Appl. No. 09/015,454, entitled "System for Improving Yield of Sexed Embryos in Mammals", filed on Jan. 29, 1998, 59 pages which includes drawings.

U.S. Appl. No. 09/448,643, entitled "Multiple Sexed Embryo Production System for Mammals", filed Nov. 24, 1999.

U.S. Appl. No. 09/454,488, entitled "Improved Flow Cytometer Nozzle and Flow Cytometer Sample Handling Methods", filed Dec. 3, 1999.

U.S. Appl. No. 60/094,720, entitled "System for Low Dose Insemination of Equines", filed Jul. 30, 1998.

U.S. Appl. No. 60/113,143, entitled "Equine Insemination System", filed Dec. 18, 1998.

U.S. Appl. No. 60/203,089, entitled "Detector System for Resolving Small Differences in Photo-generated Signal", filed May 9, 2000.

U.S. Appl. No. 60/224,050, entitled "Integrated System for Herd Management With Terminal-Cross Program Using Sexed Semen", filed Aug. 9, 2000.

U.S. Appl. No. 60/238,294, entitled "Hysteroscopic Insemination of Mares" filed Oct. 5, 2000.

U.S. Appl. No. 09/511,959, entitled "Methods For Improving Sheath Fluids and Collection Systems For Sex-Specific Cytometer Sorting of Sperm", filed Feb. 23, 2001.

U.S. Appl. No. 09/001,394, entitled "Improved Sheath Fluids and Collection Systems for Sex-Specific Cytometer Sorting of Sperm", filed Dec. 31, 1997, 83 pages & 4 Drawings.

U.S. Appl. No. 60/211,093, entitled "Integrated System for Herd Management Using Sexed Semen", filed Jun. 12, 2000. Serial Number.

Van Munster, E.B., "Geslachtsbepaling met interferometrie", Derde prijs NtvN-prijsvraag voor pas-gepromoveerden 65/4, p. 95-98 (1999).

Van Munster, E.B., et al, "Difference in Sperm Head Volume as a Theoretical Basis for Sorting X & Y-Bearing Spermatozoa: Potentials and Limitations", Therio 52, pp. 1281-1293 (1999).

Van Munster, E.B., et al, "Difference in Volume of X- and Y-chromosome Bearing Bovine Sperm Heads Matches Difference in DNA Content" Cytometry 35 p. 125-128 (1999).

Van Munster, E.B., et al, "Measurement-based evaluation of optical path length distributions reconstructed from simulated differential interference contrast images", J of Microscopy 192, Pt. 2, p. 170-176 (1998).

Van Munster, E.B., et al, "Reconstruction of optical path length distributions form images obtained by a wide field differential interference contrast microscope", J of Microscopy 188, Pt. 2, p. 149-157 (1997).

Vazquez, J., et al., "A.I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Hypoosmotic Swelling Test as Predictor of the Membrane Integrity in Boar Spermatozoa", Boar Semen Preservation IV, IVth International Conference on Boar Semen Preservation, Maryland, pp. 263. ,no pub. date info avail.

Welch G.R., et al., 1994. Fluidic and optical modifications to a FACS IV for flow sorting of X- and Y- chromosome bearing sperm based on DNA. Cytometry 17 (suppl. 7): 74.

Welch, G., et al., "Flow Cytometric Sperm Sorting and PCR to Confirm Separation of X- and Y- Chromosome Bearing Bovine Sperm", Animal Biotechnology, 6, pp. 131-139 (1995).

Windsor, D.P., et al, "Sex Predetermination by Separation of X and Y Chromosome-bearing Sperm: A Review", Reproduction of Fertilization and Development 5, pp. 155-171, (1993).

Johnson, L.A., et al, 1996 Gender preselection in mammals. XX Beltsville Symposium in Agricultural Research Technology's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735 filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed Sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, Tom and Currin, John Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $In Asia B. Japan; www.agnet.org/library/article/eb384b.html.

Crichton,E.; Huffman,S.;McSweeney,K.;and Schenk, J. 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H.,Caraviello, D.Z., Satter, L.D. ,Fricke, P.M. and Wiltbank, M.C.; Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology www.foodsci.uoguelph.ca/dairyedu/biosytheses.html.

Milk Production Released Jul. 18, 2006, by the National Agricultural Statistics Service (NASS), Agri. Stats. Board, US Dept of Agri.

De Vries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reproduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Mobility Ofspermatozoa of the Japaneses Eel *Anguilla japonica*, National Research Institute of Aquaculture, Nansei, Mie, Nov. 10, 1999 UJNR Technical Report No. 28.

Morisawa, M. The Process of the Initiation of Sperm Motility; Laboratory of Physiology, Ocean Research Institute, University of Tokyo, no publication info.

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa, School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624, (2000).

Jenkins, A.D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 258, issue 9, May 1983, pp. 5392-5399.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and $\beta$-D-Glucuron idase Activity as Indicators of Sea Bass Semen Quality; Biology of Reproduction 70, 1679-1684 (2004) Published online before print Feb. 11, 2004.

Parallel India Patent Application Number IN/PCT/2002/01393; Office Action dated Oct. 6, 2006.

\* cited by examiner

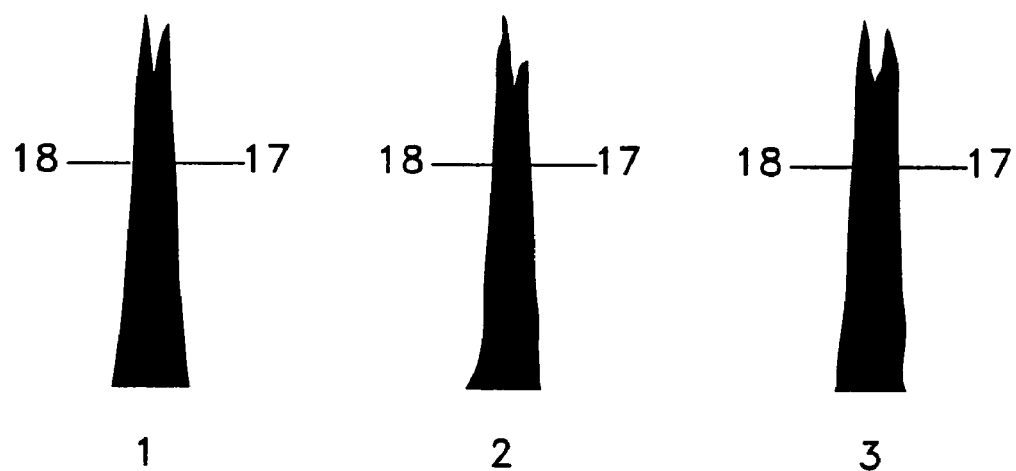
Fig. 3a
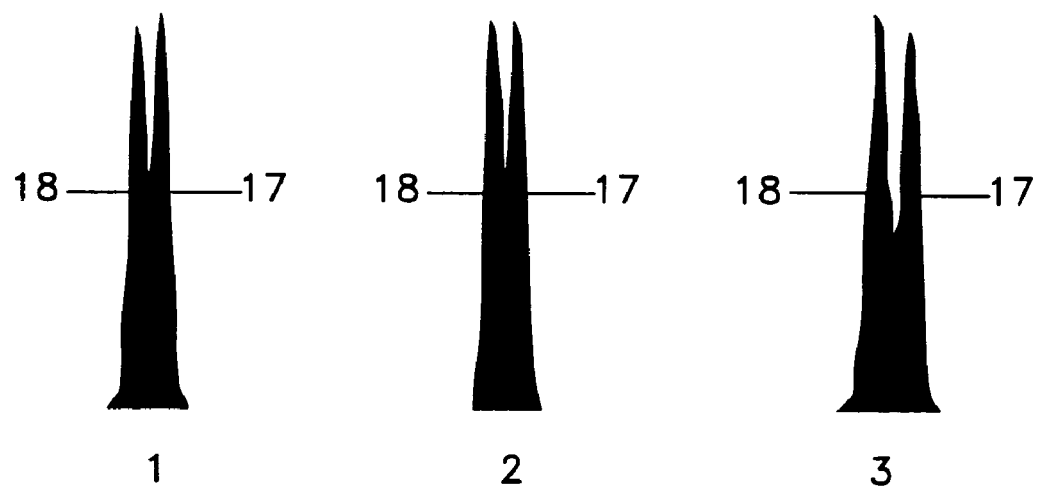
Fig. 3b
Fig. 3

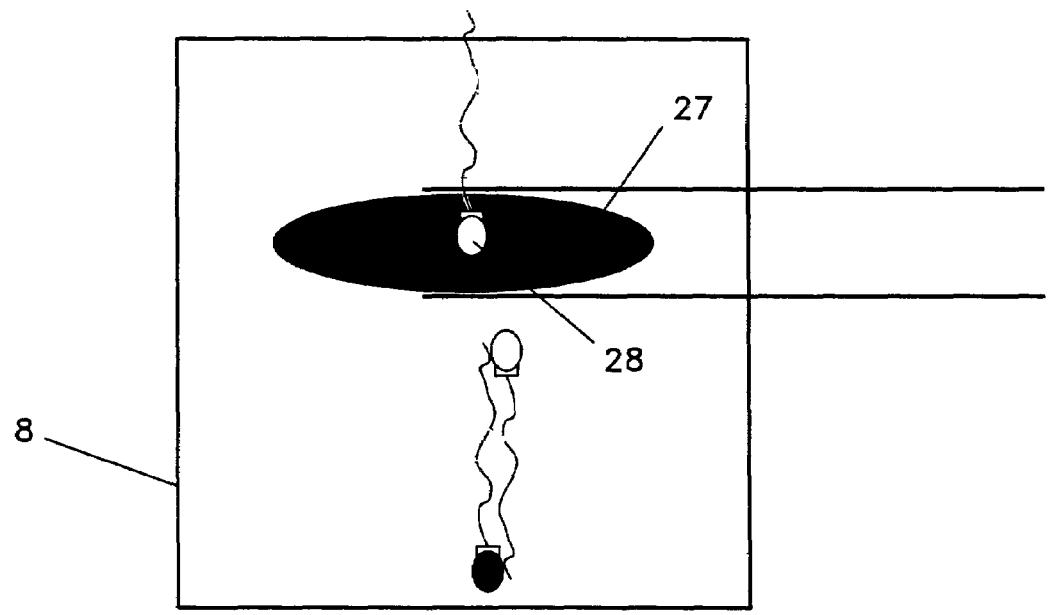
Fig. 13a
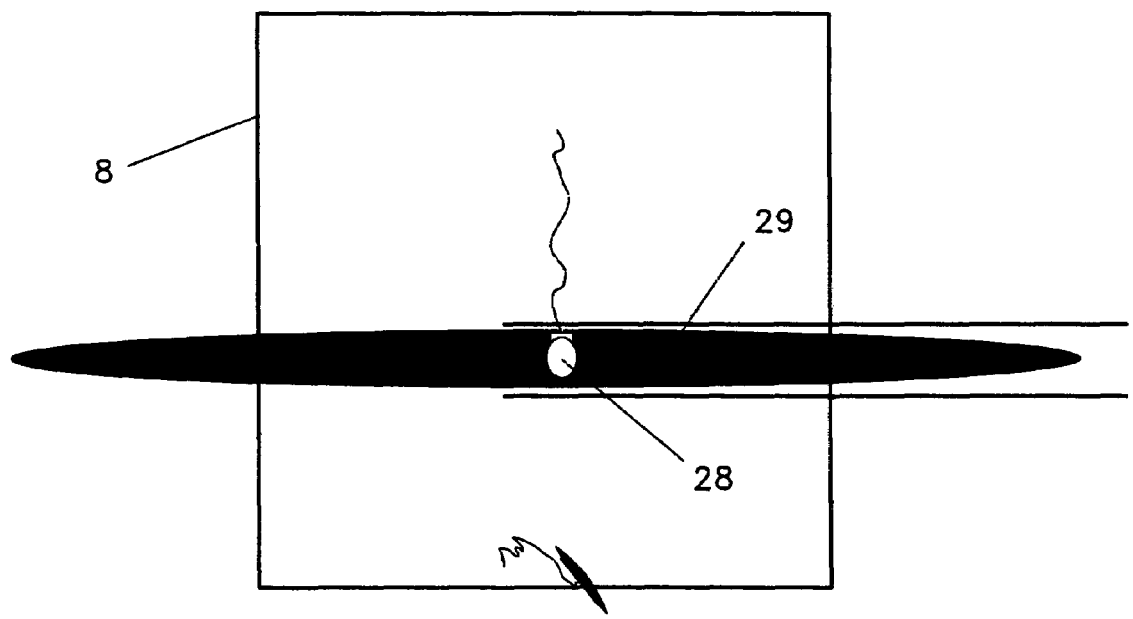
Fig. 13b
Fig. 13

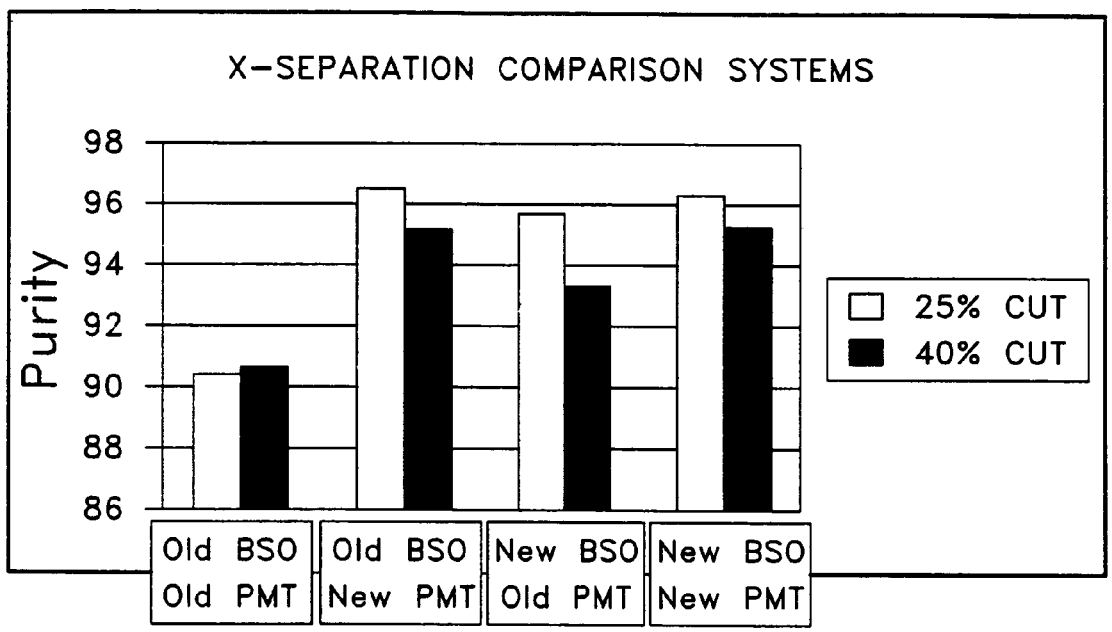
Fig. 14a
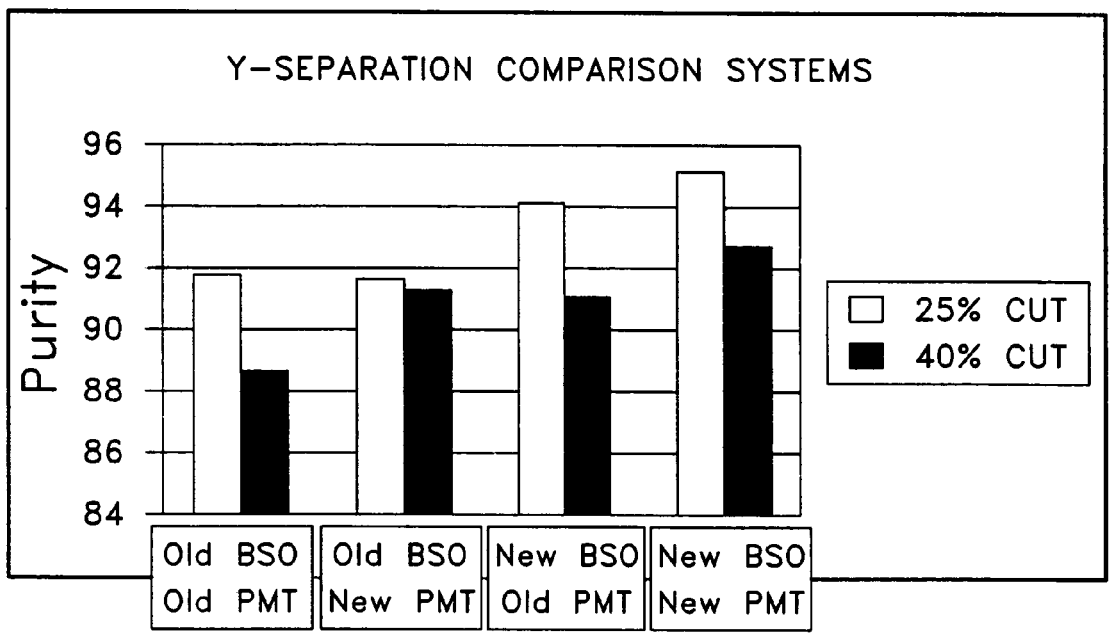
Fig. 14b
Fig. 14

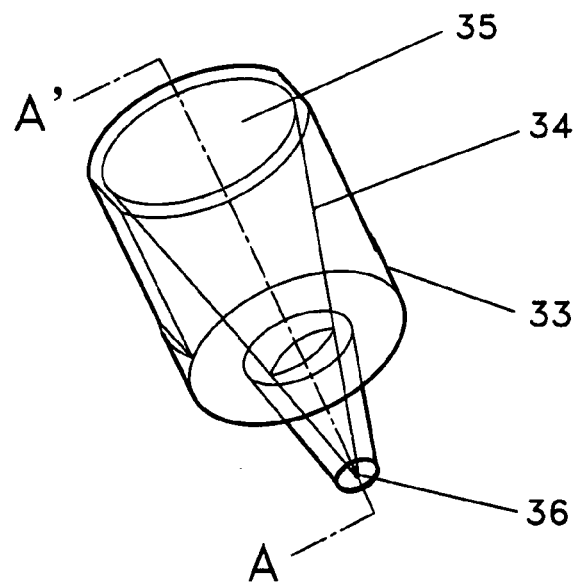
Fig. 17a
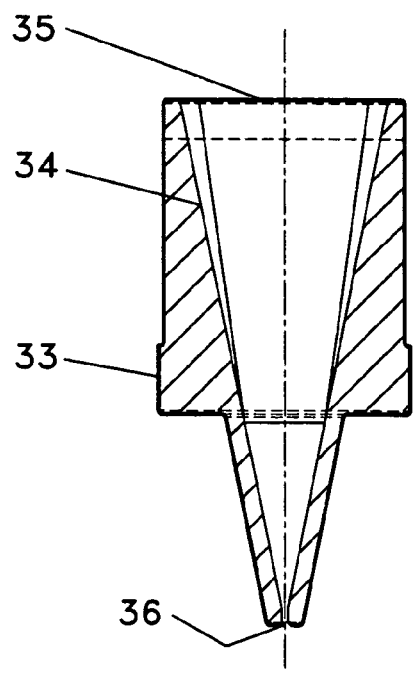
Section A-A'
Fig. 17b
Fig. 17

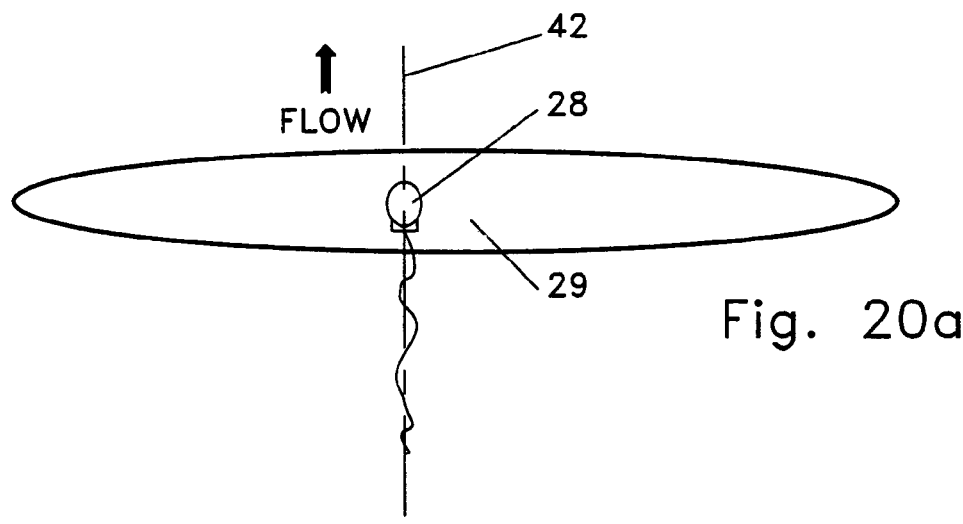
Fig. 20a
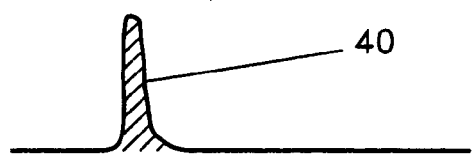
Fig. 20b
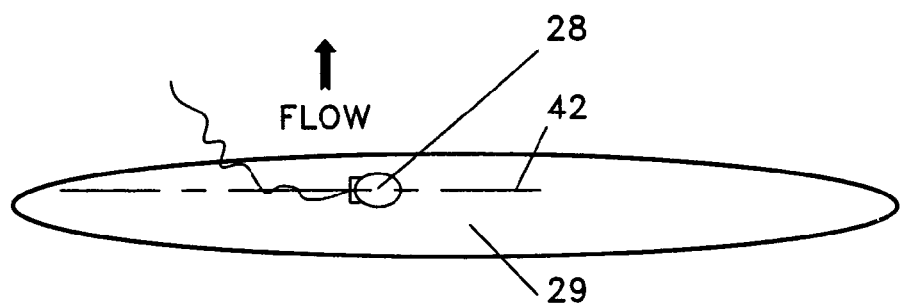
Fig. 20c
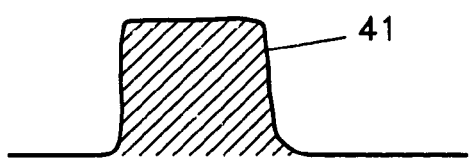
Fig. 20d
Fig. 20

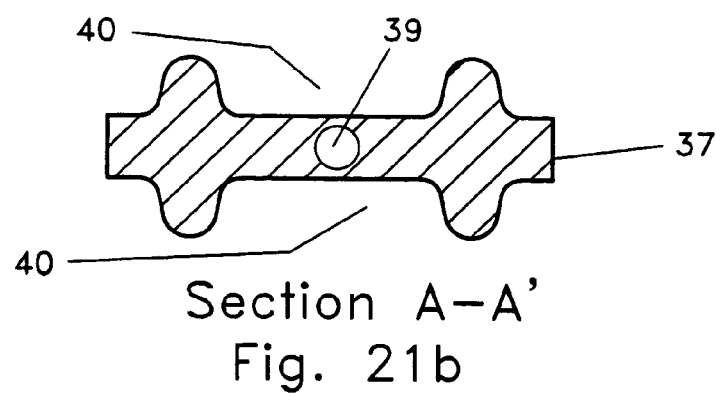
Section A-A'
Fig. 21b
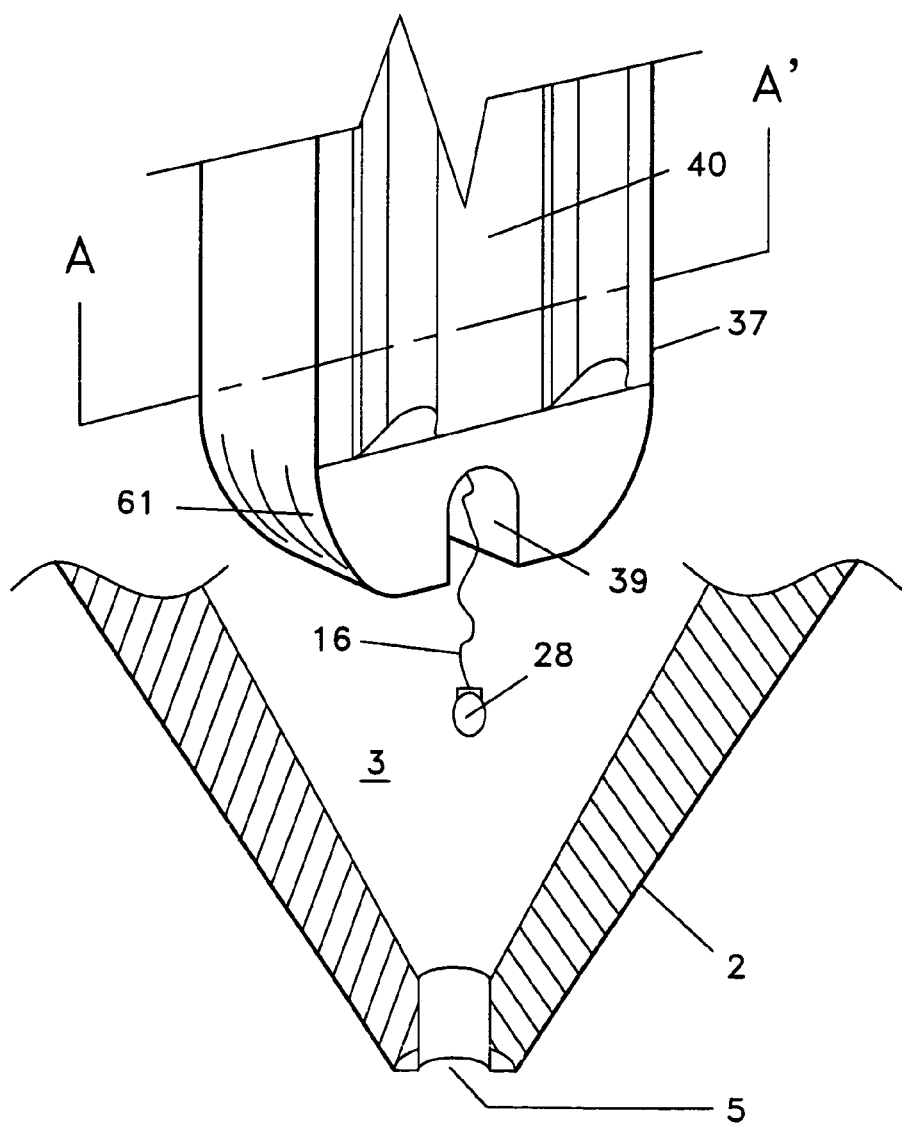
Fig. 21a
Fig. 21

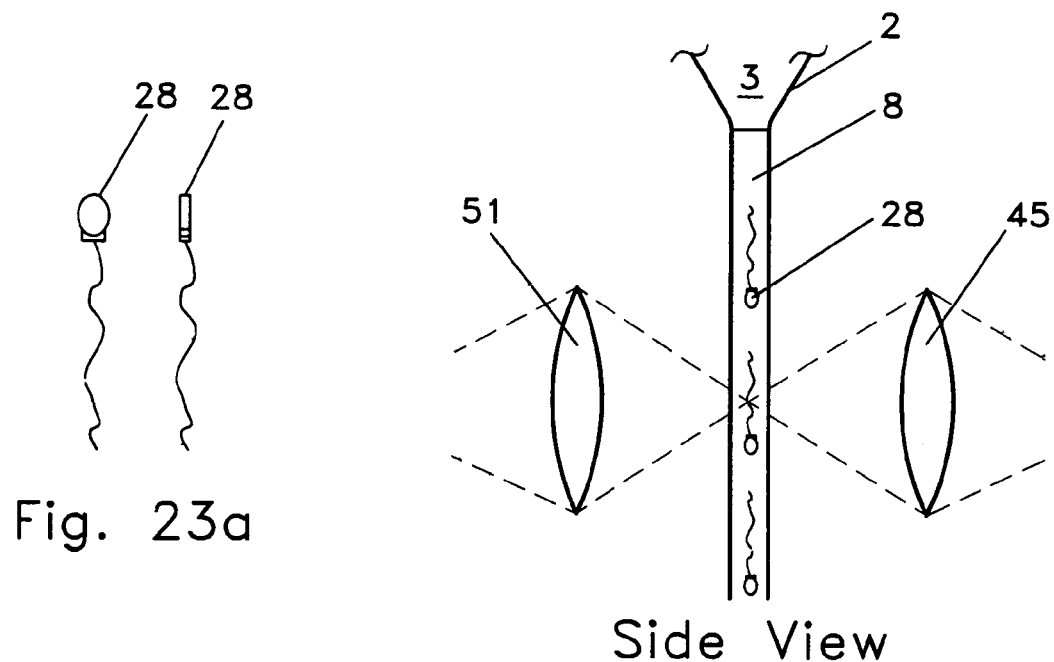
Fig. 23a
Side View
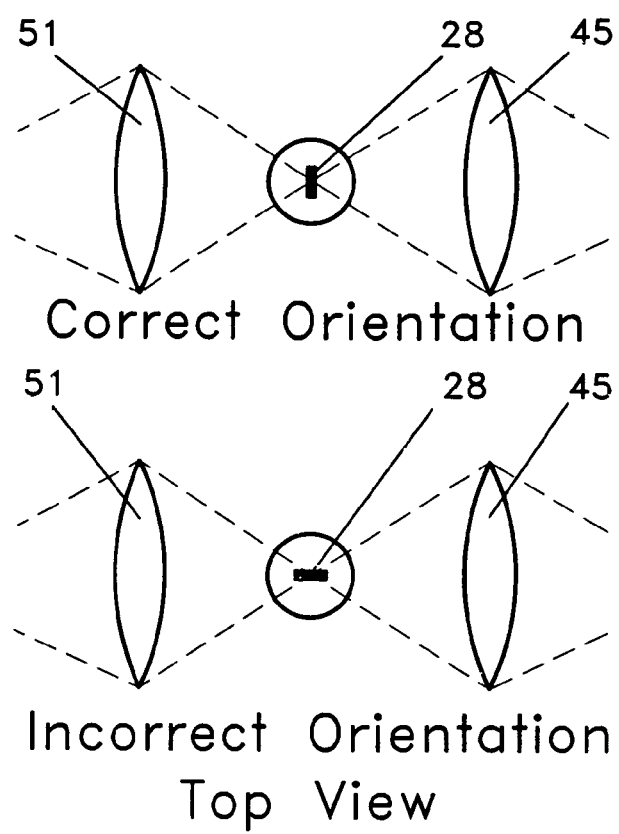
Correct Orientation
Incorrect Orientation
Top View
Fig. 23b
Fig. 23

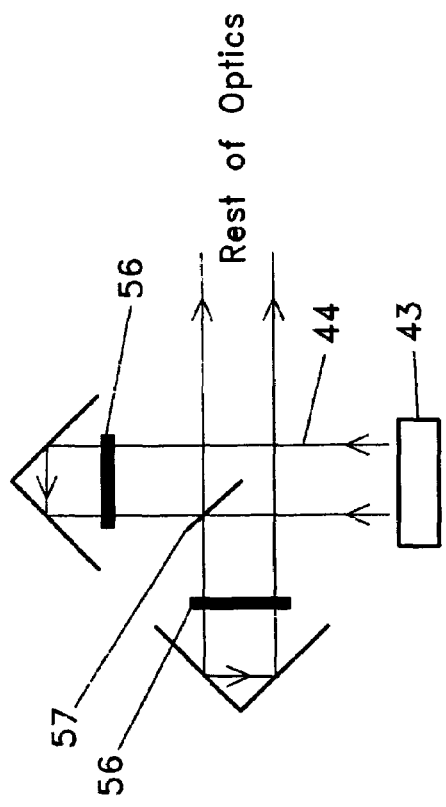
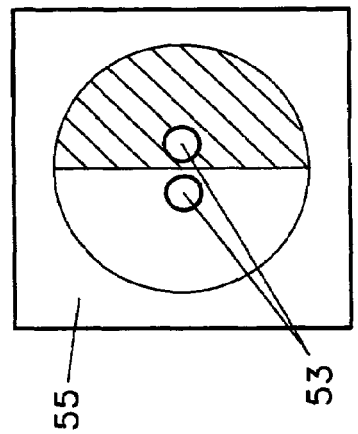
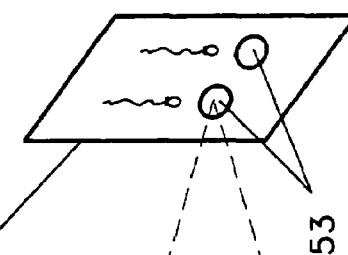
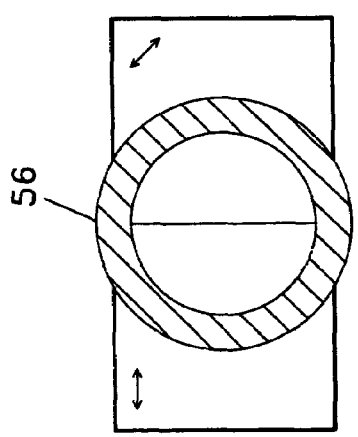
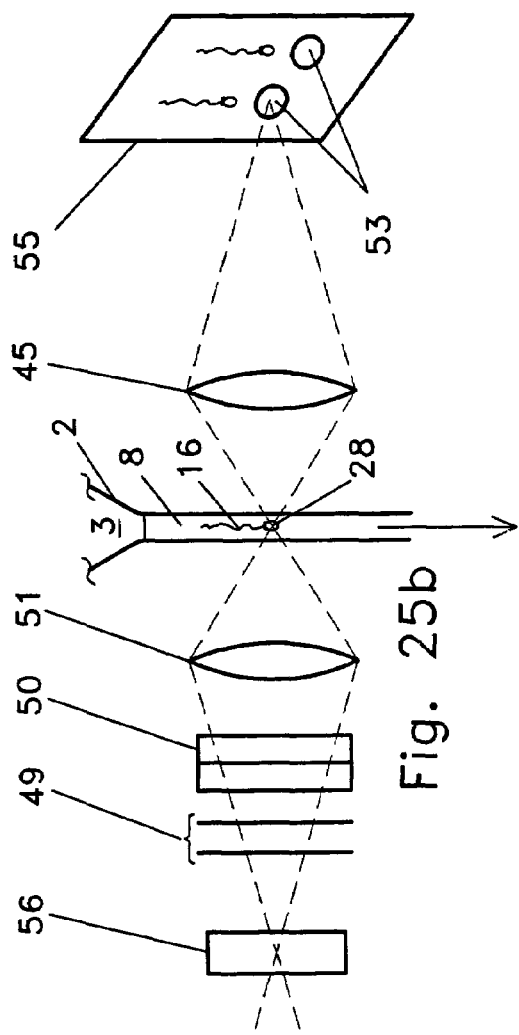
Fig. 25a
Fig. 25b
Fig. 25c
Fig. 25d
Fig. 25

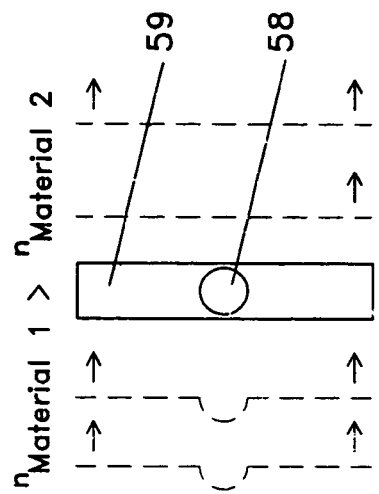
Fig. 26a
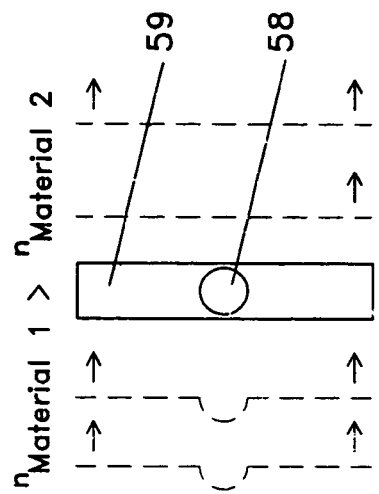
Fig. 26b
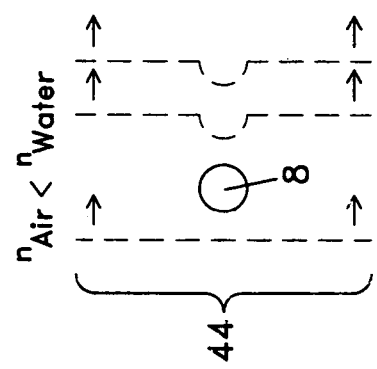
Fig. 26c
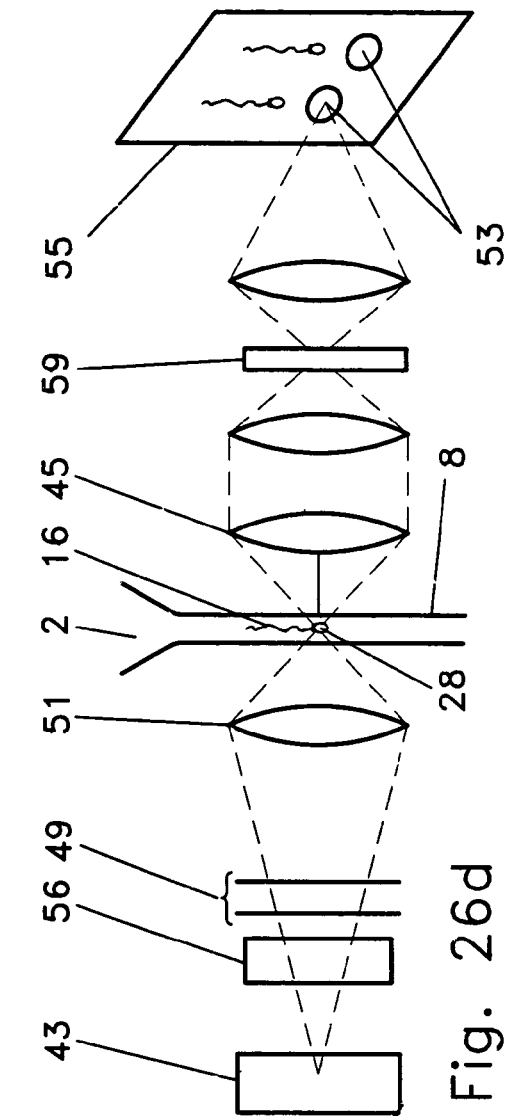
Fig. 26
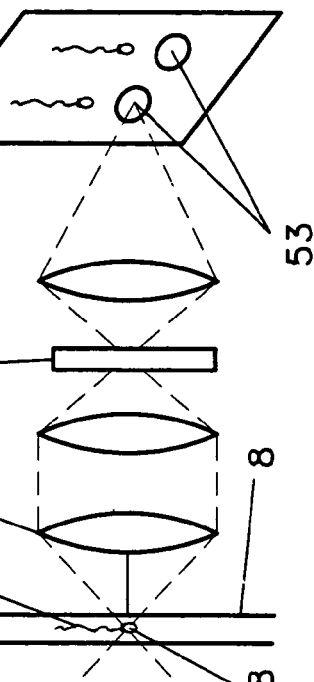
Fig. 26d
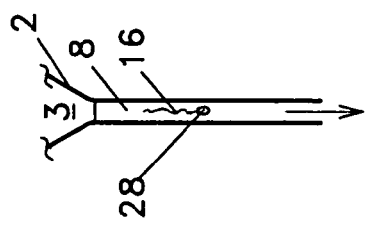

HIGH PURITY X-CHROMOSOME BEARING AND Y-CHROMOSOME BEARING POPULATIONS OF SPERMATOZOA

This application is the U.S. National Stage of International Patent Application No. PCT/US01/15150, filed May 9, 2001, which claims the benefit of U.S. Provisional Patent Application No. 60/203,089 filed 09 May 2000, U.S. Provisional Patent Application No. 60/239,752, filed Oct. 12, 2000, and U.S. Provisional Patent Application No. 60/267,571 filed 10 Feb. 2001, each incorporated by reference.

I. TECHNICAL FIELD

Isolated high purity X-chromosome bearing or Y-chromosome bearing populations of spermatozoa and technologies to isolate spermatozoa, particles, or events based upon differentiation characteristics such as mass, volume, DNA content, or the like.

II. BACKGROUND

Isolated high purity X-chromosome bearing or Y-chromosome bearing populations of spermatozoa can be utilized to accomplish in vitro or in vivo artificial insemination of or fertilization of ova or oocytes of numerous mammals such as bovids, equids, ovids, goats, swine, dogs, cats, camels, elephants, oxen, buffalo, or the like. See also, U.S. Pat. No. 5,135,759, hereby incorporated by reference.

However, conventional technologies for separating spermatozoa into X-chromosome bearing and Y-chromosome bearing populations can result in spermatozoa populations having low purity. Regardless of the separation method spermatozoa have not been routinely separated into X-chromosome bearing and to Y-chromosome bearing sperm samples having high purity, such as 90%, 95%, or greater than 95%.

A number of techniques, directly or indirectly based on differences in size, mass, or density have been disclosed with respect to separating X-chromosome bearing from Y-chromosome bearing spermatozoa As disclosed by U.S. Pat. No. 4,474,875, a buoyant force is applied to all sperm cells simultaneously and X-chromosome bearing and Y-chromosome bearing spermatozoa may then be isolated at different locations in the separation medium. U.S. Pat. No. 5,514,537 discloses a technique whereby spermatozoa traverse a column packed with two sizes of beads. The larger X-chromosome bearing spermatozoa become isolated in the layer containing the larger beads, while the smaller Y-chromosome bearing spermatozoa become isolated in the layer containing the smaller beads. U.S. Pat. No. 4,605,558 discloses that spermatozoa may be made differentially responsive to a density gradient and U.S. Pat. No. 4,009,260 exploits the differences in migration-rate, or swimming-speed, between the Y-bearing spermatozoa, and the X-chromosome bearing spermatozoa, through a column of retarding medium.

A problem common to each of the above-mentioned technologies may be that they each act on all the spermatozoa in a 'bulk-manner', meaning that all the spermatozoa undergo the same treatment at the same time, and the Y-chromosome bearing sperm cells come out faster, earlier, or at a different position than X-chromosome bearing sperm cells. As such, individual sperm cells may not be assessed and there may be no actual 'measurement' of volume, mass, density, or other sperm cell characteristics. One-by-one assessment of sperm cells can provide advantages in that the actual separation process can be monitored, and objective quantitative data can be generated even during the separation process, and separation parameters altered as desired. Furthermore, these technologies may not be coupled with flow cell sorting devices.

Flow cytometer techniques for the separation of spermatozoa have also been disclosed. Using these techniques spermatozoa may be stained with a fluorochrome and made to flow in a narrow stream or band passing by an excitation or irradiation source such as a laser beam. As stained particles or cells pass through the excitation or irradiation source, the fluorochrome emits fluorescent light. The fluorescent light may be collected by an optical lens assembly, focused on a detector, such as a photomultiplier tube which generates and multiplies an electronic signal, which may then be analyzed by an analyzer. The data can then be displayed as multiple or single parameter chromatograms or histograms. The number of cells and fluorescence per cell may be used as coordinates. See U.S. Pat. No. 5,135,759, hereby incorporated by reference. However, with respect to this type of technology a variety of problems remain unresolved and isolating highly purified populations of X-chromosome bearing or Y-chromosome bearing sperm cells be difficult.

A significant problem with conventional flow cytometer technologies can be the orientation of objects, particles, or cells in the sheath fluid stream. This can be particularly problematic when the object or cell is irregular in shape with respect to more than one axis, such spermatozoa for example. One aspect of this problem may be establishing the initial orientation of the object within the sheath fluid stream. A second aspect of this problem may be maintaining the orientation of the object with respect to the detector (photomultiplier tube or otherwise) during the period that emitted light from the object is measured.

Another significant problem with conventional flow cytometer technologies can be the failure to encapsulate the objects or cells in a droplet of liquid. Especially, when droplets are formed around irregularly shaped objects the droplet may not be of sufficient size to completely surround all the features of the objects or cells. For example, during flow cytometry operation as above-described droplets can be formed at very high speed, even as many as 10,000 to 90,000 droplets per second and in some applications as many as 80,000 droplets per second. When spermatozoa are encapsulated into droplets, especially at these high rates of speed, a portion of the tail or neck may not be encapsulated in the droplet. That portion of the tail or neck not encapsulated in the droplet may then be responsive with the nozzle or may be responsive to the environment surrounding the droplet in a manner that interferes with subsequent droplet formation or with proper deflection of the droplet. As a result some of the spermatozoa may not be analyzed at all reducing the efficiency of the procedure, or may not be resolved sufficiently to be assigned to a population, or may be deflected in errant trajectories, or a combination of all may occur.

Another significant problem with conventional flow cytometer technologies, as well as other technologies, can be a coincidence of measurable events. One aspect of this problem can be that the incident light flux from a first event continues to produce signals after the incident light flux from a second event starts to generate a signal. As such, the two events remain at least partially unresolved from one another. Another aspect of this problem can be that two or more events are simultaneously initiated and the incident light flux comprises the contribution of all the events. As such, the multiplicity of events may not be resolved at all and the objects corresponding to the multiplicity of events can be incorrectly assigned to a population or not assigned to a population at all, or both. Specifically, with respect to flow cytometry, individual particles, objects, cells, or spermatozoa in suspension flow through a beam of light with which they interact providing a measurable response, such as fluorescent emission. In conventional flow cytometry, Hoechst stained spermatozoa traverse a laser beam resulting in a fluorescent light emission. The fluorescent light emission from the excited fluorochrome bound to the DNA can be bright enough to produce an electron flow in conventional photomultiplier tubes for a period of time after the actual emission event has ended. Moreover, in a conventional flow cytometer, the laser beam can produce a pattern having a height of 30 µm while the width can be approximately 80 µm. The nucleus of a bovine spermatozoa which contains fluorochrome bound DNA can be about 9 µm in length making the height of the laser beam some three (3) times greater than the nucleus. This difference can allow for the laser excitation of the bound fluorochrome in more than one spermatozoa within the laser beam pattern at one time. Each of these conventional flow cytometry problems decreases the ability to resolve individual events from one another.

Another significant problem with conventional flow cytometer technologies, and other technologies, can be that irregularly shaped objects, such as spermatozoa, generate differing signals (shape, duration, or amount) depending on their orientation within the excitation/detection path. As such, individuals within a homogenous population can generate a broad spectrum of emission characteristics that may overlap with the emission characteristics of individuals from another homogenous population obviating or reducing the ability to resolve the individuals of the two populations.

Another significant problem with conventional flow cytometer technologies, and other technologies, can be that objects are not uniformly exposed to the excitation source. Conventional beam shaping optics may not provide uniform exposure to laser light when the objects are close to the periphery of the beam.

Another significant problem with conventional flow cytometer technologies can be that objects, such as spermatozoa, can be exposed to the excitation source for unnecessarily long periods of time. Irradiation of cells, such as spermatozoa, with laser light may result in damage to the cells or to the DNA contained within them.

Another significant problem with conventional flow cytometer technologies can be that there may be a disruption of the laminar flow within the nozzle by the injection tube. Disruption of the laminar flow can change the orientation of irregularly shaped objects within the flow and lower the speed of sorting and the purity of the sorted populations of X-chromosome bearing sperm or Y-chromosome bearing spermatozoa.

There may be additional problems with technologies that utilize stain bound to the nuclear DNA of sperm cells. First, because the DNA in the nucleus is highly condensed and flat in shape, stoichiometric staining of the DNA may be difficult or impossible. Second, stained nuclei may have a high index of refraction. Third, stain bound to the DNA to form a DNA-stain complex may reduce fertilization rates or the viability of the subsequent embryos. Fourth, the DNA-stain complex is typically irradiated with ultra-violet light to cause the stain to fluoresce. This irradiation may affect the viability of the spermatozoa. Due to these various problems, it may be preferable to use a method that requires less or no stain, or less or no ultra-violet radiation, or less or none of both.

With respect to generating high purity samples of X-chromosome bearing sperm cell or Y-chromosome bearing sperm cell populations (whether live, fixed, viable, non-viable, intact, tailless, or as nuclei), or generally, with respect to detecting small differences in photo-generated signal between serial events having relatively high incident light flux, or with respect to orienting irregularly shaped objects in a fluid stream, or eliminating coincident events within an optical path, or removing undesirably oriented objects from analysis, the instant invention addresses every one of the above-mentioned problems in a practical fashion.

III. DISCLOSURE OF THE INVENTION

A broad object of the invention can be to provide isolated high purity X-chromosome bearing and Y-chromosome bearing populations of spermatozoa. Isolated non-naturally occurring populations of spermatozoa that have high purity have numerous applications including sex selection of offspring from mammals, various in vitro protocols for the fertilization of ova, various in vivo protocols such as artificial insemination, business methods involving the production of prize animals or meat animals, or preservation of rare or endangered animals, to recite but a few of the applications for high purity populations of spermatozoa.

Another broad object of the invention involves both devices and methods for the production of high purity X-chromosome bearing and Y-chromosome bearing sperm samples.

Particular embodiments of the invention are described, which may be used in numerous applications as above-mentioned, that can be used to achieve the specific objects of differentiating between bright photoemissive events having small measurable differences in total light flux, orienting irregularly shaped objects in a fluid stream, the minimization of coincident events within an optical path, the removal of signal contributed by undesired unoriented objects within an optical path (including the removal of the object itself), and the encapsulation of irregularly shaped objects within a droplet. As such, the specific objects of the invention can be quite varied.

Another broad object of the invention can be to provide X-chromosome bearing or Y-chromosome bearing spermatozoa samples (live, fixed, viable, non-viable, intact, tailless, or sperm nuclei) having a graded level of high purity in the range of 80%, 85%, 90%, 95%, or even greater than 95%.

Another significant object of particular embodiments of the invention can be to sort spermatozoa into X-chromosome bearing and Y-chromosome bearing populations having high purity even at high separation rates. The high speed separation can produce live sperm of each sex at rates of about 500, 1000, 2000, 3000, 4000, 5000, 6000, 7000, 8,000, 9,000 or even 10,000 per second, or higher.

Another significant object of particular embodiments of the invention can be to substantially eliminate or remove spermatozoa (live, fixed, viable, non-viable, intact, tailless, or sperm nuclei) having undesired orientation in the excitation/detection portion of the flow path of a flow cytometer.

Another significant object of particular embodiments of the invention can be to provide artificial insemination samples of X-chromosome bearing or Y-chromosome bearing spermatozoa having a high level of purity.

Another significant object of particular embodiments of the invention can be to provide in vitro insemination samples of X-chromosome bearing or Y-chromosome bearing spermatozoa having a high level of purity.

Another significant object of a particular embodiment of the invention can be to preselect the sex of offspring of females inseminated with high purity artificial insemination samples, the sex of offspring of ova fertilized with high purity artificial insemination samples, with selection success rates of 80%, 85%, 90%, 95%, or greater than 95%.

Another significant object of particular embodiments of the invention can be to differentiate between photoemissive events having small differences in total emitted light flux.

Another significant object of particular embodiments of the invention can be to substantially eliminate or reduce the amount of background noise generated by a photomultiplier tube, even in the absence of light, during the period after exposure to high incident light flux.

Another significant object of particular embodiments of the invention can be to substantially eliminate saturation of the photocathode of photomultiplier tube(s) used in conjunction with flow cytometry, or otherwise.

Another significant object of particular embodiments of the invention can be to reduce the number electrons migrating from the photocathode of a photomultiplier tube to the first dynode.

Another significant object of particular embodiments of the invention can be to reduce the total flow of electrons to the N electrode of a photomultiplier tube.

Another significant object of particular embodiments of the invention can be to allow increased light flux to the photocathode of the photomultiplier tube without proportionately increasing the amount of background signal generated by the photomultiplier tube.

Another significant object of particular embodiments of the invention can be to increase the signal to background signal ratio from measured photoemissive events.

Another significant object of particular embodiments of the invention can be to allow increased amplification of the signal generated from the photomultiplier tube during high incident light flux events or serial high incident light flux events without saturating the photocathode of the photomultiplier tube.

Another significant object of particular embodiments of the invention can be to increase the apparent resolution of chromatograms or histograms resulting from sorting fluorochrome stained sperm, or other cells, or other objects, having small differences in emitted light flux upon excitation of the bound fluorochrome(s).

Another significant object of particular embodiments of the invention can be to improve the calibration of sorting flow cytometer instruments when used for sorting spermatozoa.

Another significant object of particular embodiments of the invention can be to increase the sperm sorting rate of flow cytometer systems.

Another significant object of particular embodiments of the invention can be to increase the purity of the sperm samples sorted by flow cytometry.

Another significant object of particular embodiments of the invention can be to provide techniques for the sorting of X-chromosome bearing sperm from Y-chromosome bearing sperm where there is a small difference in the amount of Y chromosome DNA to the amount of X chromosome DNA relative to the total amount of nuclear DNA.

Another significant object of particular embodiments of the invention can be to provide techniques which improve the apparent resolution of histograms generated during the process of sorting X-chromosome bearing sperm from Y-chromosome bearing sperm with a flow cytometer.

Another significant object of particular embodiments of the invention can be to provide beam shaping optics which minimizes coincidence of objects within the excitation/detection path.

Another significant object of particular embodiments of the invention can be to provide beam shaping optics that minimizes the total lumens an object is exposed to traversing the excitation beam. One aspect of this object can be to decrease the total lumens an object is exposed to. A second aspect of this object can be to increase the power of the light source without increasing the total lumens the object is exposed to.

Another significant object of particular embodiments of the invention can be to provide beam shaping optics that allow for uniform exposure of objects that pass through the optical path.

Another significant object of particular embodiments of the invention can be to provide a nozzle that orients irregularly shaped objects in a fluid stream. One aspect this object can be to orient elongated objects in the same direction. A second aspect of this object can be to orient dorso-laterally flatted objects in the same direction.

Another significant object of particular embodiments of the invention can be to fully encapsulate irregularly shaped objects within a drop of fluid.

Another significant object of particular embodiments of the invention can be to differentiate undesirably oriented objects from desirably oriented objects in a fluid stream.

Another object of an embodiment of the invention can be to provide differential interference contrast technology, whereby the object-plane consists of a fluid stream carrying the objects of interest, and whereby the image-plane can be used to measure the signal from the passing objects.

Another object of an embodiment of the invention can be to provide optics that form two laterally separated images from each object in such a way that one can be used to measure the actual volume, and one to determine the orientation. This way, objects that were not orientated properly to allow a accurate measurement of its volume can be discarded. This can be accomplished by modifications so that the light pulses, resulting from these two images can be detected independently using two pinholes in the image plane. Optics are tuned in such a way that a first image can give rise to a light pulse proportional to the volume of the object, and that a second image can give rise to a light pulse dependent on the orientation the object had when it was measured.

Another object of an embodiment of the invention can provide a manner of compensating for the fact that the objects are contained inside a fluid stream. The fluid stream can be a cylinder of water, for example, which acts as a cylindrical lens, thus distorting the image of the object. Optically, this corresponds to cylinder of higher refractive index (water) than its surroundings (air). The compensation disclosed in this invention can consist of, for example, a cylinder having a refractive index lower than its surroundings, although other compensating elements of various shapes and refractive index may also be designed as the need requires. By making sure the light passes through this compensation element, the optical effect of the fluid stream can be compensated by the exactly opposite behavior of the compensation element.

Naturally further objects of the invention are disclosed throughout other areas of the specification and claims.

IV. BRIEF DESCRIPTION OF THE DRAWINGS

FIG. 3 shows a comparison of univariate histograms from flow cytometers (#1, #2, and #3) without the amplifier invention (FIG. 3A) with univariate histograms for the same flow cytometers using a particular embodiment of the amplification invention (FIG. 3B) illustrating the improved resolution between X-chromosome bearing and Y-chromosome bearing populations of bovine spermatozoa.

FIG. 13 shows the laser beam pattern using conventional beam shape optics (FIG. 13A) and the laser beam pattern using the reduced height beam shape optics (FIG. 133B).

FIG. 14 shows a bar graph that compares the purity of separated X-chromosome bearing spermatozoa (FIG. 14A) and Y-chromosome bearing spermatozoa (FIG. 14B) using conventional technology or using the amplification invention independently or in conjunction with reduced height beam shaping optics.

FIG. 17 shows a perspective and one cross section of the object orienting nozzle invention.

FIG. 20 illustrates the removal of undesired unoriented spermatozoa (RUUS) invention by comparison of signal(s) from the oriented spermatozoa (FIGS. 20A and 20B) and the signal(s) from the unoriented spermatozoa (FIGS. 20C and 20D).

FIG. 21 shows a perspective of another embodiment of the beveled injection tube invention having a paddle shaped beveled blade.

FIG. 23A shows the shape and size of a typical spermatozoon and FIG. 23B shows the difference between correctly and non-correctly orientated spermatozoa.

FIGS. 25A and B shows an embodiment of the invention having two halves with a pinhole corresponding to each half, FIG. 25C shows an image plane of an embodiment of the invention, FIG. 25D shows an embodiment of the invention having two independently rotatable polarizers.

FIGS. 26A and 26B illustrates the compensation method for the fluid stream for an embodiment of the invention, FIG. 26C shows an embodiment of a compensation element, 26D shows another embodiment of a compensation element where images of a fluid stream and from the compensation element fall on top of each other in the image plane.

Figure 27:
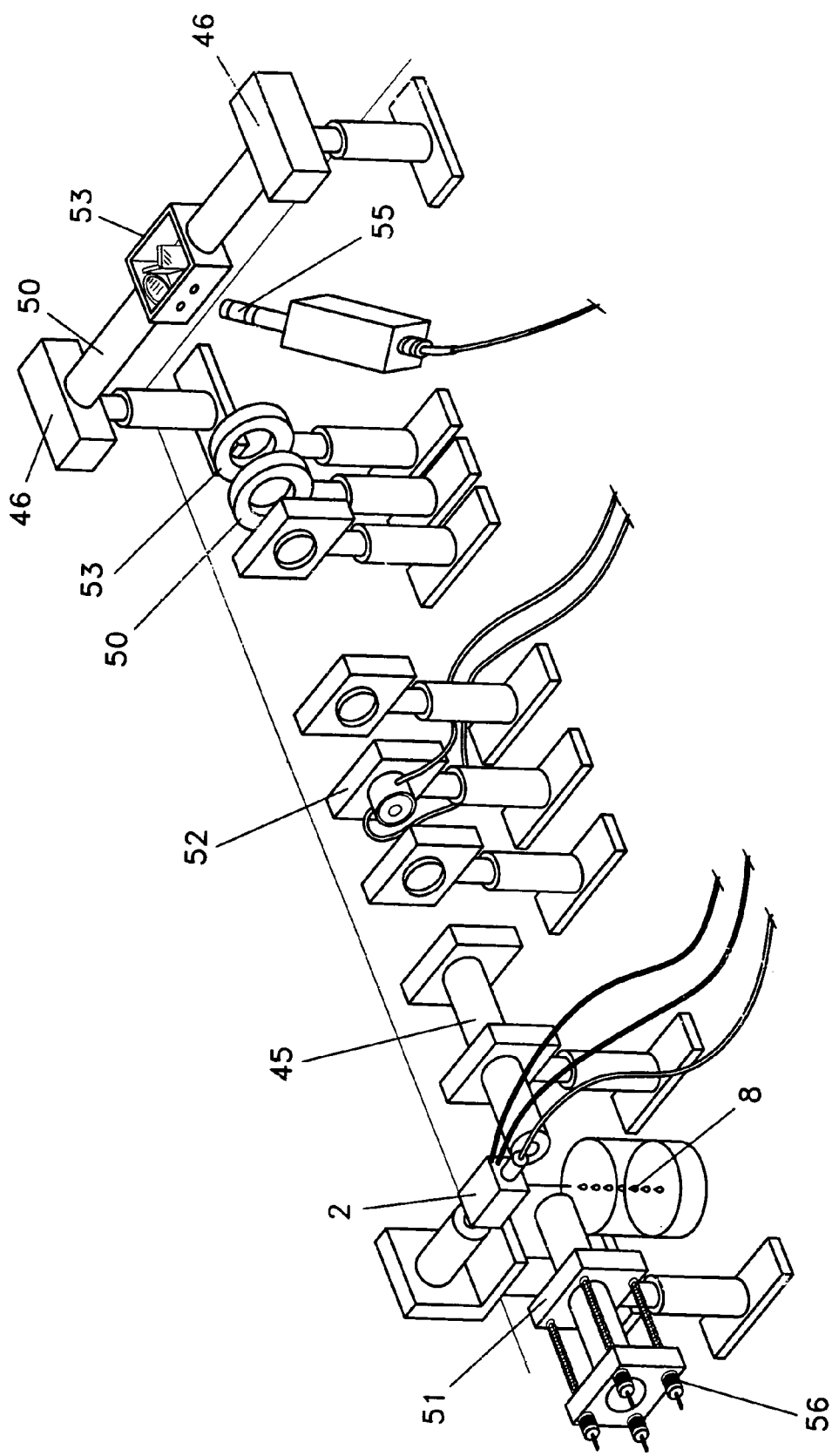

FIG. 27 shows an embodiment of the interference optics invention.

Figure 28:
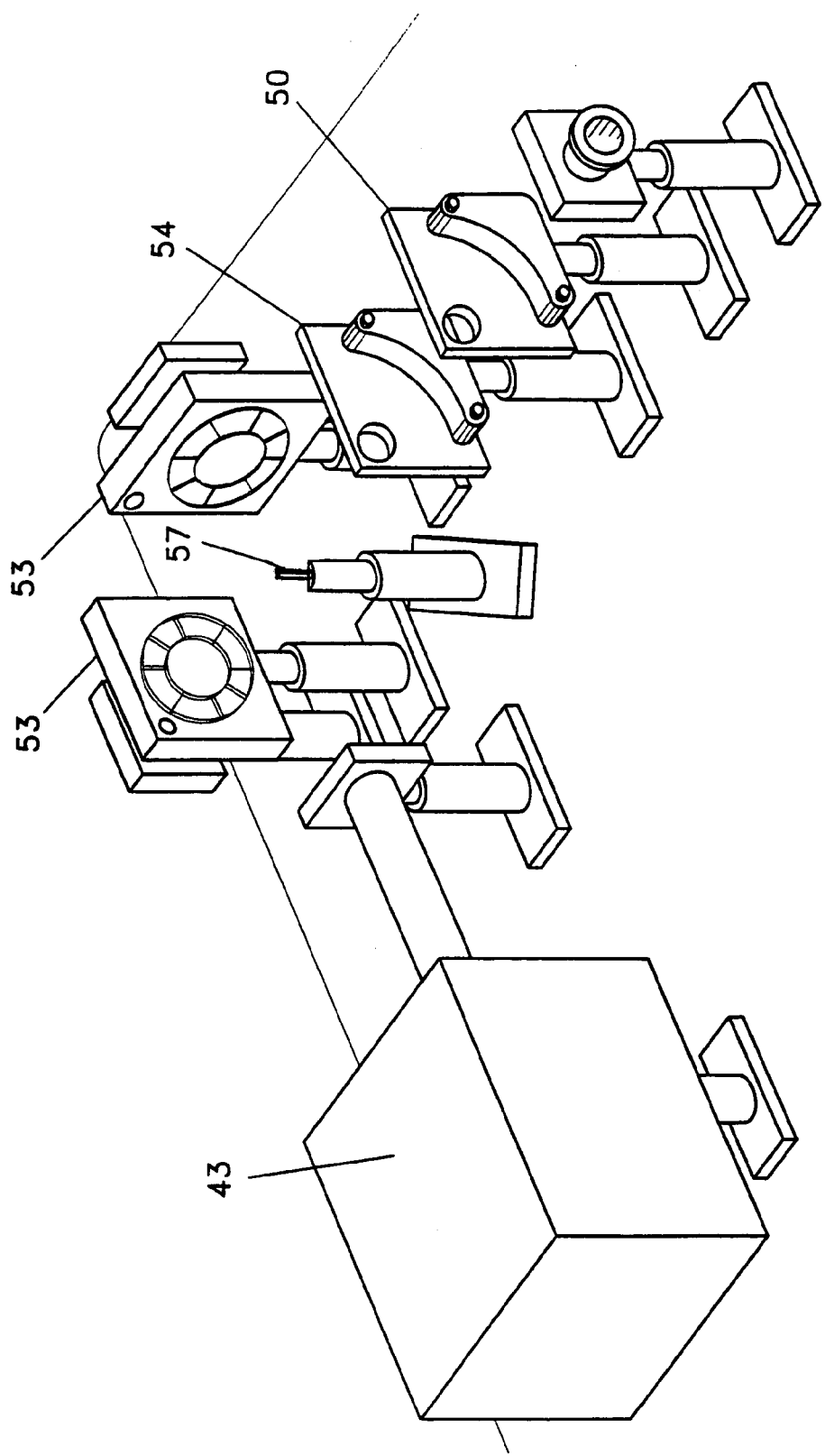

FIG. 28 shows an a second view of the interference optics invention.

V. MODE(S) FOR CARRYING OUT THE INVENTION

The invention involves isolated high purity X-chromosome bearing and Y-chromosome bearing populations of spermatozoa or sperm cells. High purity X-chromosome bearing and Y-chromosome bearing populations of spermatozoa can comprise populations of intact live spermatozoa, and may also comprise populations of tailless spermatozoa (sperm nuclei), or populations of other viable or non-viable forms of spermatozoa, as may be desired. While particular examples are provided that describe the invention in the context of separating intact live sperm cells each having a sperm cell head, necks, and tail, it should be understood that the technologies described can have various applications with respect to sperm nuclei as well. X-chromosome bearing and Y-chromosome bearing populations of spermatozoa should further be understood to encompass spermatozoa from any male of a species of mammal including, but not limited to, spermatozoa from humans and spermatozoa from commonly known animals such as bovids, equids, ovids, canids, felids, goats, or swine, as well as less commonly known animals such as elephants, zebra, camels, or kudu. This list of animals is intended to be exemplary of the great variety of animals from which spermatozoa can be routinely sorted at 90% or greater purity, and is not intended to limit the description of the invention to the spermatozoa from any particular species of mammals.

High purity separated spermatozoa from the various species of mammals can be incorporated into products that can be used with artificial insemination protocols or as part of commercial business methods such as those as described in U.S. patent application Nos. 60/211,093, 60/224,050, or Patent Cooperation Treaty Application No. US99/17165; or be used with low dose insemination protocols as described in Patent Cooperation Treaty Application No. US98/27909, or used in vitro fertilization of oocytes from animals, including humans, as described in U.S. patent application No. 60/253,785, each of the above-mentioned references are hereby incorporated by reference.

The use of the term purity or high purity should be understood to be the percent of the isolated spermatozoa population bearing a particular differentiating characteristic or desired combination of characteristics. For example, where a population of spermatozoa are separated based upon bearing an X-chromosome as opposed to a Y-chromosome, a X-chromosome bearing population having 90% purity comprises a population of spermatozoa of which 90% of the individual spermatozoa bear an X-chromosome while 10% of such population of spermatozoa may bear a Y-chromosome. As such, high purity with respect to X-chromosome bearing populations or Y-chromosome bearing populations can comprise a purity selected from the group consisting of between 90% to about 100%, between about 91% to about 100%, between about 92% to about 100%, between about 93% to about 100%, between about 94% to about 100%, between about 95% to about 100%, between about 96% to about 100%, between about 97% to about 100%, between about 98% to about 100%, between about 99% to about 100%.

Importantly, while numerous embodiments of the invention describe isolated high purity X-chromosome and Y-chromosome bearing populations of spermatozoa, and while the description further discloses high purity spermatozoa separation devices and methods of how to isolate and how to use isolated high purity populations of spermatozoa, the basic concepts of the invention should be understood to be applicable to other types of particles or events having particle differentiation characteristics or event differentiation characteristics. It should be understood that the invention can be applicable to a variety of circumstances in which resolving small differences in photogenerated signal may be necessary, such as product defect detection, field flow fractionation, liquid chromatography, electrophoresis, computer tomography, gamma cameras, time of flight instruments, or the like as would be readily understood by those skilled in those arts.

Moreover, while this disclosure provides descriptions of embodiments of apparatus and methods for flow separation of X-chromosome bearing spermatozoa from Y-chromosome bearing spermatozoa, the description of these embodiments of the invention is not meant to reduce the scope of the invention to only flow separation of spermatozoa or only to high purity flow cytometer spermatozoa separation systems but rather these examples are intended to exemplify the basic concepts of the invention in a practical manner so that they may be applied to the wide variety of applications.

Figure 1:
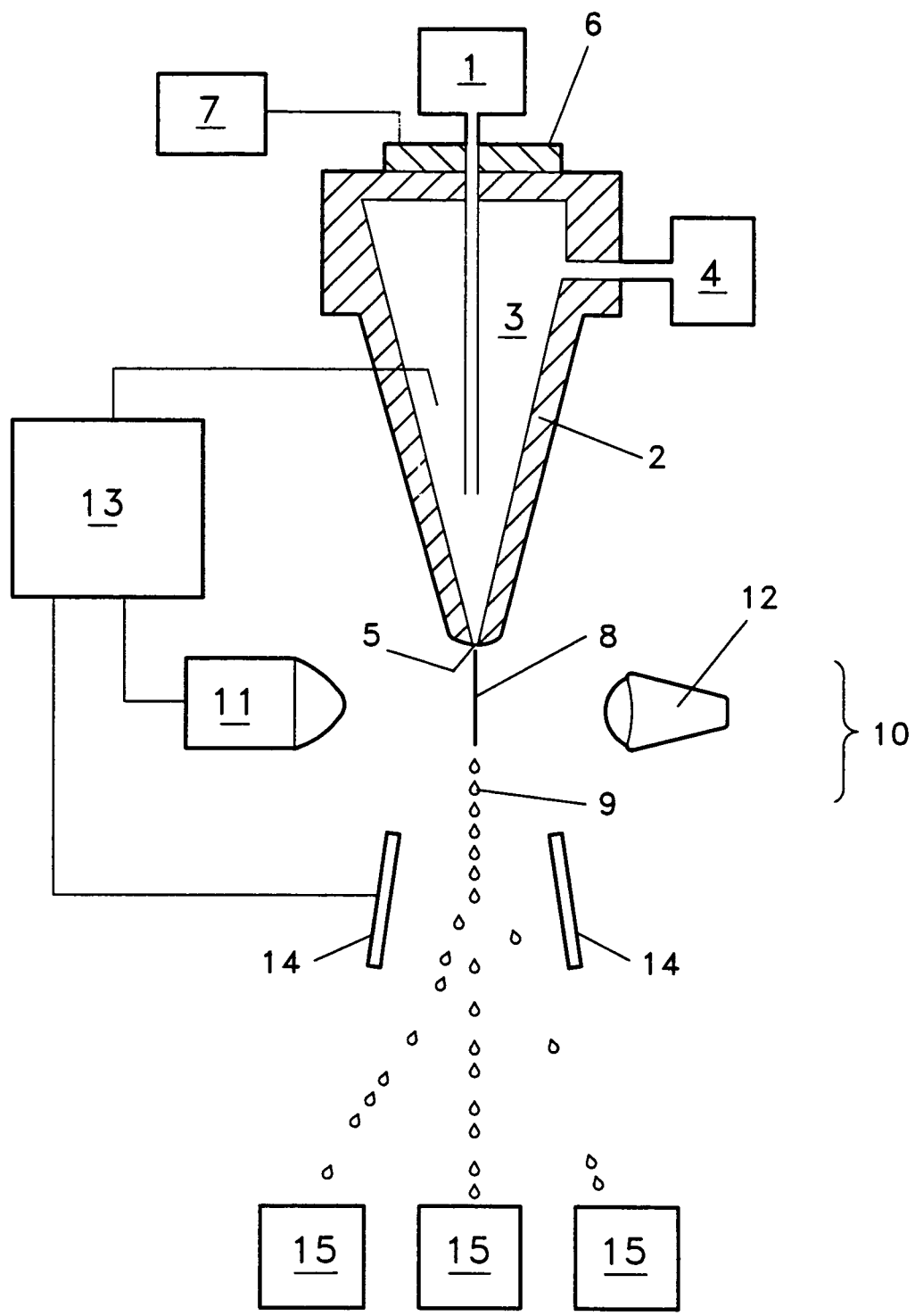
FIG. 1 shows a generalized flow cytometer.
Figure 2:
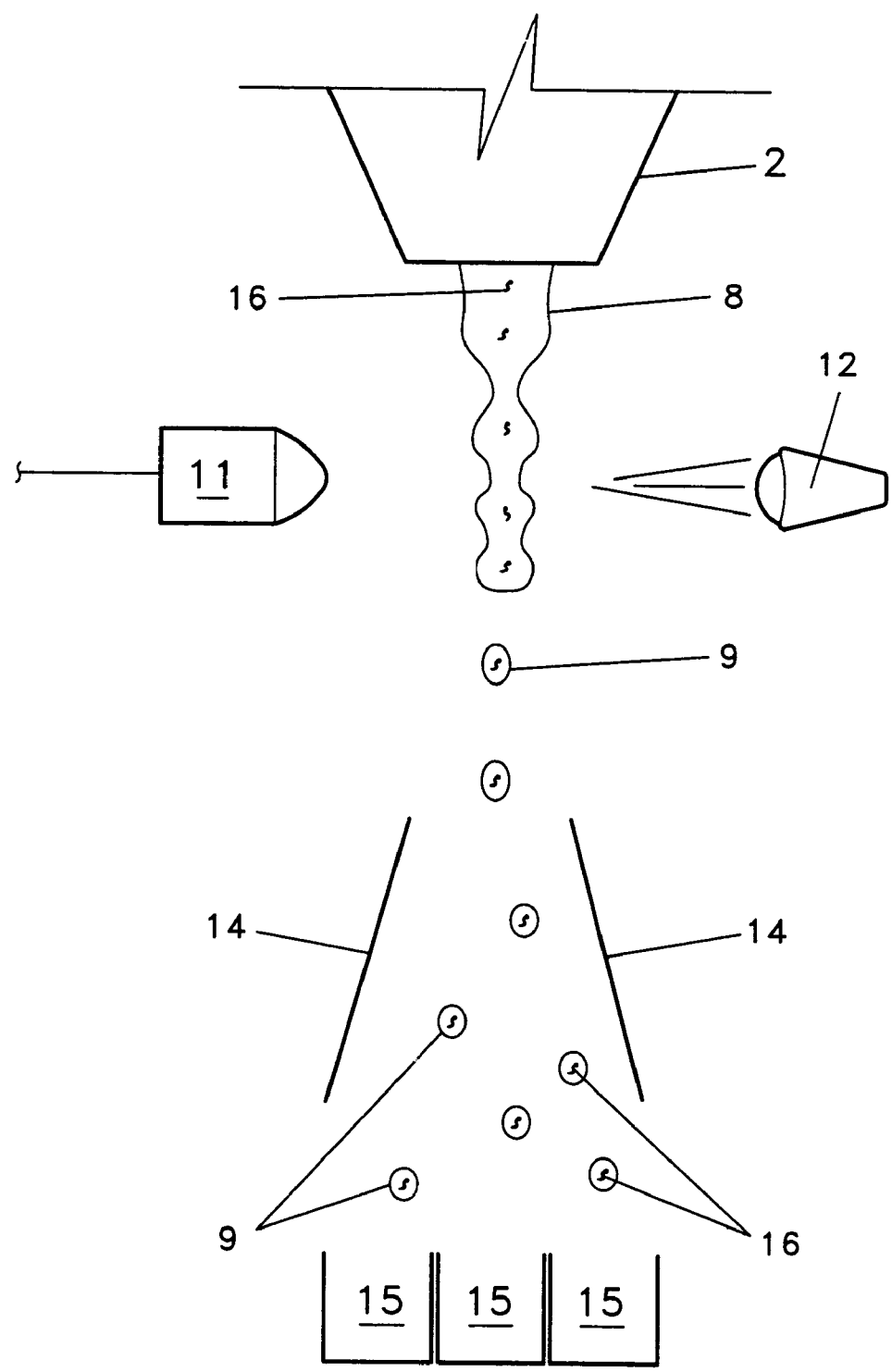
FIG. 2 shows a second view of a generalized flow cytometer.

Now referring to FIGS. 1 and 2, a flow cytometer embodiment of the invention is shown which includes a particle or cell source (1) which acts to establish or supply particles or cells stained with at least one fluorochrome for analysis. The particles or cells are deposited within a nozzle (2) in a manner such that the particles or cells are introduced into a fluid stream or sheath fluid (3). The sheath fluid (3) is usually supplied by some sheath fluid source (4) so that as the particle or cell source (1) supplies the particles or cells into the sheath fluid (4) they are concurrently fed through the nozzle (2).

In this manner it can be easily understood how the sheath fluid (3) forms a sheath fluid environment for the particles or cells. Since the various fluids are provided to the flow cytometer at some pressure, they flow out of nozzle (2) and exit at the nozzle orifice (5). By providing some type of oscillator (6) which may be very precisely controlled through an oscillator control (7), pressure waves may be established within the nozzle (2) and transmitted to the fluids exiting the nozzle (2) at nozzle orifice (5). Since the oscillator (6) acts upon the sheath fluid (3), the stream (8) exiting the nozzle orifice (5) eventually and regularly forms drops (9). Because the particles or cells are surrounded by the fluid stream or sheath fluid environment, the drops (9) may entrain within them individually isolated particles or cells, and can be sperm cells with respect to some embodiments of the invention.

Since the drops (9) can entrain particles or cells, the flow cytometer can be used to separate particles, cells, sperm cells or the like based upon particle or cell characteristics. This is accomplished through a particle or cell sensing system (10). The particle or cell sensing system involves at least some type of detector or sensor (11) which responds to the particles or cells contained within fluid stream (8). The particle or cell sensing system (10) may cause an action depending upon the relative presence or relative absence of a characteristic, such as fluorochrome bound to the particle or cell or the DNA within the cell that may be excited by an irradiation source such as a laser exciter (12) generating an irradiation beam to which the particle can be responsive. While each type of particle, cell, or the nuclear DNA of sperm cells may be stained with at least one type of fluorochrome different amounts of fluorochrome bind to each individual particle or cell based on the number of binding sites available to the particular type of fluorochrome used. With respect to spermatozoa, the availability of binding sites for Hoechst 33342 stain is dependant upon the amount of DNA contained within each spermatozoa. Because X-chromosome bearing spermatozoa contain more DNA than Y-chromosome bearing spermatozoa, the X-chromosome bearing spermatozoa can bind a greater amount of fluorochrome than Y-chromosome bearing spermatozoa. Thus, by measuring the fluorescence emitted by the bound fluorochrome upon excitation, it is possible to differentiate between X-bearing spermatozoa and Y-bearing spermatozoa.

In order to achieve separation and isolation based upon particle or cell characteristics, emitted light can be received by sensor (11) and fed to some type of separation discrimination system or analyzer (13) coupled to a droplet charger which differentially charges each droplet (9) based upon the characteristics of the particle or cell contained within that droplet (9). In this manner the separation discrimination system or analyzer (13) acts to permit the electrostatic deflection plates (14) to deflect drops (9) based on whether or not they contain the appropriate particle or cell.

As a result, the flow cytometer acts to separate the particle or cells (16) by causing them to be directed to one or more collection containers (15). For example, when the analyzer differentiates sperm cells based upon a sperm cell characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus is collected in an undeflected stream into a suction tube or the like as discussed in U.S. patent application Ser. No. 09/001,394, hereby incorporated by reference herein. Naturally, numerous deflection trajectories can be established and collected simultaneously.

To routinely separate particles, cells, sperm cells, or spermatozoa (intact, live, fixed, viable, non-viable, or nuclei) into high purity X-chromosome bearing and Y-chromosome bearing populations, the particle differentiation apparatus or methods used must provide high resolution of the differentiation characteristics that are used as the basis of analysis and separation.

With respect to spermatozoa, differentiating between the light emitted by the fluorochrome bound to the nuclear DNA of X-chromosome bearing sperm cells and the light emitted by the fluorochrome bound to the nuclear DNA of Y-chromosome bearing sperm cells may be difficult as discussed above.

In many applications, the total emitted light from photoemissive events incident to the detector, which can be a photomultiplier tube, can be high while the difference between the emitted light of each photoemissive events to be differentiated can be small. The problem can be exacerbated when the photoemissive events happen serially at high rate of speed and the time period between photoemissive events is short, such as with high speed cell sorting using flow cytometers. When separating particles, cells, or sperm cells based upon the difference in bound fluorochrome the cells flow past an excitation source and a high number of emissive events per second can be established. As a result, the amount of emitted light generated in the stream of particles, cells, or sperm cells, can be enormous. As the speed of the stream is increased, the intercept point with the excitation source becomes very bright. This high level of incident light upon the photocathode of the photomultiplier tube can cause a very low signal to background signal ratio. The amount of background signal can be further exacerbated when fluorochrome such as Hoechst 33342 can be used to label the nuclear DNA of sperm cells.

Most solutions to the problem have focused on decreasing the total amount of light flux upon the photocathode tube by placing optical filters in front of the photomultiplier tube. This approach does not change the proportion of signal to background signal and subsequent attempts to increase the sensitivity of the photomultiplier tube generates additional background signal as the photomultiplier tube saturates from the amount of background signal.

Typically, photomultiplier tubes have an operation voltage range of about 400 volts to about 900 volts. The lower limit of linear operation of standard photomultiplier tubes, such as the R928 and R1477 photomultiplier tubes available from Hamamatsu Corporation, may be about 300 volts. As such, equipment or instruments which employ photomultiplier tubes are configured to operate such photomultiplier tubes at or above 400 volts. Even where reduction of the number of electrons at the anode is desired, as disclosed in U.S. Pat. Nos. 4,501,366 and 5,880,457 the voltage between the photocathode and the first dynode is maintained at a high voltage and reduction of the electrons at the anode is accomplished by either decreasing the voltage to the remaining dynodes, or the inherent dark noise or shot noise is filtered out electronically.

Unexpectedly, reducing the amount of voltage to the photomultiplier tube below 400 volts to about 280 volts, or about 250 volts, or even to just above 0 volts can allow small differences in photoemissive light to be differentiated even when the total light emitted from each photoemissive event is high, or even when there are a high number of bright serial events per second. With respect to the rate of photoemissive events generated from the irradiation of fluorochromes bound to the nuclear DNA of spermatozoa, the invention allows the rate of photoemissive events that can be achieved during separation of spermatozoa into X-chromosome bearing and Y-chromosome bearing populations to be increased to a separable event rate of at least 5000 separable events per second, at least 6000 separable events per second, at least 7000 separable events per second, at least 8000 separable events per second, at least 9000 separable events per second, at least 10,000 separable events per second, at least 11,000 separable events per second, at least 12,000 separable events per second, at least 13,000 separable events per second, at least 14,000 separable events per second, at least 15,000 separable events per second, at least 16,000 separable events per second, at least 17,000 separable events per second, at least 18,000 separable events per second, at least 19,000 separable events per second, at least 20,000 separable events per second, at least 25,000 separable events per second, at least 30,000 separable events per second, and at least 35,000 separable events per second, or greater.

As a specific example, existing Cytomation SX MoFlo® sorting flow cytometers are configured to operate the photomultiplier tube at 400 volts minimum. The gain can be adjusted to operate the photomultiplier tube at higher voltages but not lower voltages. SX MoFlo® flow cytometers can be converted by reconfiguring the photomultiplier controllers. The R16C resistor (2.49 kilohms) on channel three can be replaced by a 2.0K resistor to alter the gain of the amplifier that controls the photomultiplier tube. This conversion allowed the photomultiplier tube to be operated at about 280 volts. Similar conversion of SX MoFlo® flow cytometers with two 3.75 kilohm resistors in parallel, or a 1.3 kilohm resistors can allow the photomultiplier tube to be operated at voltages of about 200 volts, or just above zero volts, respectively. Also with respect to this conversion, the neutral density filter in front of the photocathode can also be removed as a result of operating the photomultiplier tube outside of the typical operation voltage range.

This conversion unexpectedly increases the signal to noise ratio of the photoemissive event as it is translated to an electronic signal by the photomultiplier tube. The cleaner signal may then be amplified by increasing the gain amplifier to the analog to digital converter of the analyzer (13) to the appropriate level and output may be generated as univariate or bivariate histograms.

Now referring to FIG. 3, a comparison of univariate histograms generated on three different SX MoFlo® flow cytometers (#1, #2, #3) prior to the use of the invention (FIG. 1A), and using the invention (FIG. 1B) with respect to the separation of intact live ejaculated bovine sperm are shown. As can be understood from the univariate histograms, the resolution (the apparent differentiation of the X-chromosome bearing population from the Y-chromosome bearing population represented by the valley between peaks) of intact live X-chromosome bearing spermatozoa (17) from live Y-chromosome bearing spermatozoa (18) can be substantially improved by use of the invention.

The mean separation rate or sort rates of intact live spermatozoa prior to use of this embodiment of the invention with the SX MoFlo® flow cytometers was about $17.9 \times 10^6/4.5$ hours of both X-chromosome bearing spermatozoa and Y-chromosome bearing spermatozoa (i.e. about 1,100 separations or sorts per second in each of two streams—the first stream X-chromosome bearing spermatozoa and the second stream Y-chromosome bearing spermatozoa) at about 87% purity with a range of 84% to 93% purity. The separable event rate was 22,000, 23,000, and 20,000 respectively for the three sorts.

The mean sort rates of live spermatozoa after the above-mentioned conversion was about $40.3 \times 10^6/4.5$ hour sort (i.e. about 2,500 sorts per second per stream) at about 90.8% purity with a range of 89% to about 92%. The events per second were 13,000, 15,000, and 19,500 respectively for the three sorts.

As can be understood from the data not only did this embodiment of the invention result in increased purity of the separated spermatozoa populations but also allowed the separation rate or sort rate to be more than doubled while the separable events rate was actually decreased.

Figure 4:
FIG. 4 shows univariate and bivariate histograms illustrating the conventional resolution between X-chromosome bearing and Y-chromosome bearing populations of bovine spermatozoa.
Figure 4:
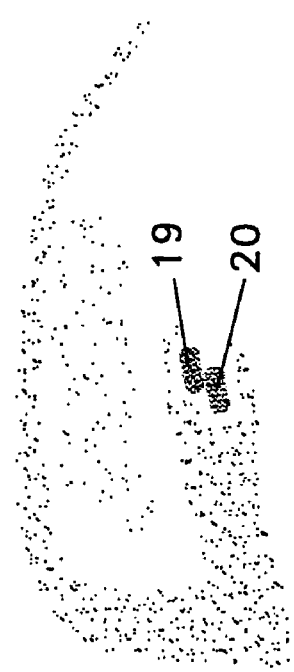
Figure 5:
FIG. 5 shows univariate and bivariate histograms illustrating improved resolution between X-chromosome bearing and Y-chromosome bearing populations of bovine spermatozoa using a particular embodiment of the amplification invention.
Figure 5:
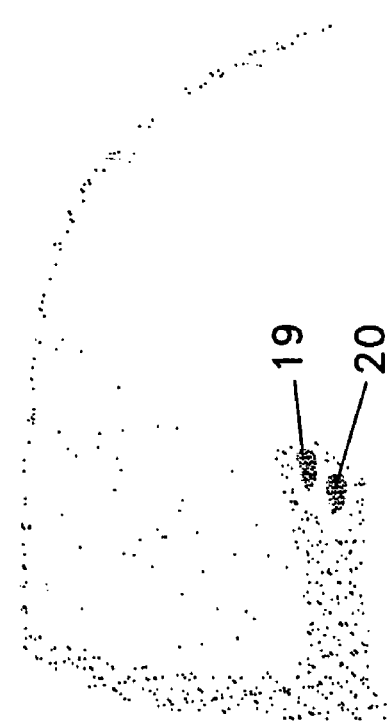

Similarly, referring now to FIGS. 4 and 5, which show bivariate histograms from sorting of intact live bull spermatozoa with the SX MoFlo® flow cytometer #1 prior to using the invention (FIG. 4) and after the above-mentioned conversion (FIG. 5). Prior to using the invention, the SX MoFlo® flow cytometer was initially operated at 440 volts at the photocathode with the laser adjusted to 135 MW, a gain of 1× and with a neutral density filter of 1.0 (1/10th amplitude) at about 10,000 events per second. Upon using the invention, the SX MoFlo® flow cytometer was operated at about 262 volts at the photocathode, with the laser adjusted to about 100 mW, a gain of 4×, without the neutral density filter, at about 10,000 separable events per second. As can be understood from this data there is a large increase in resolution as evidenced by the increased depth of the valley between the X-chromosome bearing population (19) and the Y-chromosome bearing population (20).

Figure 6:
FIG. 6 shows a second example of univariate and bivariate histograms illustrating the conventional resolution between X-chromosome bearing and Y-chromosome bearing populations of bovine spermatozoa.
Figure 6:
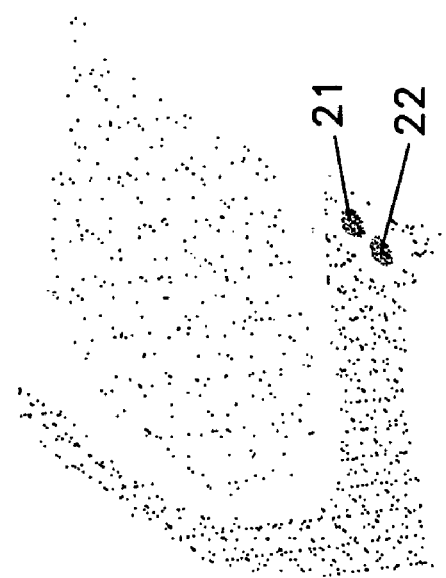
Figure 7:
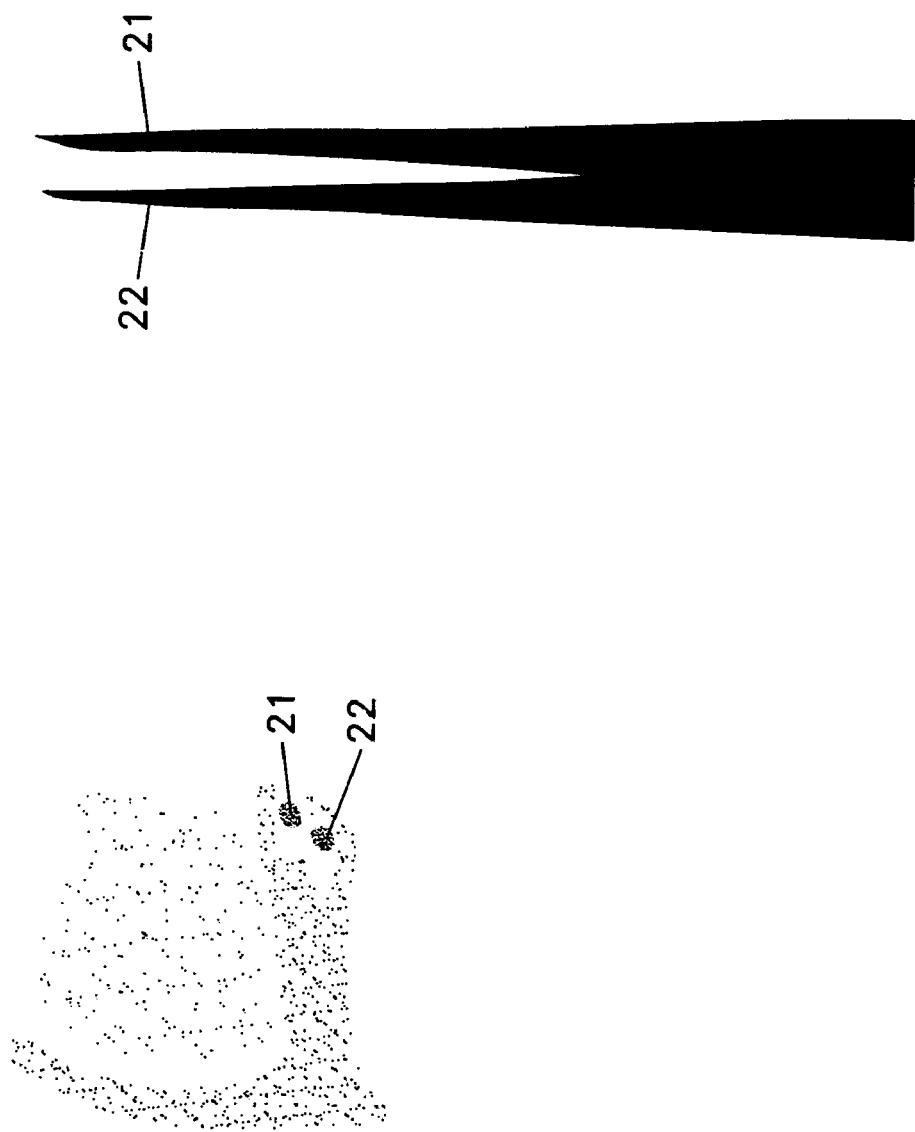
FIG. 7 shows a second example of univariate and bivariate histograms illustrating the improved resolution between X-chromosome bearing and Y-chromosome bearing populations of bovine spermatozoa using a particular embodiment of the amplification invention.

Similarly, referring now to FIGS. 6 and 7, which show bivariate histograms from sorting of intact live bull spermatozoa with the SX MoFlo® flow cytometer #2 before using this embodiment of the invention (FIG. 6) and upon using this embodiment of the invention (FIG. 7) operated at the same parameters as shown in FIGS. 3 and 4 respectively. Again, there can be a large increase in resolution as evidenced by the depth of the valley between the X-chromosome bearing population (21) and the Y-chromosome bearing population (22).

Figure 8:
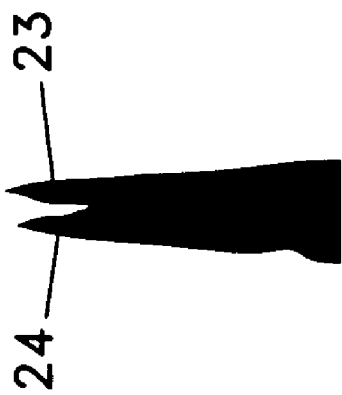
FIG. 8 shows univariate and bivariate histograms illustrating the conventional resolution between X-chromosome bearing and Y-chromosome bearing populations of equine spermatozoa.
Figure 8:
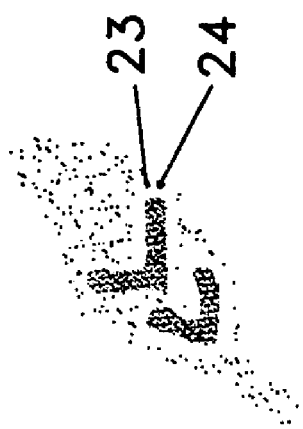
Figure 9:
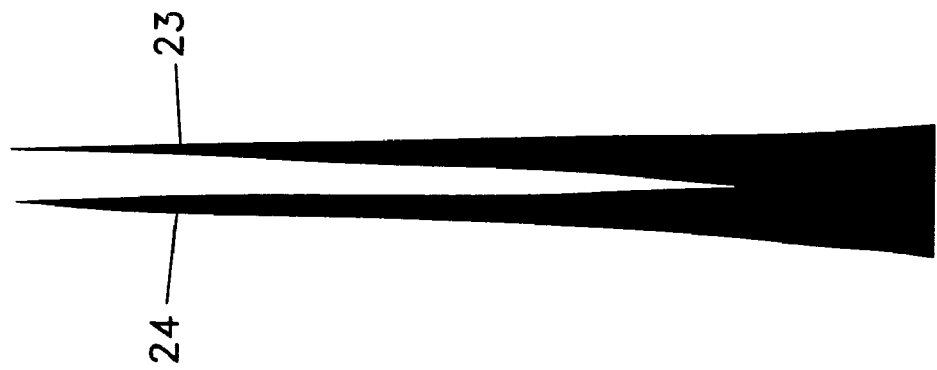
FIG. 9 shows univariate and bivariate histograms illustrating the improved resolution between X-chromosome bearing and Y-chromosome bearing populations of equine spermatozoa using a particular embodiment of the amplification invention.
Figure 9:
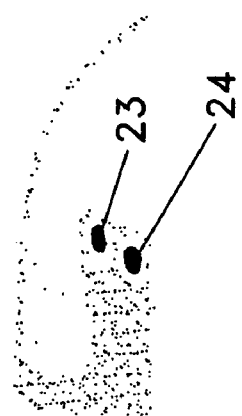

Now referring to FIGS. 8 and 9, which show bivariate histograms from separation or sorting of intact live equine spermatozoa with the SX MoFlo® flow cytometer before using this embodiment of the invention (FIG. 8) and upon using this embodiment of the invention (FIG. 9). When using this embodiment of the invention, live equine spermatozoa were separated or sorted with the laser power at 100 mW with the photomultiplier tube voltage below 300 volts. The separation rates or sort rates exceeded 4,800 sorts per second average at 12,000 events per second. The increased resolution of the X-chromosome bearing population (23) and the Y-chromosome bearing population (24) is dramatic. The data shows that about 8 to about 9 channels separation can be achieved with this embodiment of the invention as compared to 5 channels of separation between the peaks without the use of this embodiment of the invention. The purity of both the sorted X-chromosome bearing population and the sorted Y-chromosome bearing population was about 93%.

Figure 10:
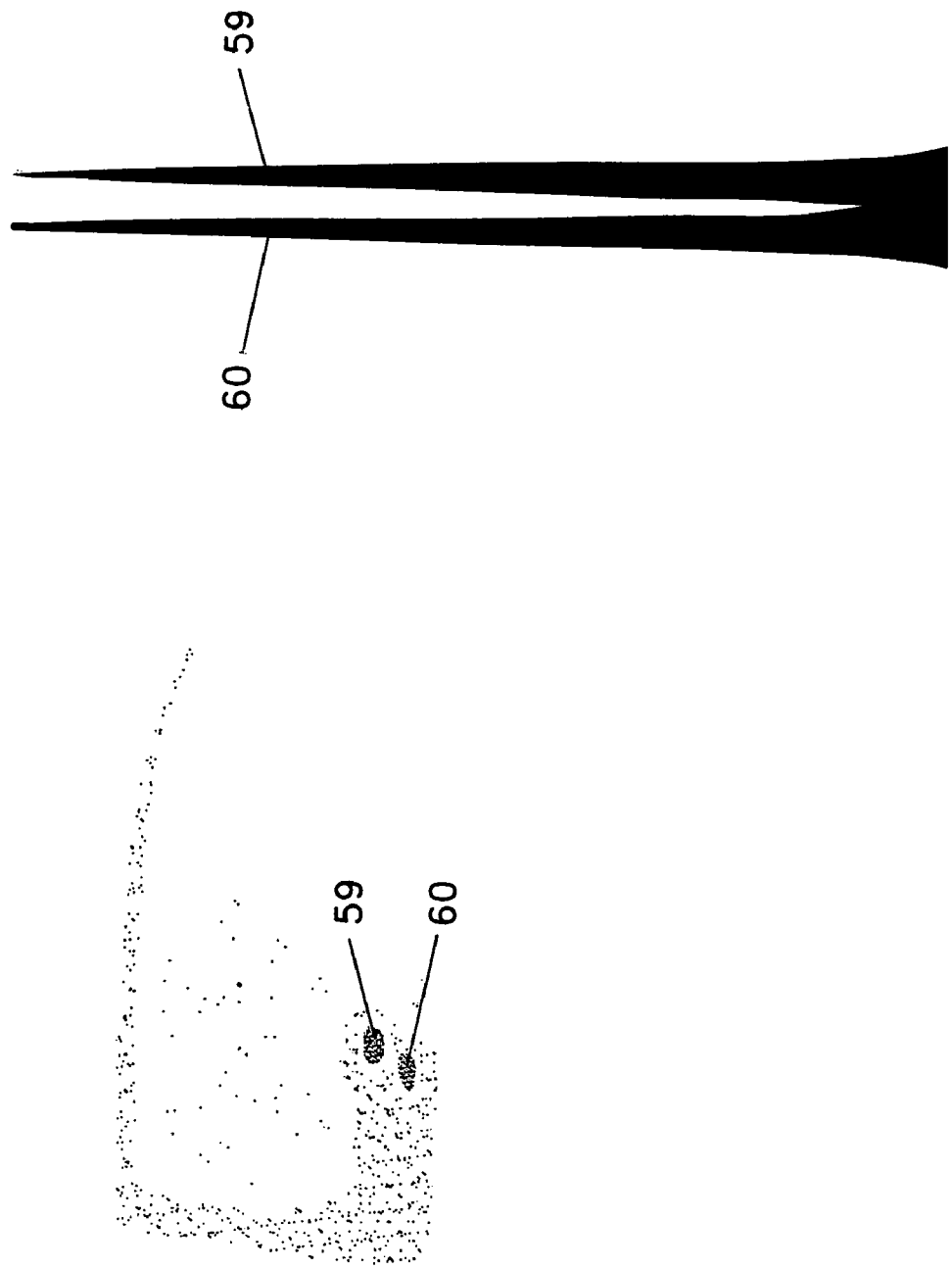
FIG. 10 shows univariate and bivariate histograms illustrating the improved resolution between X-chromosome bearing and Y-chromosome bearing populations of equine spermatozoa nuclei using a particular embodiment of the amplification invention.

Now referring to FIG. 10, which shows a univariate histogram and a bivariate dot plot from sorting of Hoechst 33342 stained stallion sperm nuclei (S-05400) separated using this embodiment of the invention. The nuclei were prepared from freshly ejaculated stallion sperm. The sperm were washed by centrifugation, sonicated and the resultant heads and tails separated using Percoll density gradient centrifugation. the isolated heads were washed, fixed with 2% formalin and then stained with Hoechst 33342. The stained nuclei were stabilized using sodium azide (0.5%). The sample was run at 5000 events per second to produce the histograms. The stained nuclei were then used to calibrate an SX MoFlo® flow cytometer was converted as above-mentioned to incorporate the photomultiplier tube embodiment of the invention. Compensation was used to level the two populations (X stained nuclei and Y stained nuclei) in the bivariate plot. Note that the two populations of equine sperm nuclei are nearly fully resolved to baseline as shown by the univariate plot.

Figure 11:
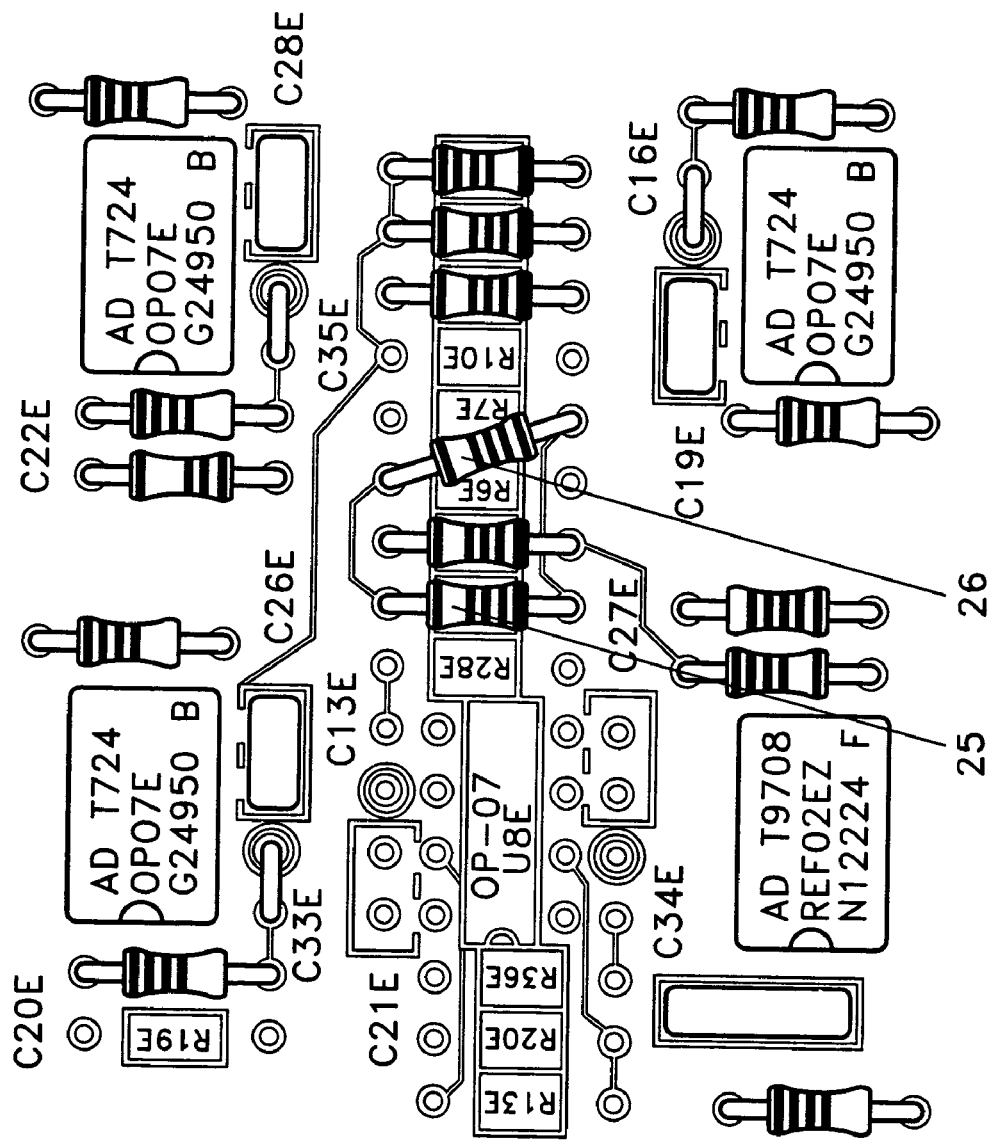
FIG. 11 shows a particular embodiment of the circuit board modification to make the amplification invention with respect to a MoFlo® flow cytometer.
Figure 12:
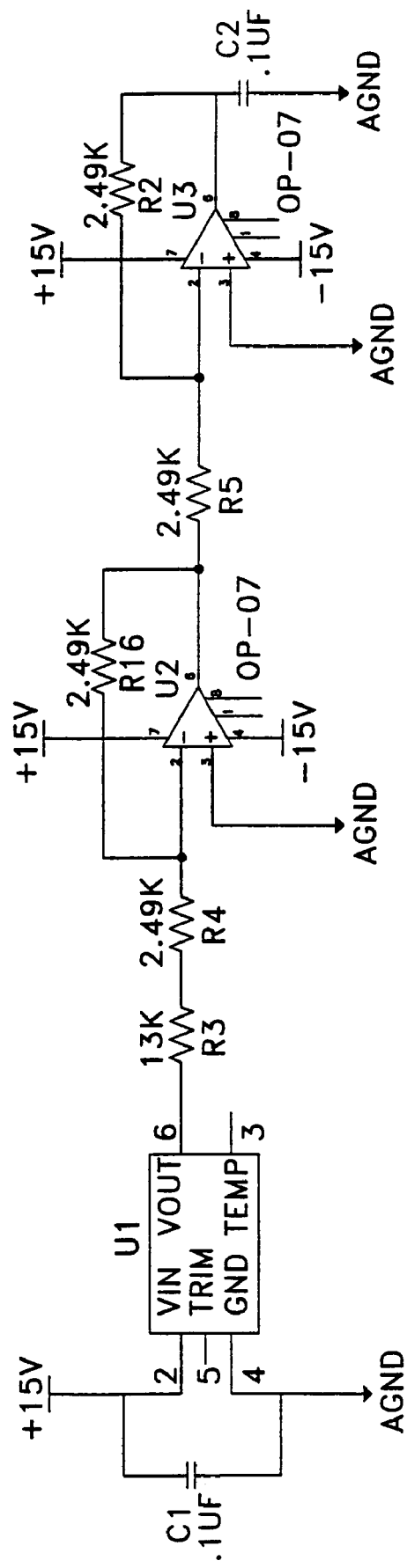
FIG. 12 shows an electrical schematic diagram of a particular embodiment of the amplification invention with respect to a MoFlo® flow cytometer.

Now referring to FIG. 11, a modification specifically for SX MoFlo® flow cytometer includes the use of two resistors in parallel to provide the correct value of 1.8K. Two 3.57K resistors (25) and (26) are equal to about 1.785K which can be sufficiently close to the value to be effective. With this modification the photomultiplier tube on this particular instrument can then be run at about 200 volts. Naturally, a similar modification can be made to other flow cytometer instruments or other instruments which use a photomultiplier tube to measure the amount of light emitted from particular events. FIG. 12, provides a electrical schematic diagram for this particular embodiment of the invention.

Another important embodiment of the invention can be a reduced height irradiation beam pattern optics. As shown by FIG. 13A, conventional irradiation beam shaping optics generate a beam pattern (27) that can have a height can be greater than much greater than the height of the sperm cell head(s) (28) passing through it. As a result, more than a single sperm cell head containing fluorochrome bound DNA can enter the irradiation beam pattern at the same time. In that case, the fluorochrome(s) bound to the DNAs contained within the multiple sperm heads can be excited simultaneously and fluoresce within a single emissive event. As such, the prior or subsequent emissive event can include coincident light flux contributed from other sperm head(s) in the beam pattern (27). This results in a reduced difference in mean light flux between light emissive events which distinguish between X-chromosome bearing spermatozoa and Y-chromosome bearing spermatozoa. It can also decrease the difference in mean light flux between events that compare light emissions of X-chromosome bearing spermatozoa or Y-chromosome bearing spermatozoa. Importantly, coincident excitation of fluorochrome bound to multiple DNAs increases the mean brightness of the events making the measurable difference in light flux between events an even smaller percentage of the total light flux emitted. This makes quantification of the differences between events even more difficult.

By reducing the height of the beam shape as shown by FIG. 13B, the coincidence of multiple sperm heads being within the reduced height beam (29) pattern during the same measured event is reduced. This results in an increased mean difference between light emissive events which distinguish between X-chromosome bearing spermatozoa and Y-chromosome bearing spermatozoa. It can also reduce the mean total light flux for each measured emissive event. For particular embodiments of the invention used for sorting bovine sperm which have a nucleus of about 9 µm, it has been found that the height of the beam can be about 20 µm. In this application, it has been found that vertical beam heights of less than 20 µm did not provide an additional gain in resolution.

Referring to FIG. 14, it can be understood that the use of reduced height irradiation beam pattern optics can improve the purity of sorted populations of X-chromosome bearing bovine spermatozoa (FIG. 14A) and sorted populations of Y-chromosome bearing bovine sperm (FIG. 14B) that have been stained with Hoechst 33342 stain. This is true for both 25% and 40% sort gates of the univariate peak. As can be further understood from FIG. 14, the reduced height beam pattern optics can improve purity of separated spermatozoa independent of any other aspect of the invention, such as modification of photomultiplier circuitry embodiment of the invention (new PMT) as described above, or can be used in conjunction with the modified photomultiplier embodiment of the invention to increase the purity of separated spermatozoa samples even further.

Another advantage of the reduced height beam pattern optics can be that the transit time of the spermatozoa in the excitation laser beam or irradiation beam can be reduced. A reduced amount of irradiation time within the excitation laser beam may result in less stress or damage to the spermatozoa.

Again referring to FIG. 14B, it can be understood that the reduced height beam pattern can be used in conjunction with a irradiation beam pattern having greater area than conventionally used. For example, conventional beam patterns (27), such as that shown in FIG. 14A, have an elliptical pattern of about 30 um×80 um while the invention when used for sorting bovine sperm generates optimal resolution between X-chromosome bearing and Y-chromosome bearing populations when the beam has a 20 um×160 um beam pattern (29). The 20 um×160 um beam pattern has approximately 1.3 times the area of the 30 um×80 um beam pattern. As such, there can be an inverse proportion in loss of energy at the incident point. This makes it possible to increase the excitation laser power without concern for increasing the irradiation damage to the spermatozoa. For example, if an instrument has conventional beam shaping optics that produce a 30 um×80 um irradiation beam pattern and the excitation laser is conventionally powered at 150 mW, then particular embodiments of the invention with a 20 um×160 um beam pattern can have an excitation laser powered at 300 mW without increasing the total amount of power at the incident point. Alternately, the excitation laser can be run at 150 mW to take advantage of the lower per unit area irradiation energy, decreased irradiation damage, longer laser life, and the like.

In comparison to conventional beam shaping optics and conventional photomultiplier tube amplification devices, the reduced height beam pattern optics invention and the photomultiplier tube amplification invention can increase the purity of X-chromosome bearing and Y-chromosome bearing populations of spermatozoa by about 4%, or more.

Figure 15:
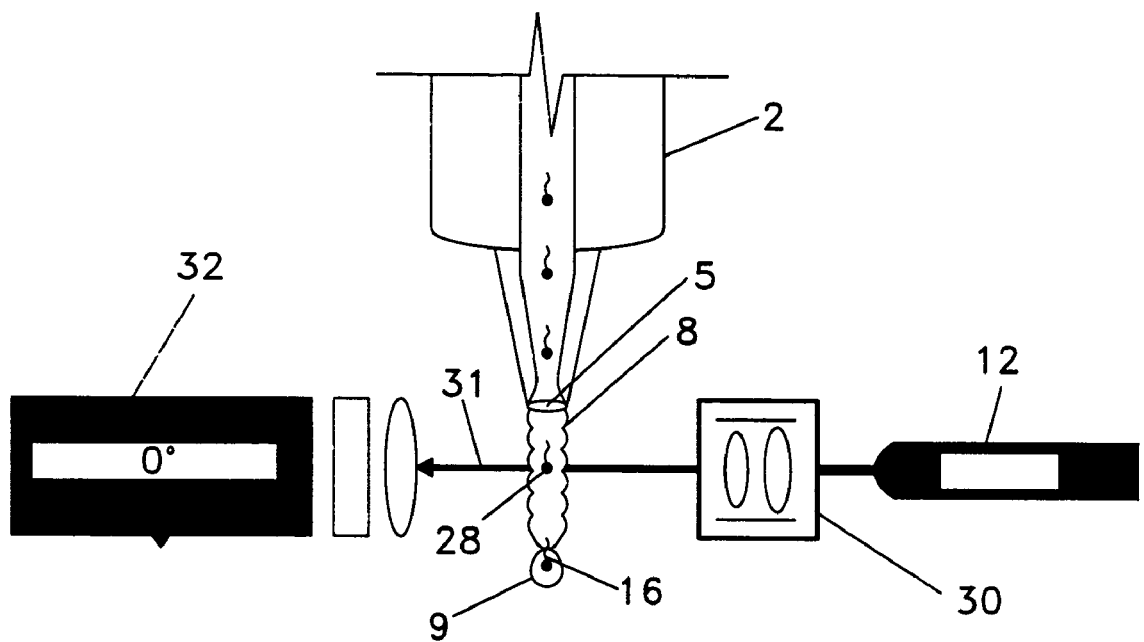
FIG. 15 shows a front view of the reduced height beam shaping optics.
Figure 16:
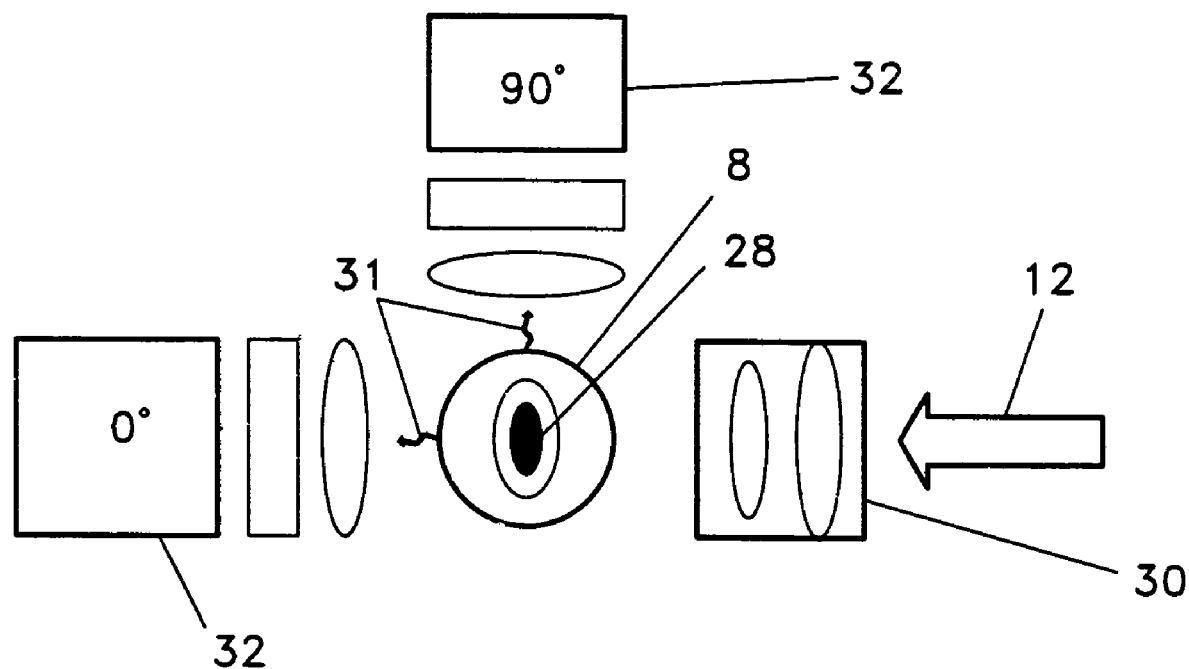
FIG. 16 shows a top view of the reduced height beam shaping optics.

The beam shaping optics invention (30) can be installed to a flow cytometer as shown in FIGS. 15 and 16. As can be understood, the light emitted (31) by laser excitation of fluorochrome(s) bound to the DNA contained within spermatozoa can be detected by photomultiplier tubes (32) situated at 0 and 90 degrees relative to the flat surface of the sperm head (28) as it flows through the excitation laser beam pattern.

As can be understood, stained spermatozoa must be pumped through the excitation beam or irradiation beam in a precise manner so that each sperm head is oriented with the flat surface of the sperm head directed toward the photomultiplier tube that is the 0 degree detector. Accurate measurement of the DNA content of the spermatozoa can only be measured from the flat surface of the paddle-shaped sperm head (28). Thus, only that proportion of the spermatozoa that enter the excitation beam in the proper orientation can be measured accurately and sorted based upon DNA content.

Figure 18:
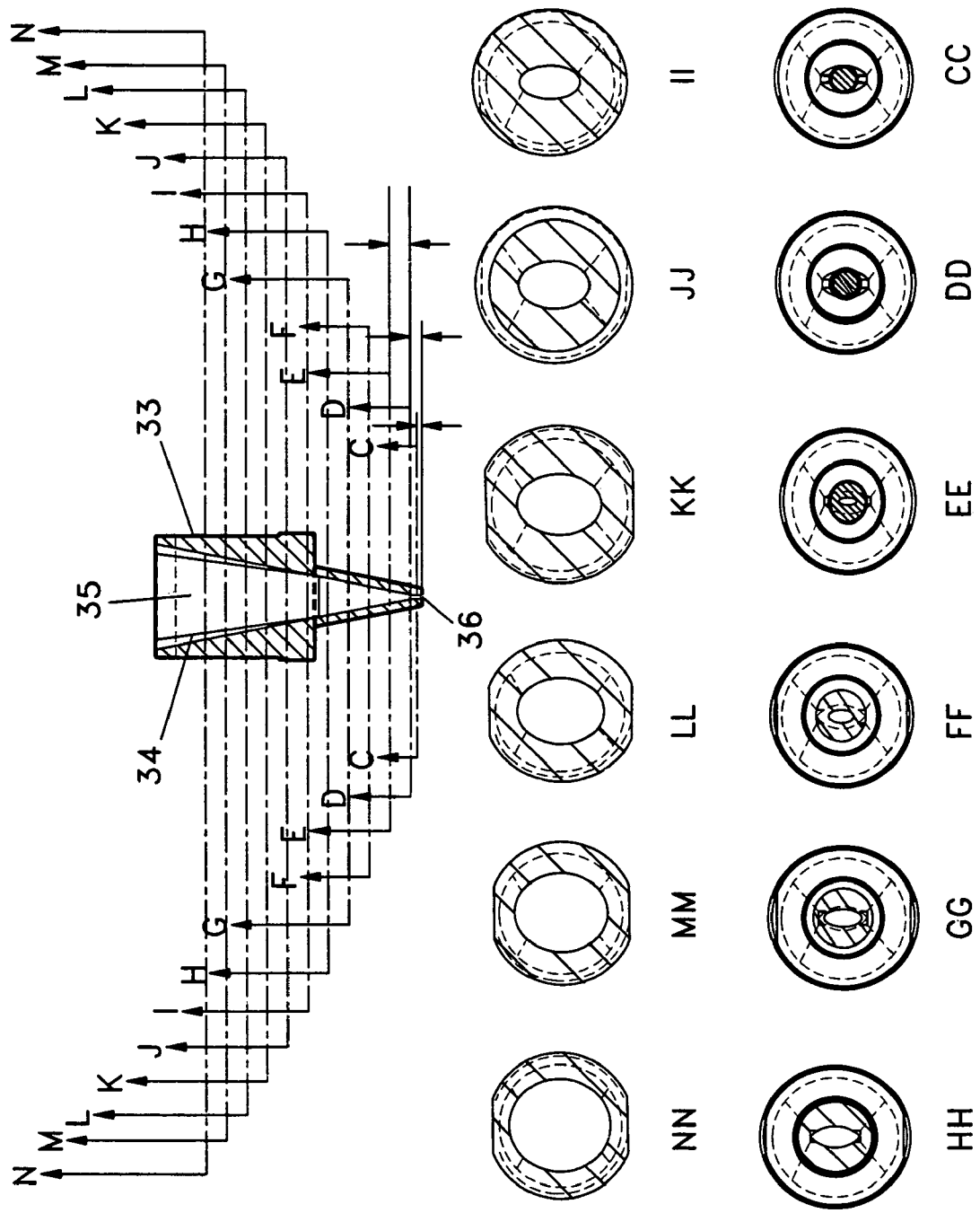
FIG. 18 shows a graded series of cross sections of the object orienting nozzle invention.
Figure 19:
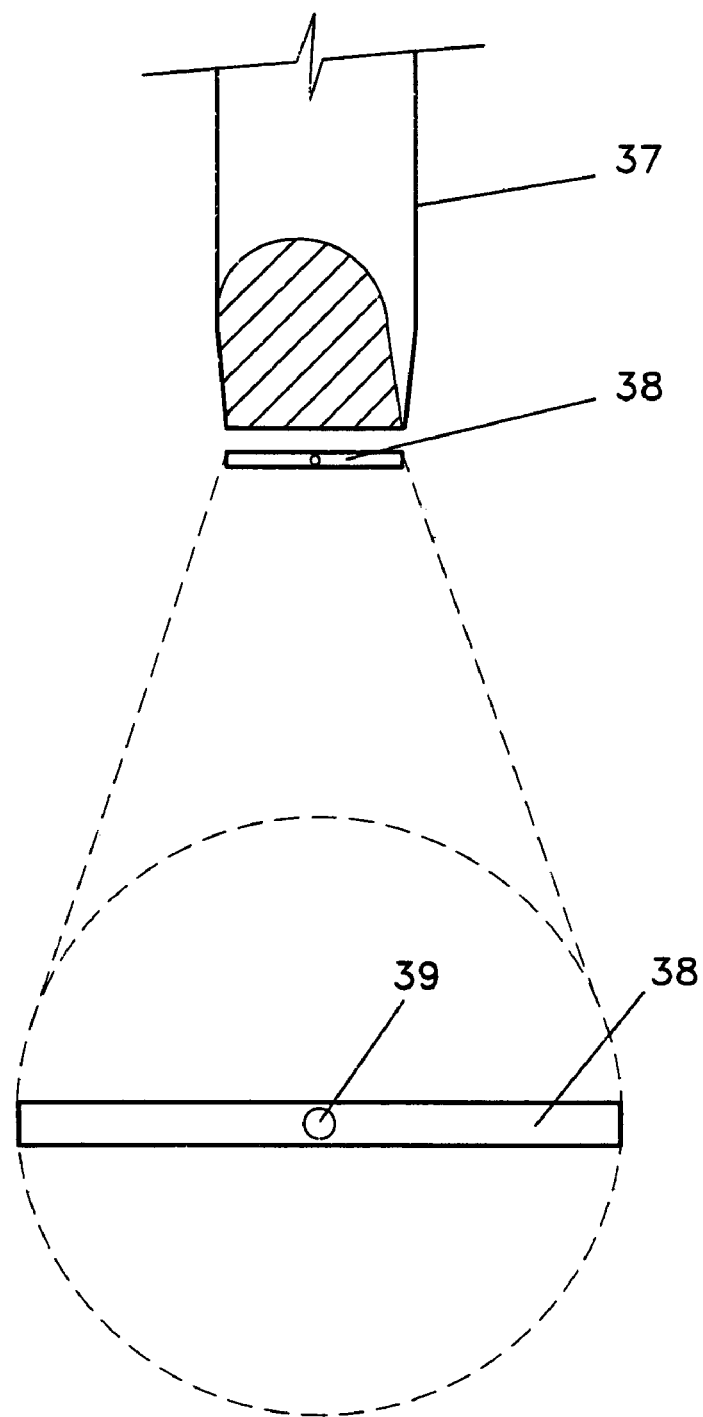
FIG. 19 shows a front view and an end view of an embodiment of the beveled injection tube invention.
Figure 22:
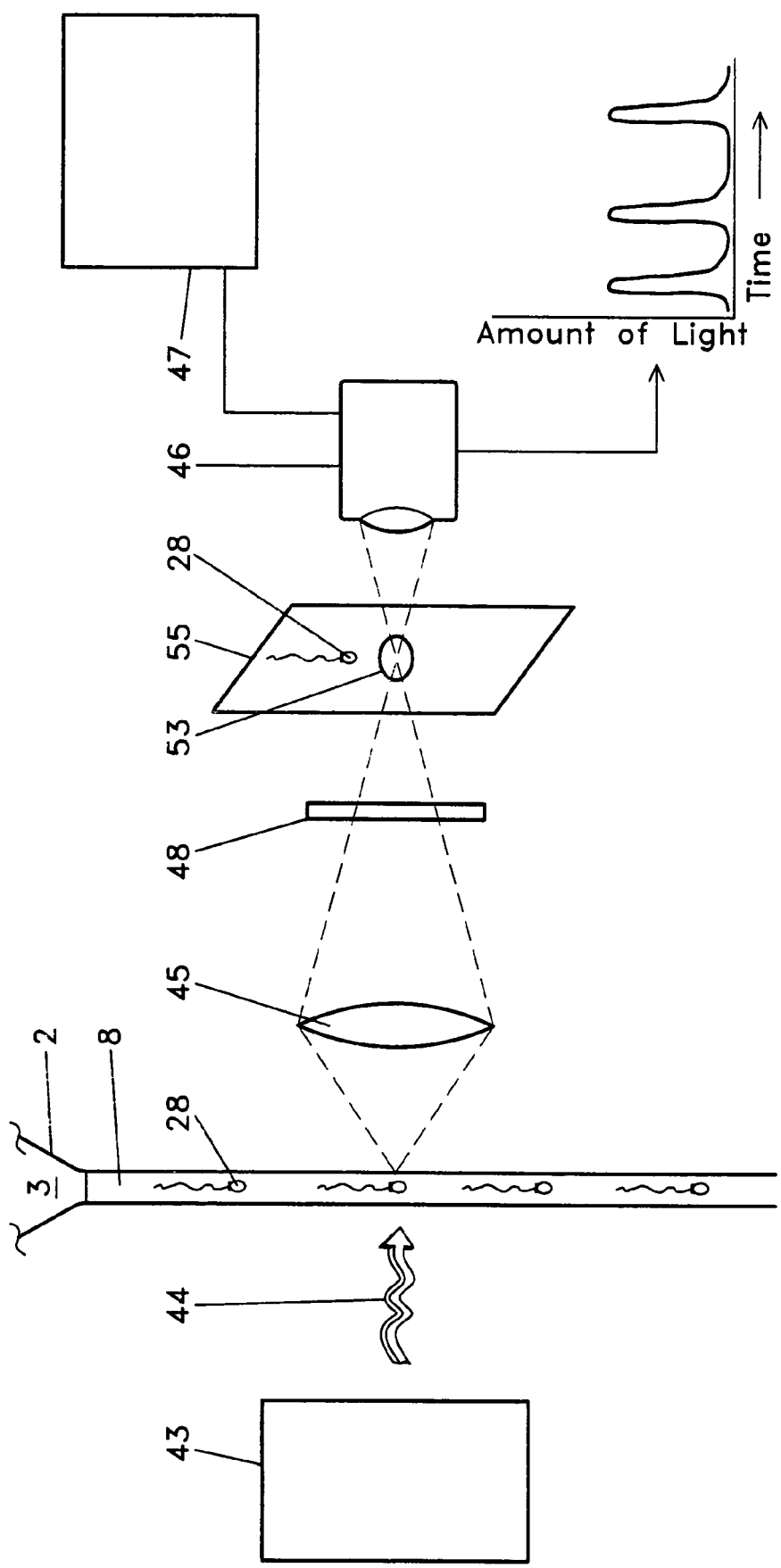
FIG. 22 shows a conventional optics technology coupled to a flow cytometer.

Now referring to FIGS. 17, 18, and 19, particular embodiments of the invention can also have an particle or sperm cell orienting nozzle (33) that hydrodynamically forces the flattened sperm head into the proper orientation as they pass in front of the photomultiplier(s). As shown by FIG. 17, the orienting nozzle has interior surfaces (34) that form a cone-like shape. The internal cone gradually changes from circular at the inlet end (35) into a highly elliptical shape near the orifice (36) where the stream exits the tip. The orifice (36) can be circular rather than elliptical. Thus, the internal aspect of the orienting nozzle (34) goes from a round entrance to a narrow ellipse to a round exit shortly before the orifice (36). This internal shape is further clarified by the cross sections of the orienting nozzle shown by FIG. 18.

As shown by FIGS. 19 and 21, the injection tube (37) (which may be about 0.061 inches in diameter) can be used with the orientation nozzle (or with a conventional nozzle) (33) which can be beveled near the tip to form a blade (38). The flattened blade (38) can be oriented at an angle 90 degrees from the greatest dimension of the ellipse in the orientation nozzle (33). The internal diameter of the injection needle can be about 0.010 inch in diameter forming a rounded orifice (39) in the center of the flattened needle tube blade (38).

In particular embodiments of the beveled injection tube the beveled blade can be configured in the paddle shape illustrated by FIG. 21. The paddle shaped beveled blade can assist in maintaining laminar flow of the sheath fluid within the nozzle (whether conventional nozzle or orienting nozzle). As such, the laminar flow of liquid maintained by the paddle shaped beveled blade presents less disruption of the objects injected into it. Spermatozoa introduced into the laminar flow of sheath fluid maintained by an embodiment of the injector tube invention having the paddle shaped beveled blade allows for a 20%, 30%, 40%, 50% or even greater increase in spermatozoa sorting rates over conventional injection tube technology. High speed sorting of spermatozoa at rates of about 4,000 to about 10,000 sorts of each sex per second can be accomplished. High purity (90% or greater) of the X-chromosome bearing and Y-chromosome bearing populations can be established at even these high sort rates. The injector tube invention with the beveled paddle shaped tip can be used independently of or in combination with the other inventions described herein or other technology such as that described in U.S. patent application Ser. No. 09/454,488 or International Patent Application No. PCT/US00/42350, each hereby incorporated by reference.

As shown by FIG. 21, certain embodiments of the beveled blade injector tube invention or beveled blade paddle shape invention can further include laminar flow enhancement grooves (40). The laminar flow enhancement grooves (40) assist in maintaining a laminar flow to the orifice of the injector tube. Again, the enhanced laminar flow allows for more spermatozoa to maintain the correct orientation in the laminar sheath fluid flow resulting in higher numbers of sortable event rates which in turn leads to higher sort rates for each sex or spermatozoa.

In another embodiment of the invention, the orienting nozzle orifice (39) or other conventional can be sized to form droplets which encapsulate intact live sperm as they exit the orifice (39). Encapsulation of the sperm cells does not occur in conventional sperm cell entrainment technology. Rather a portion of the sperm cell tail resides outside of the droplet. For example, bovine sperm cells have a length of about 13.5 microseconds when the fluid stream has a pressure of about 50 pounds per square inch (i.e. the length of time for the entire length of the sperm cell to pass through the irradiation beam at about 50 pounds per square inch fluid stream pressure). Conventional droplet formation techniques for entraining bovine sperm cells establish various conditions such as a 14 microsecond droplet (i.e. the time it takes to form a single droplet waveform in a fluid stream), a nozzle having an orifice with a diameter of about 70 micrometers, and an oscillator operated at about 35 kilohertz. Regardless of parameters selected in conventional systems, a portion of the sperm cell tail readily protrudes from the droplet. To prevent the sperm cell tail from protruding from the droplet, one embodiment of the droplet encapsulation invention provides an orifice of about 100 micrometers that can produce a droplet of about 28 microseconds at about 50 pounds per square inch at about 30 kilohertz. By entirely encapsulating the intact live sperm cell, including the tail portion, the sperm cell interacts with the nozzle less upon charging of the droplet and the deflection of the droplet can be more accurate. This leads to less cross contamination of X-chromosome bearing sperm with Y-chromosome bearing sperm and also allows deflected spermatozoa to be more uniformly collected. Sperm that are uniformly deflected can be directed to collection surfaces that are cushioned by various liquids. Cushioning the separated spermatozoa can be important in reducing stress as described in U.S. patent application Ser. No. 09/001,394, hereby incorporated by reference. With respect to spermatozoa from other species of mammals, the invention can be varied to produce droplet sizes to encapsulate the varying lengths of sperm cells. Depending on the length of the spermatozoa and the pressure of the fluid stream the droplet encapsulation invention can still achieve droplet formation rates of at least 10,000 droplets per second, at least 20,000 droplets per second, at least 30,000 droplets per second, at least 40,000 droplets per second, at least 50,000 droplets per second, at least 60,000 droplets per second, at least 70,000 droplets per second, at least 80,000 droplets per second, at least 90,000 droplets per second, at least 100,000 droplets per second and so on up to about 200,000 droplets per second in some embodiments of the droplet encapsulation invention.

Even with the orienting nozzle invention there will be a certain number of spermatozoa, or particles, which are not properly oriented in the beam pattern. As described above, if the orientation of a sperm head is not proper then the DNA content cannot be measured accurately based upon the emitted light. Particular embodiments of the present invention provide for the removal of undesired unoriented spermatozoa (RUUS) or particles within a fluid stream.

Referring now to FIGS. 16 and 20A, it can be understood that accurate measurement of the DNA content of a spermatozoa depends upon the flat surface of the paddle-shaped sperm head (28) being oriented properly with the detector. Thus, only that proportion of the spermatozoa that enter the excitation beam in the proper orientation as shown by FIGS. 16 and 20A can be measured accurately and sorted in to X-chromosome bearing and Y-chromosome bearing populations based upon DNA content. As shown by FIGS. 20A and 20B, spermatozoa which transit through the excitation beam in proper orientation generate an oriented emission signal plot (40) that can be shaped differently than the unoriented emission signal plot (41) that is generated by unoriented spermatozoa shown by FIG. 20D. Naturally, the shape of the unoriented emission signal plot (41) generated by unoriented spermatozoa will vary depending on the degree of improper orientation in the excitation beam. These improper orientations can include the orientation shown in FIG. 20C but can also include all manner of orientations that rotate the sperm head any portion of a rotation that orients the surface of the paddle-shaped head out of alignment with the detector (proper alignment shown by FIG. 16), or any portion of a rotation that orients the axis of the sperm head (42) out of alignment with the direction of flow. Naturally, proper orientation may be defined differently from species to species. For some species, in which the sperm head is not paddle-shaped, the proper orientation within the excitation beam, or relative to the detectors or otherwise, may be defined by other anatomical characteristics or signal characteristics. Nonetheless, an optimized signal for the properly oriented spermatozoa of various species within the excitation window can be generated as the standard emission signal plots for subsequent comparison with serial emission events.

By comparing the shape (or the integrated area or both) of each emission signal plot with the standard emission signal plot (or standard integrated area or both) established for an oriented spermatozoa of a species of mammal, unoriented sperm can be identified, the signal subtracted from univariate or bivariate histograms, and the unoriented sperm can be affirmatively removed, if desired, so that unoriented sperm are not collected into either the X-chromosome bearing population or the Y-chromosome bearing population.

Importantly, as the invention(s) improve(s) resolution between the two spermatozoa populations being separated which increase the rate at which the populations can be separated from one another, and improves the purity of the populations that are separated. As such, it is now possible to sort spermatozoa at remarkably high speeds. Sortable or separable event rates can be as high as about 35,000 per second (not including coincident events—multiple spermatozoa within the excitation/detection window at the same time). Sortable or separable event rates correlate with high separation or sort rates which can be about 5000 to about 11,000 intact live sperm of each sex per second with a purity of 90%, 92%, 93%, 95%, or greater. The above-described inventions also allow for even higher purity X-chromosome bearing and Y-chromosome bearing populations to be obtained of about 97% to about 98% or even higher by reducing the sort or separation rates to around 2000 live sperm of each sex per second.

As can be understood, the above inventions described are particularly important in achieving the highest possible sortable or separable event rates and highest possible resulting separation rates which can be at least 1,000 separations per second, at least 2,000 separations per second, at least 3,000 separations per second, at least 4,000 separations per second, at least 5,000 separations per second, at least 6,000 separations per second, at least 7,000 separations per second, at least 8,000 separations per second, at least 9,000 separations per second, or at least 10,000 separations per second of each sex per second, or greater.

The invention allows for high speed sorting, as set forth above, of spermatozoa even when they are difficult to stain, or have other anatomical or chemical features, that make differentiation between the X-bearing chromosome and Y-bearing chromosome populations more difficult. Even in these difficult cases, high purity X-chromosome bearing and Y-chromosome bearing populations of bovine spermatozoa can be isolated at high purity of 92% to 93% by achieving sortable event rates of about 15,000-20,000 sortable events per second or higher as described above, and sort or separation rates of intact live spermatozoa of each sex (X-chromosome bearing and Y-chromosome bearing) of 2000 intact live sperm of each sex per second.

Figure 24:
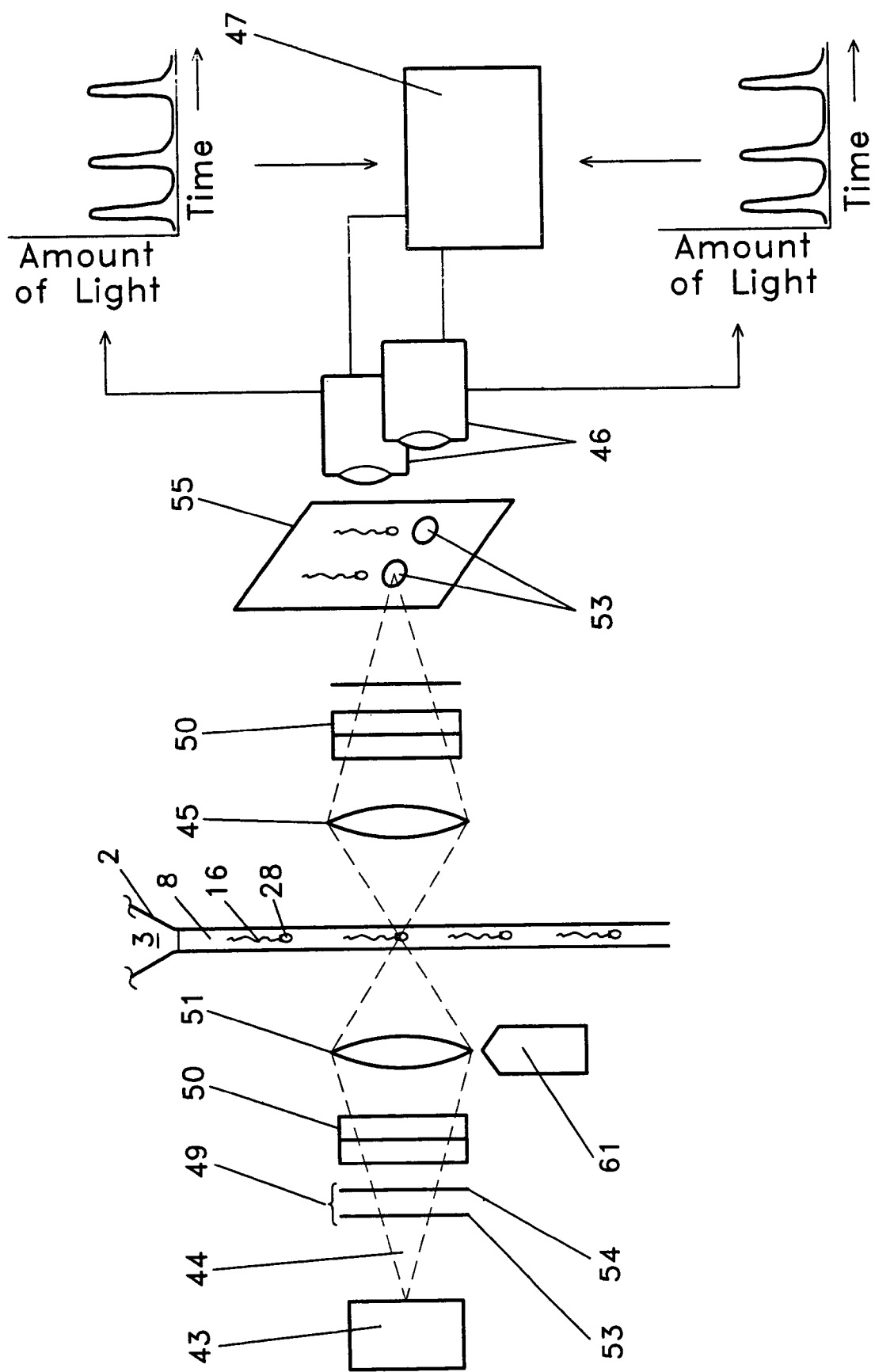
FIG. 24 shows an embodiment of the invention having construction allowing the measurement of two signals, for example volume and orientation.

Now referring to FIGS. 23 and 24, an embodiment of the invention utilizes differential interference contrast technology to measure the volume of a particle or capsule. A basic embodiment of the invention can comprise particles that have a difference volume, such as sperm cell heads (28) that have a difference in volume between X-chromosome bearing and Y-chromosome bearing sperm cells. An electromagnetic radiation source (43) generates electromagnetic radiation or a beam of electromagnetic radiation (44) having initial waveform characteristics differentially responsive to the difference in volume between the particles or sperm cell heads (28). The electromagnetic radiation which can be laser light, but could also be numerous types of electromagnetic radiation including, but not limited to, microwave radiation, ultraviolet radiation, or the like. Upon traversing the particle or capsule or sperm head volume containing phase shifting material the electromagnetic radiation can be focused through an objective lens (45) onto a detector (46) responsive to the waveform characteristics of the electromagnetic radiation. The detector can be coupled to an analyzer (47). The analyzer can differentiate between particles based on the change in the waveform characteristics prior to traversing the volume of the particle and after traversing the volume of the particle and can analyze the signal based on integrated areas or signal shape or both. In certain embodiments the invention analyzing waveform characteristics can comprise superimposing initial waveform characteristics with altered waveform characteristics upon traversing the volume of the particle, capsule, or sperm cell head. Superimposing the initial waveform characteristics and the phase shifted waveform characteristic can differentially modulate the intensity of the beam of electromagnetic radiation in manner that correlates to the amount of phase shift media the electromagnetic radiation traverses. The invention may also include additional filters (48), such as color filters.

Now referring to FIG. 24, an embodiment of the optics invention involves using differential interference contrast optics that increase the actual distance over which the light is split up compared to conventional DIC microscopy which corresponds to the resolution limit of the microscope. In this embodiment of the invention, the induced split is larger than the size of the objects, thus giving rise to two individual images, separated laterally, originating from one object. The second modification involves using plates of birefringent material, such as Savart plates, at a location away from the objective lens. This embodiment of the invention is easier to construct since the birefringent materials do not have to be located inside the objective housing. In conventional DIC microscopes the birefringent material is used in the form of so-called Wollaston prisms, that have to be located inside the objective housing, making it necessary to use expensive objective lenses that have been manufactured specifically for this purpose.

Components of an embodiment of the invention may be arranged in line with each other and consist of: a source of electromagnetic radiation (43), for example, a Mercury arc lamp; a spectral adjustment element, for example, a bandpass filter; a polarization adjustment element (49), for example, a sheet polarizer (53) and a waveplate (54) responsive to a rotatable mount; a light condenser (51) allowing the light to be condensed onto the particle or sperm cell, for example, a condenser lens, or set of lenses, or microscope objective; a fluid stream (8) that may contain particles or sperm cells (28), for example a fluid jet ejected under pressure; a light collector (45) to collect the light from the particle or cell, for example a 50×high working distance microscope objective and a tube lens; a beam splitter (50) to split up the beam into two, or more, components, for example, a piece of birefringent material in the form of a Savart plate, mounted in such a way that its orientation can be controlled accurately; image light selector (55) to select only the light corresponding to the particle or sperm cell, for instance a set of pinholes, one pinhole (53) for each of the images formed.

In one embodiment of the invention, the components may be arranged in such a way that the light source (43) or its image are located at the back focal plane of the light condenser (45) often referred to as Köhler type illumination. The image of the object plane may best coincide with the object light selector (55) or pinhole(s) (53), in order to capture the light from individual particles or sperm cells. As shown in FIGS. 27 and 28, components can be mounted on a sturdy optical table, or bench, using mountings, posts, and holders. Components can be mounted in such a way that focusing of the object plane can be done accurately. This can be done by equipping the fluid stream with a stream position controller, such as micrometers, in order to turn the stream in and out of focus. In addition it may be necessary to equip the light condenser (51) with a light condenser position controller (61) allowing it to be focused onto the object plane. It may be necessary to take special care about the mounting of the birefringent elements or beam splitter (50), a three axis rotation element may be preferable.

Now referring to FIG. 25, embodiments of the present invention may also include the use of both generated images, in order to determine the orientation of a asymmetrical particles the fluid stream, including, but not limited to, spermatozoa such as bull sperm cells. An orientation assessment embodiments of the invention can include an optical system that allows for control of the polarization state of the light entering the system for both generated images independently. The interference optics invention may further provide polarization adjustment element (56) that controls the polarization state of light entering the system. For the orientation detection invention the polarization adjustment element (56) may be selected in such a way that it consists of two parts, that are imaged onto image light selector (55) that in one embodiment of the invention contains the pinholes (53). This can be accomplished by locating the polarization adjustment element (56) in the conjugate plane of the image plane (55), or by using other optics, to accomplish the same thing. A simple example of this component may be a 'half-shade' piece, for instance consisting of two hemicircular parts of polarizing material, such as sheet-polarizer, the orientation angle of which may be chosen independently. Each pinhole in the image plane can fall in one of the halves of said hemisphere. The polarization angles can be chosen in such a way that the signal of one pinhole (53) corresponds to the volume, and is relatively independent from the orientation angle of the passing object, and the other pinhole (53) has a signal that depends, to a great degree, upon this orientation angle. The two signals may be processed by analyzer (47) in a manner similar to a conventional multichannel flow cytometry, as but one example. With respect to this example, bivariate dotplots can be made, and also allow the user to select windows on this plot.

An improvement of the 'half-shade' piece described above may be the construction shown by FIG. 25D. The same said two hemispherical parts are projected onto the image plane but the way they are generated is different. A mirror (57) breaks up the light (44) into the hemi-circular parts, and recombines them back to back. Each of the halves traverses a separate means to control its polarization state. An advantage of this embodiment is that the polarization angles can be controlled continuously and independently, thus facilitating the adjustment of the set-up. Materials used in this embodiment can be supplied by standard optical supply firms, and can be mounted in the set-up using similar mounting materials as used for the interferometric optics.

Now referring to FIG. 26, In order to correct for artifacts introduced by having light pass through a non-flat region of transparent material, such as a substantially cylindrical fluid stream but including other geometries as well, embodiments of the present invention disclose the incorporation of a component similar in shape to the non-flat region, but opposite in terms of relative refractive indices. In the specific case of a flow cytometer this shape approximates a cylinder. To correct for artifacts introduced by the fact that the objects to be assessed are located within a cylindrical stream of water, is the incorporation of an optical component (58) which can be in the shape of a transparent cylinder, located inside transparent material (59) of a higher refractive index. It may be preferred that the image of the stream and of the compensation element fall on top of each other in the image plane. This can be done by locating the compensation element between the objective lens and the image plane, and by incorporating auxiliary lenses.

An embodiment of the optical component (58) can be located within a thin slice of transparent material of higher refractive index (59), for instance glass, or perspex, with a cylindrical hole drilled across it. Perspex has the advantage that it can be easier to drill a round channel into it. The cylindrical hole may be filled by a transparent material, the refractive index of which is lower than that of the surrounding material. The difference in refractive index between the substance and the surrounding material can be the same as but opposite to the difference in refractive index between the water in the stream and the surrounding air for certain applications. It may not be necessary to have the cylinder the same size as the stream of water, as long as magnification by the lenses used, makes the resulting images in the image plane the same size. In some applications, it may be desired or necessary to adjust the refractive index difference to compensate for this magnification. Manufacturing of such element out of perspex can be quite simple, and can be done by most mechanical workshops that have experience with machining perspex or the selected material. It may be made in such dimensions that it fits in a standard optical mounting hardware, to facilitate incorporation into the optics.

Exactly matching the refractive indices may be difficult. An embodiment of the invention that facilitates adjustment can be to make the substance inside the perspex, or other selected material, a transparent refractive index fluid (58), as but one example, an organic oil, or mixture of oils that have a refractive index close to the desired one. Due to the fact that the refractive index of most fluids changes with temperature, much more so than solids, or glasses, it may be possible to fine-tune the difference in refractive index by temperature. This may be done by incorporating a temperature controller (60).

Optical component (58) of transparent fluids or refractive index fluids can be supplied by chemical supply firms. These firms often have data regarding the refractive index of their fluids readily available. Some firms even offer fluids that are specially made to serve as refractive index fluids, and have a guaranteed and stable refractive index. Temperature controllers and thermostats are supplied by many firms. A practical way to apply heat to the refractive index fluid can be to use a hollow mounting made of heat conducting material, a metal as but one example, containing the refractive index fluid. Using a conventional immersion thermostat cycler, found in many laboratories, water can be pumped through the mounting, thus keeping the element at a fixed and controllable temperature.

The discussion included in this PCT application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function is accomplished by a device, subroutine, or program. Apparatus claims may not only be included for the devices described, but also method or process claims may be included to address the functions the invention and each element performs. Neither the description nor the terminology is intended to limit the scope of the claims which now be included.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "droplet separator" should be understood to encompass disclosure of the act of "separating droplets"—whether explicitly discussed or not—and, conversely, were there only disclosure of the act of "converting liquid-gas", such a disclosure should be understood to encompass disclosure of a "droplet separator" and even a means for "separating droplets". Such changes and alternative terms are to be understood to be explicitly included in the description.

Additionally, the various combinations and permutations of all elements or applications can be created and presented. All can be done to optimize the design or performance in a specific application.

Any acts of law, statutes, regulations, or rules mentioned in this application for patent: or patents, publications, or other references mentioned in this application for patent are hereby incorporated by reference. Specifically, U.S. patent application Nos. 60/267,571, 60/239,752, and 60/203,089 are each hereby incorporated by reference herein including any figures or attachments, and each of references in the following table of references are hereby incorporated by reference.

| DOCUMENT NO. | DATE | NAME | CLASS | SUBCLASS | FILING DATE |
|---|---|---|---|---|---|
| 32,350 | Feb. 10, 1987 | Bhattacharya | 204 | 180.1 | Nov. 22, 1974 |
| 3,687,806 | Aug. 29, 1972 | Van den Bovenkamp | 195 | 1.3 | Nov. 4, 1969 |
| 3,829,216 | Aug. 13, 1974 | Persidsky | 356 | 36 | Oct. 2, 1972 |
| 3,894,529 | Jul. 15, 1975 | Shrimpton | 128 | 1 R | Apr. 10, 1969 |
| 4,009,260 | Feb. 22, 1977 | Ericcson | 424 | 561 | Oct. 11, 1974 |
| 4,067,965 | Jan. 10, 1978 | Bhattacharya | 424 | 105 | Dec. 17, 1975 |
| 4,083,957 | Apr. 11, 1978 | Lang | 424 | 78 | Feb. 4, 1976 |
| 4,085,205 | Apr. 18, 1978 | Hancock | 424 | 105 | Jan. 24, 1977 |
| 4,092,229 | May 30, 1978 | Bhattacharya | 204 | 180 R | Oct. 20, 1976 |
| 4,155,831 | May 22, 1979 | Bhattacharya | 207 | 299 R | Feb. 23, 1978 |
| 4,191,749 | Mar. 4, 1980 | Bryant | 424 | 105 | Oct. 11, 1977 |
| 4,225,405 | Sep. 30, 1980 | Lawson | 204 | 180 R | Aug. 16, 1978 |
| 4,276,139 | Jun. 30, 1981 | Lawson | 204 | 180 R | Oct. 9, 1979 |
| 4,339,434 | Jul. 13, 1982 | Ericcson | 424 | 561 | Aug. 17, 1981 |
| 4,362,246 | Dec. 7, 1982 | Adair | 209 | 3.3 | Jul. 14, 1980 |
| 4,448,767 | May 15, 1984 | Bryant | 424 | 85 | Feb. 15, 1980 |
| 4,474,875 | Oct. 2, 1984 | Shrimpton | 435 | 002 | Aug. 18, 1980 |
| 4,501,366 | Feb. 26, 1985 | Thompson | 209 | 556 | Dec. 14, 1982 |
| 4,511,661 | Apr. 16, 1985 | Goldberg | 436 | 503 | Dec. 20, 1983 |
| 4,605,558 | Aug. 12, 1986 | Shrimpton | 424 | 561 | Apr. 20, 1984 |
| 4,660,971 | Apr. 28, 1987 | Sage et al. | 356 | 39 | May 3, 1984 |
| 4,680,258 | Jul. 14, 1987 | Hammerling et al | 435 | 7 | Aug. 9, 1983 |
| 4,698,142 | Oct. 6, 1987 | Muroi et al | 204 | 182.3 | Jul. 31, 1985 |
| 4,749,458 | Jun. 7, 1988 | Muroi et al | 204 | 182.3 | Mar. 2, 1987 |
| 4,988,619 | Jan. 29, 1991 | Pinkel | 435 | 30 | Nov. 30, 1987 |
| 4,999,283 | Mar. 12, 1991 | Zavos et al | 435 | 2 | Aug. 18, 1989 |
| 5,021,244 | Jun. 4, 1991 | Spaulding | 424 | 561 | May 12, 1989 |
| 5,135,759 | Aug. 4, 1992 | Johnson | 424 | 561 | Apr. 26, 1991 |
| 5,346,990 | Sep. 13, 1994 | Spaulding | 530 | 350 | Mar. 12, 1991 |
| 5,371,585 | Dec. 6, 1994 | Morgan et al. | 356 | 246 | Nov. 10, 1992 |
| 5,439,362 | Aug. 8, 1995 | Spaulding | 424 | 185.1 | Jul. 25, 1994 |
| 5,466,572 | Nov. 14, 1995 | Sasaki et al. | 435 | 2 | Apr. 25, 1994 |
| 5,483,469 | Jan. 9, 1996 | Van den Engh et al. | 364 | 555 | Aug. 2, 1993 |
| 5,503,994 | Apr. 2, 1996 | Shear et al. | 436 | 90 | Oct. 8, 1993 |
| 5,514,537 | May 7, 1996 | Chandler | 435 | 002 | Nov. 28, 1994 |
| 5,589,457 | Dec. 31, 1996 | Wiltbank | 514 | 12 | Jul. 3, 1995 |
| 5,602,039 | Feb. 11, 1997 | Van den Engh | 436 | 164 | Oct. 14, 1994 |
| 5,602,349 | Feb. 11, 1997 | Van den Engh | 73 | 864.85 | Oct. 14, 1994 |
| 5,660,997 | Aug. 26, 1997 | Spaulding | 435 | 7.21 | Jun. 7, 1995 |
| 5,690,895 | Nov. 25, 1997 | Matsumoto et al. | 422 | 73 | Dec. 6, 1996 |
| 5,700,692 | Dec. 23, 1997 | Sweet | 436 | 50 | Sep. 27, 1994 |
| 5,726,364 | Mar. 10, 1998 | Van den Engh | 73 | 864.85 | Feb. 10, 1997 |
| 5,819,948 | Oct. 13, 1998 | Van den Engh | 209 | 158 | Aug. 21, 1997 |
| 5,880,457 | Mar. 9, 1999 | Tomiyama et al. | 250 | 207 | Jun. 16, 1997 |
| 5,985,216 | Nov. 16, 1999 | Rens, et al. | 422 | 073 | Jul. 24, 1997 |
| 6,071,689 | Jun. 6, 2000 | Seidel et al. | 435 | 2 | Jan. 29, 1998 |
| WO 96/12171 | Oct. 13, 1995 | | | | |
| WO 98/34094 | Jun. 8, 1998 | | | | |
| WO 99/05504 | Jul. 24, 1998 | | | | |
| WO 99/33956 | Aug. 7, 1999 | | | | |
| WO 99/38883 | May 8, 1999 | | | | |
| WO 99/42810 | Aug. 26, 1999 | | | | |
| WO 00/06193 | Oct. 2, 2000 | | | | |

Akhtar, S., et al., "Sex Preselected in Cattle: a Field Trial", Veterinary Record 136, 1995, p. 495-496.
Akhtar, S., et al., "Prevalence of Five Stereotypes of Bluetongue Virus in a Rambouillet Sheep Flock in Pakistan", Veterinary Record 136, 1995, p. 495.
Amann, R. P. et al, "Prospects For Sexing Mammalian Sperm," Colorado Associated University Press, Animal Reproduction Laboratory College of Veterinary Medicine and Biomedical Sciences, Colorado State University, Fort Collins, CO, 80523, 1982
Amoah, E. A. and Gelaye, S. 1996. Biotechnological advances in goat reproduction. J. Anim. Sci. 75(2): 578-585.
Anderson, V. K., Aamdal, J. and Fougner, J. A. 1973. Intrauterine und tiefzervikale Insemination mit Gefriersperma bein Schat. Zuchthygiene. 8: 113-118.
Baker, R. D., Dziuk, P. J. and Norton, H. W. 1968. Effect of volume of semen, number of sperm and drugs on transport of sperm in artificially inseminated gilts. J. Anim. Sci. 27: 88-93.
Barnes, F. L., and Eyestone, W. H., "Early Cleavage and the Maternal Zygotic Transition in Bovine Embryos", Theriogenology, Vol. 33, No. 1, January 1990, pp. 141-149
Becker, S. E. and Johnson, A. L. 1992. Effects of gonadotropin releasing hormone infused in a pulsatite or continuous fashion on serum gonadotropin concentrations and ovulation in the mare. J. Anim. Sci. 70: 1208-1215.
Bedford, S. J. and Hinrichs, K. 1994. The effect of insemination volume on pregnancy rates of pony mares. Theriogenology 42: 571-578.
Berger, G. S. 1987. Intratubal insemination. Fert. Steril. 48: 328-330.

-continued

Beyhan, Z., et al., "Sexual Dimorphism in IVM-IVF Bovine Embryos Produced from X and Y Chromosome-bearing Spermatozoa Sorted by High Speed Flow Cytometry", Theriogenology 52, 1999, pp. 35-48.
Blanchard, T. and Dickson, V., "Stallion Management", The Veterinary Clinics of North America, Equine Practice, Vol. 8, No. 1, April 1992, pp 207-218.
Bracher, V. and Allen, W. R., "Videoendoscopic Examination of the Mare's Uterus: Findings in Normal Fertile Mares", Equine Veterinary Journal, Vol. 24 (1992), pp. 274-278
Braselton, W. E. and McShan, W. H. 1970. Purification and properties of follicle stimulating and luteinizing hormones from horse pituitary glands. Arch. Biochem. Biophys. 139: 45-48.
Brethour, J. R. and Jaeger, J. R., "The Single Calf Heifer System", Kansas Agric. Sta. Rep of Progress 570, 1989.
Bristol, S. P. 1982. Breeding behavior of a stallion at pasture with 20 mares in synchronized oestrus. J. Reprod. Fert. Suppl. 32: 71.
Buchanan, B. R., et al, "Insemination of Mares with Low Numbers of Either Unsexed or Sexed Spermatozoa", Theriogenology, Vol. 53, pp 1333-1344, (2000)
Burwash, L. D., Pickett, B. W., Voss, J. L. and Back, D. G. 1974. Relatioship of duration of estrus to pregnancy rate in normally cycling, non-lactating mares. J. A. V. M. A. 165: 714-716.
Caslick, E. A., "The Vulva and the Vulvo-vaginal Orifice and its Relation to Genital Health of the Thoroughbred Mare", Cornell Veterinarian, Vol. 27, 1937, pp. 178-187
Catt, et al., "Assessment of Ram and Boar Spermatozoa During Cell-Sorting by Flow Cytometry", Reproduction Dom Animal, Vol. 32, 1997, pp 251-258.
Catt, S. L., et al., "Birth of a Male Lamb Derived from an In Vitro Matured Oocyte Fertilized by Intracytoplasmic Injection of a Single Presumptive Male Sperm", Veterinary Record 139, 1996, pp. 494-495.
Chandler, J. E., et al, "Bovine Spermatozoal Head Size Variation and Evaluation of a Seperation Technique Based on this Size", Theriogeneology 52, p. 1021-1034 (1999)
Chandler, J. E., "Videomicroscopic Comparison of Bull Sperm and Leukocyte Chromosome Areas as Related to Gender", J Dairy Sci 73, pp. 2129-2135, (1990)
Chin, W. W. and Boime, I. 1990. In: Glycoprotein Hormones. Serona Symp. Norwell, MA. pp. 19-20
Chung, Y. G., Schenk, J. L., Herickhoff, L. A. and Seidel, G. E. Jr. 1998. Artificial insemination of superovulated heifers with 600,000 sexed sperm. J Anim. Sci. Suppl. 1. 836: 215. abstr.
Clement, F., Vincent, P., Mahla, R., Meriaux, J. C. and Palmer, E. 1998. Which insemination fertilizes when several successive inseminations are performed before ovulation. 7$^{th}$ Int. Symp. Eq. Repro. 151. abstr.
Cran, D. G., et al, "Production of Lambs by Low Dose Intrauterine Insemination with Flow Cytometrically Sorted and Unsorted Semen", Theriogenology, Vol. 47, pp. 267, (Abstract), (1997)
Cran, D. G., et al "Production of Bovine Calves Following Separation of X- and Y-Chromosome Bearing Sperm and In Vitro Fertilisation", Veterinary Record 132, 1993, pp. 40-41.
Cran, D. G., Johnson, L. A. and Polge, C., 1995, "Sex preselection in cattle: a field trial", Vet. Rec. 136: 495-496.
Cui, K., "Size Differences between human X and Y Spermatozoa and prefertilization diagnosis", Molecular Human Reproduction, Vol. 3, No. 1, pp. 61-67, (1997)
Cui, K., "X Larger than Y", Nature 366, p. 177-118, (1993)
Curran, S. 1998. In: Equine Diagnostic Ultrasonography. Fetal gender determination. Rantanen & McKinnon. 1$^{st}$ Ed. Williams and Wilkins. pp. 165-169.
Day, B. N., Abeydeera, L. R., Johnson, L. A., Welch, G. R., Wang, W. H., Cantley, T. C. and Rieke, A. 1998. Birth of piglets preselected for gender following in vitro fertilization of in vitro matured pig oocytes by X and Y bearing spermatozoa sorted by high speed flow cytometry. Theriogenology. 49(1): 360. abstr.
Dean, P. N., Pinkel, D. and Mendelsob. n, M. L. 1978. Hydrodynamic orientation of spermatozoa heads for flow cytometry. Biophys. J. 23: 7-13.
Demick, D. S., Voss, J. L. and Pickett, B. W. 1976. Effect of cooling, storage, glycerization and spermatozoal numbers on equine fertility. J. Anim. Sci. 43: 633-637.
DenDaas, J. H. G., De Jong, G., Lansbergen, L. M. T. E. and Van Wagtendonk-De Leeuw, A. M. 1998. The relationship between the number of spermatozoa inseminated and the reproductive efficiency of dairy bulls. J Dairy Sci. 81: 1714-1723.
Dinnyes, A., et al., "Timing of the First Cleavage Post-insemination Affects Cryosurvival of In Vitro-produced Bovine Blastocysts", Molec Reprod develop 53, 1999, pp 318-324.
Donaldson, L. E., "Effect of Insemination Regimen on Embryo Production in Superovulated Cows", The Veterinary Record, Jul. 13, 1985, pp. 35-37
Donoghue, et al, 1996. "Timing of ovulation after gonadotropin induction and its importance to successful intrauterine insemination in the tiger (Panthera tigris)", J. Reprod. Fert. 107: 53-58.
Douglas, R. H. 1979. "Review of superovulation and embryo transfer in the equine", Theriogenology. 11: 33-46.
Douglas, R. H., Nuti, L. and Ginther, O. J. 1974. Induction of ovulation and multiple ovulation on seasonally-anovulatory mares with equine pituitary fractions. Theriogenology. 2(6): 133-142.
Duchamp, G., Bour, B., Combarnous, Y. and Palmer, E. 1987. Alternative solutions to hCG induction of ovulation in the mare. J. Reprod. Fert. Suppl. 35: 221-228.
Evans, M. J. and Irvine, C. H. G. 1977. Induction of follicular development, maturation and ovulation by gonadotropin releasing hormone administration to acyclic mares. Bio. Reprod. 16: 452-462.
Fitzgerald, B. P., Peterson, K. D. and Silvia, P. J. 1993. Effect of constant administration of a gonadotropin-releasing hormone agonist on reproductive activity in mares: Preliminary evidence on suppression of ovulation during the breeding season. Am. J. Vet. Res. 54: 1746-1751.
Fluharty, F. L., et al., "Effects of Age at Weaning and Diet on Growth of Calves", Ohio Agri. Res. and Dev. Circular, 1996, 156: 29.
Foulkes, J. A., et al., 1977. "Artificial insemination of cattle using varying numbers of spermatozoa", Vet. Rec. 101: 205.
Francon, M. and Yamamoto, T., "Un Noveau et tres simple dispositif interferentiel applicable as microscpe", Optica Acta 9, p. 395-408 (1962)
Fugger, E. F., "Clinical Experience with Flow Cytometric Separation of Human X- and Y-Chromosome Bearing Sperm", Theriogenology, Vol. 52, pp. 1435-1440 (1999)
Fulwyler, M. J. 1965. "Electronic separation of biological cells by volume", Science. 150: 910.
Fulwyler, M. J. 1977. "Hydrodynamic orientation of cells", J Histochem. Cytochem. 25: 781-783.
Garner, D. L., et al., 1983. "Quantification of the X and Y chromosome-bearing spermatozoa of domestic animals by flow cytometry", Biol. Reprod. 28: 312-321.
Ginther, O. J. 1971. "Some factors which alter estrus cycle in mares", J. Anim. Sci. 33: 1158. abstr.
Ginther, O. J. 1983. "Sexual behavior following introduction of a stallion into a group of mares", Theriogenology. 19: 877.

-continued

Ginther, O. J. 1992. "In: Reproductive Biology of the Mare", (2nd Ed.) Equiservices, Cross Plains, WI.
Gledhill, B. L. 1988. Gender preselection: historical, technical and ethical perspective. Semin Reprod. Endocrinol. 6: 385-395.
Gourley, D. D. and Riese, R. L. 1990. Laparoscopic artificial insemination in sheep. Vet. Clin. N. Amer: Food Anim. Prac. 6(3): 615-633.
Grondahl, C., et al, "In Vitro Production of Equine Embryos", Biology of Reproduction, Monograph Series I, pp. 299-307 (1995)
Guillou, F. and Combarnous, Y. 1983. Purification of equine gonadotropins and comparative study of their acid-dissociation and receptor-binding specificity. Biochem. Biophys. Acta. 755: 229-236.
Gurnsey, M. P., and Johnson, L. A., "Recent improvements in efficiency of flow cytometric sorting of X and Y-chromosome bering sperm of domestic animals: a review", 1998, New Zealand Society of Animal Protection, three pages.
HAMAMATSU, Photomultiplier Tubes", web page, http://www.optics.org/hamamatsu/pmt.html, printed out on Apr. 15, 2000, four pages total.
HAMAMATSU, Technical Information", web page, http://www.optics.org/hamamatsu/photodiode.html, printed out on Apr. 15, 2000, six pages total.
Hamano, K., et al., "Gender Preselection in Cattle with Intracytoplasmically Injected, Flow Cytometrically Sorted Sperm Heads", Biology of Reproduction 60, 1999, pp. 1194-1197.
Harrison, L. A., et al., 1991. Comparison of hCG, buserelin and luprostiol for induction of ovulation in cycling mares. Eq. Vet. Sci. 3: 163-166.
Hawk, H. W., et al., "Fertilization Rates in Superovulating Cows After Deposition of Semen on the Infundibulum Near the Uterotubal Junction or After Insemination with High Numbers of Sperm", Theriogenology, May 1988, Vol. 29, No. 5, pp 1131-1142.
Hofferer, S., Lecompte, F., Magallon, T., Palmer, E. and Combarnous, Y. 1993. Induction of ovulation and superovulation in mares using equine LH and FSH separated by hydrophobic interaction chromatography. J. Reprod. Fert. 98: 597-602.
Holtan, D. W., Douglas, R. H. and Ginther, O. J. 1977. Estrus, ovulation and conception following synchronization with progesterone, prostaglandin F2 ct and human chorionic gonadotropin in pony mares. J. Anim. Sci. 44: 431-437.
Householder, D. D., Pickett, B. W., Voss, J. L. and Olar, T. T. 1981. Effect of extender, number of spermatozoa and hCG on equine fertility. J. Equine Vet. Sci. 1: 9-13.
Howard, J. G., et al., 1991. "Comparative semen cryopreservation in ferrets (*Mustela putorious furo*) and pregnancies after laparoscopic intrauterine insemination with frozen-thawed spermatozoa". J. Reprod. Fert. 92: 109-118.
Howard, J. G., et al., 1997. "Sensitivity to exogenous gonadotropins for ovulation and laparoscopic artificial insemination in the theetab and clouded leopard". Biol. Reprod. 56: 1059-1068.
Hunter, R. H. F. 1980. Transport and storage of spermatozoa in the female reproductive tract. Proc 4th Int. Congr. Artira. Repro. and A.I. 9: 227-233.
Hyland, J. H., et al., 1988. "Gonadotropin-releasing hormone (GnRH) delivered by continuous infusion induces fertile estrus in mares during seasonal acyclicity". Proc. Amer. Assoc. Eq. Prac. 181-190.
Irvine, C. H. G. and Alexander, S. L., In: Equine Reproduction. Edited by McKirmon and Voss. Lea and Febiger. Philadelphia, London. pp. 37. (1993)
Jafar, et al., "Sex Selection in Mammals: A Review", Theriogenology, Vol. 46, pp 191-200 (1996)
Jasko, D. J., Martin, J. M. and Squires, E. L. 1992. Effect of volume and concentration of spermatozoa on embryo recovery in mares. Theriogenology. 37: 1233-1239
Johnson, A. L. 1986. "Pulsatile release of gonadotropin releasing hormone advances ovulation in cycling mares". Biol. Reprod. 35: 1123-1130.
Johnson, A. L. and Becker, S. E. 1988. "Use of gonadotropin-releasing hormone (GnRH) treatment to induce multiple ovulations in the anestrous mare", Eq. Vet. Sci. 8: 130-134. (1988)
Johnson, L. A., "Advances in Gender Preselection in Swine" Journal of Reproduction and Fertility Supplement, Vol. 52, pp. 255-266 (1997)
Johnson, L. A., "Sex Preselection in Swine: Altered Sex Ratios in Offspring Following Surgical Insemination of Flow Sorted X- and Y-Bearing Sperm", Reproduction in Domestic Animals, Vol. 26, pp. 309-314 (1991)
Johnson, L. A. and Welch, G. R. "Sex Preselection: High-speed flow cytometric sorting of X and Y sperm for maximum efficiency", Theriogenology, Vol. 52, (1999), pp. 1323-1341
Johnson, L. A. and Schulman, J. D. "The safety of sperm selection by flow cytometry", Ham. Reprod. 9(5): 758. (1994)
Johnson, L. A., and Pinkel, D., "Modification of a Laser-Based flow Cytometer for High-Resolution DNA Analysis of Mammalian Spermatozoa", Cytometry 7, pp 268-273. (1986)
Johnson, L. A., et al., "Sex Preselection in Rabbits: Live Births from X and Y Sperm Separated by DNA and Cell Sorting", Execptional Paper-Rapid Publication, XP-002103476, Biology of Reproduction 41, pp. 199-203 (1999)
Johnson, L. A., et al., "Flow sorting of X and Y chromosome-bearing sperm for DNA using an improved preparation method and staining with Hoechst 33342", Gam. Res. 17: 1-9., (1987)
Johnson, L. A., et al, "Enhanced flow cytometric sorting of manunalian X and Y sperm: high speed sorting and orienting no77.1e for artificial insemination. Theriogenology. 49(1): 361. abstr. (1988)
Johnson, L. A., et al, "Sex Preselection in Swine: Flow Cytometric Sorting of X- and Y-Chromosome Bearing Sperm to Produce Offspring", Boar Semen Preservation IV, pp. 107-114 (2000)
Johnson, L. A., et al., "Improved flow sorting resolution of X- and Y-chromosome bering viable sperm separation using dual staining and dead cell gating. Cytometry 17 (suppl 7): 83. (1989)
Johnson, L. A., "Flow cytometric determination of spermatozoa sex ratio in semen purportedly enriched for X or Y bearing spermatozoa. Theriogenology. 29: 265. abstr. (1988)
Johnson, L. A. "Gender preselection in domestic animals using flow cytometrically sorted sperm. J Anim. Sci. Suppl 1.70: 8-18. (1992)
Johnson, L. A., "Gender preselection in Mammals: An overview", Deutsch. Tierarztl. Wschr, Vol. 103, pp 288-291 (1996)
Johnson, L. A. "Isolation of X- and Y-bearing spermatozoa for sex preselection. In: Oxford Reviews of Reproductive Biology. Ed. HH Charlton. Oxford University Press. 303-326 (1994)
Johnson, L. A., "Successful Gender Preselection in Farm Animals", Agricultural Biotechnology, 1998, pp. 439-452.
Kachel, V., et al., "Uniform Lateral Orientation, Cused by Flow Forces, of Flat Particles in Flow-Through Systems", The Journal of Histochemistry and Cytochemistry, 1997, Vol. 25, No. 7, pp 774-780.
Kanayama, K., et al. "Pregnancy by means of tubal insemination and subsequent spontaneous pregnancy in rabbits", J. Int. Med. Res. 20: 401-405. (1992)
Karabinus, et al., "Effects of Egg Yolk-Citrate and Milk Extenders on Chromatin Structured Viability of Cryopreserved Bull Sperm", Journal of Dairy Science, Vol. 74, No. 11, 1999, pp 3836-3848.

Kilicarslan, M. R., Horoz, H., Senunver, S. C., Konuk, S. C., Tek, C. and Carioglu, B. 1996. Effect of GrnRH and hCG on ovulation and pregnancy in mares. Vet. Rec. 139: 119-120.

Lapin, D. R. and Ginther, O. J. 1977. Induction of ovulation and multiple ovulations in seasonally anovulatory and ovulatory mares with an equine pituitary extract. J. Anim. Sci. 44: 834-842.

Lawrenz, R. 1985. Preliminary results of non-surgical intrauterine insemination of sheep with thawed frozen semen. J S Afr. Vet. Assoc. 56(2): 61-63.

Levinson, G., et al., "DNA-based X-enriched sperm separation as an adjunct to preimplantation genetic testing for the preparation of X-linked disease", Mol. Human Reprod. 10: 979-982. (1995)

Lindsey, A., et al., "Hysteroscopic Insemination of Mares with Nonfrozen Low-dose Unsexed or Sex-sorted Spermatozoa", Currently unpublished, pp. 1-15.

Linge, F. "Faltforsok med djupfrost sperma (field trials with frozen sperm)", Farskotsel. 52: 12-13. (1972)

Lonergan, P., et al., "Effect of Time Interval from Insemination to First Cleavage on the Development of Bovine Embryos In Vitro and In Vivo", Theriogenology, 1999, p. 326

Long, C. R., et al, Theriogenology. 49(1): 363. abstr. (1998)

Loy, R. G. and Hughes, J. P. "The effects of human chorionic gonadotropin on ovulation, length of estrus, and fertility in the mare". Cornell Vet. 56: 41-50. (1965)

Lu, K. H., et al., "In Vitro Fertilization with Flow-Cytometrically-Sorted Bovine Sperm", Theriogenology 52, 1999, pp. 1393-1405.

Macmillan, K. L. and A. M. Day, "Prostaglandin F2a - A Fertility Drug In Dairy Cattle?", Ruakura Animal Research Station, Private Bag, Hamilton, New Zealand, Theriogenology, September 1982, Vol. 18 No. 3, pages 245-253

Matsuda, Y. and Tobari, I. "Chromosomal analysis in mouse eggs fertilized in vitro with sperm exposed to ultraviolet light (UV) and methyl and ethyl methanesulfonate (MMS and EMS)", Mutat. Res. 198: 131-144. (1988)

Maxwell, W. and Johnson, L., "Chlortetracycline Analysis of Boar Spermatozoa after Incubation, Flow Cytometric Sorting, Cooling, or Cryopreservation", Molecular Reproduction and Development 46, 1997, pp. 408-418.

Maxwell, W., et al., "Fertility of Superovulated Ewes after Intrauterine or Oviductal Insemination with Low Numbers of Fresh or Frozen-Thawed Spermatozoa", Reprod. Fertil. Dev. 5: 57-63. (1993)

McCue, P. M., et al., "Oviductal insemination in the mare", $7^{th}$ Int Symp. Eq. Reprod. 133. abstr. (1997)

McCue, P. M., "Superovulation", Vet. Clin. N. Amer. Eq. Prac. 12: 1-11. (1996)

McDonald, L. E., "Hormones of the pituitary gland", In: Veterinary Pharmacology and Therapeutics. $6^{th}$ ed., Ames, Iowa State Univ. Press. pp. 590. (1988)

McKenna, T., et al., "Nonreturn rates of dairy cattle following uterine body or cornual insemination", J. Dairy Sci. 73: 1179-1783. (1990)

McKinnon, A. and Voss, J., "Equine Reproduction" Lea & Febiger, Philadelphia, pp 291, 299-302, 345-348, 739-797. (1993)

McKinnon, A. et al, "Predictable ovulation in mares treated with an implant of the GnRH analogue deslorelin", Eq. Vet. J. 25: 321-323. (1993)

McKinnon, A. O. et al., "Repeated use of a GnRH analogue deslorelin (Ovuplant) for hastening ovulation in the transitional mare", Eq. Vet. J. 29: 153-155. (1996)

McNutt, T. L. and Johnson, L. A., "Flow cytometric sorting of sperm: influence on fertilization and embryo/fetal development in the rabbit", Mol. Reprod. Dev. 43: 261-267. (1996)

Meinert, C., et al., "Advancing the time of ovulation in the mare with a short-term implant releasing the GnRH analogue deslorelin", Equine Veterinary Journal, 25, 1993, pp 65-68.

Merton, J., et al., "Effect of Flow Cytometrically Sorted Frozen/Thawed Semen on Success Rate of In Vitro Bovine Embryo Production", Theriogenology 47, 1997, pp. 295.

Meyers, P. J., Bowman, T., Blodgett, G., Conboy, H. S., Gimenez, T., Reid, M. P., Taylor, B. C., Thayer, J., Jochle, W. and Trigg, T. E. 1997. Use of the GnRH analogue, deslorelin acetate, in a slow release implant to accelerate ovulation in oestrous mares. Vet. Rec. 140: 249-252.

Michaels, Charles, "Beef A.I. Facilities that work", Proc. Fifth N.A.A.B Tech. Conf. A.I. Reprod. Columbia, MO. pp. 20-22.

Michel, T. H., et al., "Efficacy of human chorionic gonadotrophin and gonadatrophin releasing hormone for hastening ovulation in Thoroughbred mares", Eq. Vet. J. 6: 438-442. (1986)

Miller, S. J., "Artificial Breeding Techniques in Sheep", In Morrow D.A. (ed): Current Therapy in Theriogenology 2 Philadelphia, WB Saunders. (1986)

Mirskaja, L. M. and Petrapavlovskii, V. V., "The reproduction of normal duration of heat in the mare by the administration of Prolan", Probl. Zivotn. Anim. Breed. Abstr. 5: 387. (1937)

Molinia, F. C., Gibson, R. J., Brown, A. M., Glazier, A. M. and Rodger, J. C. 1998. Successful fertilization after superovulation and laparoscopic intrauterine insemination of the brushtail possum, *Trichosurus vulpecula*, and tammar wallaby, *Macropus eugenii*. J. Reprod. Fert. 112: 9-17.

Morcom, C. B. and Dukelow, W. R. "A research technique for the oviductal insemination of pigs using laparoscopy", Lab. Anim. Sci. 1030-1031. (1980)

Morris, L. H., et al., "Hysteroscopic insemination of small numbers of spermatozoa at the uterotubal junction of preovulatory mares", Journal of Reproduction and Fertility, Vol. 118, pp. 95-100 (2000)

Mullet, W. and Gautier, F., "Interactions of heteroaromatic compounds with nucleic acids" Euro. J Biochem. 54: 358 (1975)

Munne, S., "Flow cytometry separation of X and Y spermatozoa could be detrimental to human embryos", Hum. Reprod. 9(5): 758, (1984)

Nowshari, et al., "Superovulation of Goats with Purified pFSH Supplemented with Defined Amounts of pLH", Theriogenology, Vol 43, pp 797-802 (1995)

Olson, S. E. and Seidel, G. E. Jr., "Reduced Oxygen Tension and EDTA improve Bovine Zygote Development in a Chemically Defined Medium", Journal of Animal Science 78, 2000, pp. 152-157.

Pace, M. M. and Sullivan, J. J., "Effect of timing of insemination, numbers of spermatozoa and extender components on pregnancy rates in mares inseminated with frozen stallion semen", J Reprod. Fert. Suppl. 23: 115-121 (1975)

Parrish, J. J., et al., "Capacitation of bovine sperm by heparin", Biology of Reproduction, Vol. 38, pp. 1171-1180 (1988)

PCT application PCT/US99/17165, filed 28 Jul. 1999, entitled "Equine System for Non-Surgical Artificial Insemination".

PCT application PCT/US98/27909, filed 31 Dec. 1998, entitled "Commercially Practical Sex-Specific Insemination of Mammals".

Peippo, J., et al., "Sex diagnosis of equine preimplantation embryos using the polymerase chain reaction", Theriogenology, Vol. 44 619-627 (1995)

-continued

Perry, E. J. "Historical Background In: The Artificial Insemination of Farm Animals", 4th ed. Edited by E. J. Perry. New Brunswick, Rutgers University Press, pp. 3-12., (1968)
Petersen, G. A., et al, "Cow and Calf Performance and Economic Considerations of Early Weaning of Fall-Born Beef Claves", J. Anim. Sci., 1987, 64: 15, pp 15-22.
Pickett, B. W, et al., "Factors influencing the fertility of stallion spermatozoa in an A.I. program", Proc. 8th Internat. Congr. Anim. Reprod. A.I. Krakow, Poland. 4: 1049-1052. (1976)
Pickett, B. W., and Shiner, K. A., "Recent developments in artificial insemination in horses", Livestock Production Science, 40, 1994, pp 31-36.
Pickett, B. W. and Back, D. G., "Procedures for preparation, collection, evaluation and insemination of stallion semen". C. S. U. Exp. Sta. Artira. Reprod. Lab. Gen. Series Bull. 935. (1973)
Pickett, B. W., et al., "Effect of seminal extenders on equine fertility", J. Anim. Sci. 40: 1136-1143. (1975)
Pickett, B. W., et al., "Influence of seminal additives and packaging systems on fertility of bovine spermatozoa", J. Anim. Sci. Suppl. II. 47: 12. (1978)
Pickett, G. W., et al., "Management of the mare for maximum reproductive efficiency" Bulletin No. 6 Colorado State University, Ft. Collins CO. (1989)
Pinkel, D., et al., "High resolution DNA measurements of mammalian spermatozoa". Cytometry. 3: 1-9. (1982)
Pinkel, D., et al, "Flow Cytometric Determination of the Proportions of X- and Y-Chromosome-Bearing Sperm in Samples of Purportedly Separated Bull Sperm", Journal of Animal Science, Vol. 60, No. 5, 1985, pp 1303-1307.
Polge, E. J., "Historical Perspective of AI: Commercial Methods of Producing Sex Specific Semen, IVF Procedures", Proceedings of the 16th Technical Conference on Artificial Insemination & Reproduction, Cambridge, England, 1996, pp. 7-11.
Preza, C. et al, "Determination of Direction-Independant Optical Path-Length Distribution of Cells Using Rotational-Diversity Transmitted-Light Differential Interference Contrast (DIC) Images", Presented at the Multidimensional Microscopy: Image Aquisition and Processing V, p. 1-11 (1998)
Rath, D., et al., "Production of Piglets Preselected for Sex Following in Vitro Fertilization with X and Y Chromosome-Bearing Spermatozoa Sorted by Flow Cytometry", Theriogenology, 47, 1997, pp 795-800.
Rath, D., et al., "Low Dose Insemination Technique in the Pig", Boar Semen Preservation IV, 2000, pp. 115-118.
Reiling, B. A., et al., "Effect of Prenatal Androgenization on Preformance, Location, and Carcass and Sensory Traits on Heifers in Single Calf Heifer System", J. Anim. Sci., 1995, 73: pp 986-992.
Rens, W., et al., "Improved Flow Cytometric Sorting of X- and Y-Chromosome Bearing Sperm: Substantial Increase in Yield of Sexed Semen", Molecular Reproduction and Development, 1999, pp 50-56.
Rens, W., et al., "A Novel Nozzle for More Efficient Sperm Orientation to Improve Sorting Efficiency of X and Y Chromosome-Bearing Sperm", Technical Notes, Cytometry 33, 1998, pp 476-481.
Rieger, D., et al, "The Relationship Between the Time of First Cleavage of Fertilized Cattle Oocytes and Their Development to the Blastocyst Stage", Theriogenology, 1999, pp. 190.
Ritar, A. and Ball, A. "Fertility of young cashmere goats after laparoscopic insemination". J. Agr. Sci. 117: 271-273. (1991)
Roberts, J. R. In: Veterinary Obstetrics and Genital Diseases. Ithaca, New York. pp. 740-749. (1971)
Roser, J F., et al., "Reproductive efficiency in mares with anti-hCG antibodies", Proc 9th Int. Congr. Artira. Repro. and A.I. 4: 627. abstr. (1980)
Roth, T. L., et al., "Effects of equine chorionic gonadotropin, human chorionic gonadotropin, and laparoscopic artificial insemination on embryo, endocrine, and luteal characteristics in the domestic cat", Bio Reprod. 57: 165-171. (1997)
Rowley, H-S., et al., "Effect of insemination volume on embryo recover}' in mares", J. Equine Vet. Sci. 10: 298-300. (1990)
Salamon, S. "Artificial Insemination of Sheep". Chippendale, New South Whales. Publicity Press. p. 83-84. (1976)
Salisbury, G. W. and VanDemark, N. L. "Physiology of Reproduction and Artificial Insemination of Cattle", San Francisco: Freeman and Company. (1961)
SAS, SAS/STAT ® User's Guide (Release 6.03), SAS Inst. Inc., Cary, NC., 1988. 3 pages
Schenk, J. L. and Seidel, Jr., G. E., "Imminent Commercialization of Sexed Bovine", Proceedings, The Range Beef Cow Symposium XVL, 1999, pp 89-96.
Schenk, J. L., et al., "Cryopreservation of Flow-Sorted Bovine Spermatozoa", Theriogenology 52, 1999, pp. 1375-1391.
Schmid R. L., et al, Fertilization with Sexed Equine Spermatozoa Using Intracytoplasmic Sperm Injection and Oviductal Insemination", 7th International Symposium On Equine Reproduction, pp. 139 (Abstract) (1998)
Seidel, G. Jr., "Use of Sexed Bovine Sperm for In Vitro Fertilization and Superovulation", Animal Reproduction and Biotechnology Laboratory, Colorado State University, Proceedings of the 2000 CETA/ACTE Convention, Charlottetown, Prince Edward Island, August 2000, pp. 22-24.
Seidel, G. E. and Johnson, L. A., "Sexing Mammalian Sperm - Overview", Theriogenology 52: 1267-1272, (1999)
Seidel, G. E. Jr, et al., "Insemination of Heifers with Sexed Sperm ", Theriogenology, Vol. 52, pp. 1407-1421 (1999)
Seidel, G. E. Jr, et al., "Artificial Insemination of Heifers with Cooled, Unfrozen Sexed Semen", Theriogenology, Vol. 49 pp. 365 (Abstract) (1998)
Seidel, G. E. Jr., et al, "Insemination of heifers with sexed frozen or sexed liquid semen", Theriogenology. 51. (in press). abstr. (1999)
Seidel, G. E., Jr., et al, "Uterine Horn Insemination of Heifers With Very Low Numbers of Nonfrozen and Sexed Spermatozoa,", Animal Reproduction and Biotechnology Laboratory Colorado State University, Atlantic Breeders Cooperative, Theriogenology (1997), pp. 1255-1264
Seidel, G. E., "Status of Sexing Semen for Beef Cattle", Texas A&M University 45th Annual Beef Cattle Short Course and Trade Show Proceedings, Aug. 9-11, 1999; pp. III 24-III 27
Seidel, Jr., G. E., "Artificial Insemination With X- and Y-Bearing Bovine Sperm", Animal Reproduction and Biotechnology Laboratory, Colorado State University, (1996)
Seidel, Jr., G. E., et al, "Insemination of Holstein Heifers With Very Low Numbers Of Unfrozen Spermatozoa", Colorado State University, Atlantic Breeders Cooperative, (1995)
Senger, P. L., et al., "Influence of cornual insemination on conception rates in dairy cattle". J Anim. Sci. 66: 3010-3016. (1988)
Shelton, J. N. and Moore, N. W. 1967. The response of the ewe tot pregnant mare gonadotropin and to horse anterior pituitary extract. J. Reprod. Fert. 14: 175-177.
Shilova, A. V., Platov, E. M. and Lebedev, S. G. 1976. The use of human chorionic gonadothrophin for ovulation date regulation in mares. VIIIth Int. Congr. On Anim. Repro. and A.I. 204-208.
Squires, E., "Simultaneous Analysis of Multiple Sperm Attributes by Flow Cytometry", Diagnostic Techniques and Assisted Reproductive Technology, The Veterinary Clinics of North America, Equine Practice, Vol. 12, No. 1, April -continued 1996, pp127-130.

Squires, E. L, et al., "Effect of dose of GnRH analogue on ovulation in mares", Theriogenology. 41: 757-769. (1994)

Squires, E. L., "Early Embryonic Loss" in Equine Diagnostic Ultrasonography, 1st Ed. pp 157-163 Eds Rantanen & McKinnon. Williams and Wilkins, Baltimore, Maryland (1998)

Squires, E. L., et al, "Cooled and frozen stallion semen", Bulletin No. 9, Colorado State University, Ft. Collins, CO. (1999)

Sullivan, J. J., Parker, W. G. and Larson, LL. 1973. Duration of estrus and ovulation time in nonlactating mares given human chorionic gonadotropin during three successive estrous periods. J. A. V. M. A. 162: 895-898.

Sumner, A. T. and Robinson, J. A., "A Difference in Dry mass between the heads of X and Y-bearing human Spermatozoa", J Reprod Fert 48, p. 9-15 (1976)

Taljaard, T. L., Terblanche, S. J., Bertschinger, H. J. and Van Vuuren, L. J. 1991. The effect of the laparoscopic insemination technique on the oestrus cycle of the ewe. J. S Afr. Vet. Assoc. 62(2): 60-61.

Taylor, C. S., "Efficiency of Food Utilization in Traditional and Sex-Controlled Systems of Beef Production", AFRC Animal Breeding Research Organization, West Mains Road, Edinburg EH9 3JQ, pp 401-440.

Tervit, H. R., et al., "Successful Culture In Vitro of Sheep and Cattle Ova", Agricultural Research Council, Unit of Reproduction Physiology and Biochemistry, University of Cambridge, 1972, p. 493-497.

U.S. application Ser. No. 09/015,454 filed Jan. 29, 1998, entitled "System for Improving Yield of Sexed Embryos in Mammals".

U.S. application Ser. No. 09/001,394, filed Dec. 31, 1997, entitled "Sheath Fluids and Collection Systems for Sex-Specific Cytometer Sorting of Sperm".

U.S. application Ser. No. 09/454,488, entitled "Improved Flow Cytometer Nozzle and Flow Cytometer Sample Handling Methods", filed Dec. 3, 1999.

U.S. application Ser. No. 09/448,643, entiled "Multiple Sexed Embryo Production System for Mammals", filed Nov. 24, 1999.

U.S. application Ser. No. 09/511,959 entitled "Methods For Improving Sheath Fluids and Collection Systems For Sex-Specific Cytometer Sorting of Sperm", filed Feb. 23, 2001.

U.S. Appl. No. 60/094,720, entitled "System for Low Dose Insemination of Equines", filed Jul. 30, 1998.

U.S. Appl. No. 60/224,050., entitled "Integrated System for Herd Management With Terminal-Cross Program Using Sexed Semen", filed Aug. 9, 2000.

U.S. Appl. No. 60/113,143, entitled "Equine Insemination System", filed Dec. 18, 1998.

U.S. Appl. No. 60/203,089, entitled "Detector System for Resolving Small Differences in Photo-generated Signal", filed May 9, 2000.

U.S. Appl. No. 60/238,294, entitled "Hysteroscopic Insemination of Mares" filed Oct. 5, 2000.

U.S. Appl. No. entitled "System For Separating Frozen-Thawed Sperm Cells Into X-Chromosome And Y-Chromosome Bearing Populations", filed Nov. 28, 2000.

U.S. Appl. No. entitled "A System for In-vitro Fertilization with Spermatozoa Separated into X-chromosome and Y-chromosome Bearing Populations", filed Nov. 28, 2000.

Van Munster E. B., et al, "Measurement-based evaluation of optical pathlength distributions reconstructed from simulated differential interference contrast images", Journal of Microscopy 192, Pt. 2, p. 170-176 (1998)

Van Munster, E. B., et al, "Difference in Sperm Head Volume as a Theoretical Basis for Sorting X & Y-Bearing Spermatozoa: Potentials and Limitations", Theriogenology 52, pp. 1281-1293, (1999)

Van Munster, E. B., et al, "Reconstruction of optical pathlength distributions form images obtained by a wide field differential interference contrast microscope", Journal of Microscopy 188, Pt. 2, p. 149-157 (1997)

Van Munster, E. B., "Geslachtsbepaling met interferometrie", Derde prijs NtvN-prijsvraag voor pas-gepromoveerden 65/4, p. 95-98 (1999)

Van Munster E. B., et al, "Difference in Volume of X- and Y-chromosome Bearing Bovine Sperm Heads Matches Difference in DNA Content" Cytometry 35 p. 125-128 (1999)

Vazquez, J., et al., "A.I. in Swine; New Strategy for Deep Insemination with Low Number of Spermatozoa Using a Non-surgical Methodology", 14th International Congress on Animal Reproduction, Vol. 2, Stockhlom, July, 2000, p. 289.

Vazquez, J., et al., "Development of a Non-surgical Deep Intra Uterine Insemination Technique", IV International Conference on Boar Semen Preservation, Maryland, August, 1999, p 35 and photo of display board.

Vazquez, J., et al., "Successful Low-Dose Insemination by a Fiberoptic Endoscope Technique in the Sow", Proceedings Annual Conference of the International Embryo Transfer Society, Netherlands, Theriogenology, Vol. 53, January, 2000, pp. 201.

Vazquez, J., et al., "Hyposematic Swelling Test as Predictor of the Membrane Integrity in Boar Spermatozoa", Boar Semen Preservation IV, IVth International Conference on Boar Semen Preservation, Maryland, pp. 263.

Vazquez, J. et al., "Nonsurgical Uterotubal Insemination in the Mare", Proceedings of the 44th Annual Convention of the American Association of Equine Practitioners, Baltimore, Maryland, Dec. 6-9, 1998, Vol. 44, pp 68-69

Vidament, M., Dupere, A. M., Julienne, P., Evain, A., Noue, P. and Palmer, E. 1997. Equine frozen semen freezeability and fertility field results. Theriogenology. 48: 907.

Voss, J. L. et al., "Reproductive management of the broodmare". C. S. U. Exp. Sta. Anim. Reprod. Lab. Gen. Series. Bull. 961. (1976)

Voss, J. L., et al., "Effect of number and frequency of inseminations on fertility in mares", J. Reprod. Fertil. Suppl. 32: 53-57. (1982)

Voss, J. L., "Effect of human chorionic gonadotropin on duration of estrous cycle and fertility of normally cycling, non-lactating mares". J. A. V. M. A. 165: 704-706. (1974)

Welch, G., et al., "Flow Cytometric Sperm Sorting and PCR to Confirm Separation of X- and Y-Chromosome Bearing Bovine Sperm", Animal Biotechnology, 6 (2), 131-139, 1995, pp 131-139.

Welch G. R., et al., "Fluidic and optical modifications to a FACS IV for flow sorting of X- and Y-chromosome bearing sperm based on DNA", Cytometry 17 (suppl. 7): 74. (1994)

Wilson, C. G., et al., "Effects of repeated hCG injections on reproductive efficiency in mares", Eq. Vet. Sci. 4: 301-308. (1990)

Wilson, M. S., "Non-surgical intrauterine artificial insemination in bitches using frozen semen", J. Reprod. Fert Suppl. 47: 307-311. (1993)

Windsor, D. P., et al, "Sex Predetermination by Seperation of X and Y Chromosome-bearing Sperm: A Review", Reproduction of Fertilization and Developement 5, pp. 155-171, (1993)

Woods, J. and Ginther, O. J., "Recent studies related to the collection of multiple embryos in mares". Theriogenology. 19: 101-108. (1983)

Woods, J., et al., "Effects of time of insemination relative to ovulation on pregnancy rate and embryonic-loss rate in mares". Eq. Vet. J. 22(6): 410-415. (1990)
XP-002103478, File Biosis, (1988), one page In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

Thus, the applicant(s) should be understood to have support to claim at least: I) each of the liquid to gas conversion devices described herein, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and the x) the various combinations and permutations of each of the elements disclosed In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

The claims set forth in this specification by are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of isolating X-chromosome bearing sperm cells and Y-chromosome bearing sperm cells, comprising the steps of:
   collecting viable sperm cells from a male of a species of non-human mammal;
   staining said viable sperm cells to produce viable, stained sperm cells;
   differentiating between X-chromosome bearing sperm cells and Y-chromosome bearing sperm cells based upon fluorescent light emitted from said viable, stained sperm cells
   which is detected with a photomultiplier tube operating at below 400 volts;
   separating said X-chromosome bearing sperm cells and Y-chromosome bearing sperm cells into a X-chromosome bearing population and a Y-chromosome bearing population at a separation rate between 4,000 to 10,000 separations per second of each sex;
   and producing separate X-chromosome bearing and Y-chromosome bearing populations of sperm cells each having a purity of greater than 90%.

2. A method of isolating X-chromosome bearing sperm cells and Y-chromosome bearing sperm cells as described in claim 1, wherein said step of differentiating between X-chromosome bearing sperm cells and Y-chromosome bearing sperm cells of said viable, stained sperm cells comprises measuring an amount of DNA within a nucleus of said sperm cells.

3. A method of isolating X-chromosome bearing sperm cells and Y-chromosome bearing sperm cells as described in claim 2, wherein said step of measuring an amount of DNA within a nucleus of said sperm cells comprises the steps of:
   a. generating a beam of electromagnetic radiation having initial wave form characteristics;
   b. traversing said sperm cell containing said amount of DNA with said beam of electromagnetic radiation;
   c. altering said initial wave form characteristics by traversing said sperm cell; and
   d. analyzing altered wave form characteristics.

4. A method of isolating X-chromosome bearing sperm cells and Y-chromosome bearing sperm cells as described in claim 3, wherein said step of altering said initial wave form characteristics by traversing said sperm cell comprises the step of shifting phase of said initial wave form of said beam of electromagnetic radiation.

5. A method of isolating X-chromosome bearing sperm cells and Y-chromosome bearing sperm cells as described in claim 4, further comprising the step of superimposing said beam of electromagnetic radiation having shifted phase on said beam of electromagnetic radiation having said initial wave form characteristics.

6. A method of isolating X-chromosome bearing sperm cells and Y-chromosome bearing sperm cells as described in claim 5, further comprising the step of comparing electromagnetic radiation intensity of superimposed beams of electromagnetic radiation with intensity of said beam of electromagnetic radiation having initial wave form characteristics.

7. A method of isolating X-chromosome bearing sperm cells and Y-chromosome bearing sperm cells as described in claim 6, further comprising the step of determining said amount of DNA based upon a difference in said light intensity between said superimposed beams of electromagnetic radiation and said beam of electromagnetic radiation having initial waveform characteristics.

8. A method of isolating X-chromosome bearing sperm cells and Y-chromosome bearing sperm cells as described in claim 2, further comprising the steps of:
   a. introducing said sperm cells into a fluid stream;
   b. analyzing said sperm cells entrained in said fluid stream;
   c. forming a plurality of droplets having one of said sperm cells entrained;
   d. charging each of said droplets differentially based upon said detected fluorescent light of said sperm cells entrained in said droplets;
   e. deflecting each of said droplets; and
   f. differentially collecting each population of said sperm cells entrained in said droplets.

9. A method of isolating X-chromosome bearing sperm cells and Y-chromosome bearing sperm cells as described in claim 1, further comprising the step of irradiating said stained sperm cells.

10. A method of isolating X-chromosome bearing sperm cells and Y-chromosome bearing sperm cells as described in claim 9, wherein said step of irradiating said stained sperm cells comprises generating an irradiation beam pattern having a height about equal to the length of said sperm cells along the longitudinal axis to about three times the length of said sperm cells along the longitudinal axis.

11. A method of isolating X-chromosome bearing sperm cells and Y-chromosome bearing sperm cells as described in claim 10, wherein said sperm cell has a longitudinal axis of about nine micrometers in length, and said height of said irradiation beam pattern is about 20 micrometers.

12. A method of isolating X-chromosome bearing sperm cells and Y-chromosome bearing sperm cells as described in claim 8, wherein said step of forming droplets comprises forming droplets having sufficient size to encapsulate said sperm cell.

13. A method of isolating X-chromosome bearing sperm cells and Y-chromosome bearing sperm cells as described in claim 12, further comprising the step of ejecting said fluid stream from a nozzle having an orifice, wherein said orifice has a diameter of 70 micrometers.

14. A method of isolating X-chromosome bearing sperm cells and Y-chromosome bearing sperm cells as described in claim 13, further comprising the steps of:
   a. orienting said sperm cells with respect to a detector;
   b. detecting light having characteristics differentially responsive to sperm cell orientation to said detector;
   c. converting said light having characteristics deferentially responsive to said sperm cell orientation into at least one signal containing sperm cell orientation information; and
   d. determining orientation of said sperm cell with respect to said detector.

15. A method of isolating X-chromosome bearing sperm cells and Y-chromosome bearing sperm cells as described in claim 14, further comprising the step of differentially collecting said droplets based upon determined orientation of said sperm cell with respect to said detector.

16. A method of isolating X-chromosome bearing sperm cells and Y-chromosome bearing sperm cells as described in claims 1, 3, 12, or 14, wherein said purity of said X-chromosome bearing and said Y-chromosome bearing populations of sperm cells is selected from the group consisting of between 90% to about 100%, between about 91% to about 100%, between about 92% to about 100%, between about 93% to about 100%, between about 94% to about 100%, between about 95% to about 100%, between about 96% to about 100%, between about 97% to about 100%, between about 98% to about 100%, and between about 99% to about 100%.

17. A method of isolating X-chromosome bearing sperm cells and Y-chromosome bearing sperm cells as described in claims 1, 3, 12, or 14, further comprising the step of establishing a separable event rate up to about 35,000 separable events per second.

18. A method of isolating X-chromosome bearing sperm cells and Y-chromosome bearing sperm cells as described in claim 12 or 14 wherein said step of forming droplets each having one of said sperm cells entrained comprises a droplet formation rate up to about 200,000 droplets per second.

19. A method of isolating X-chromosome bearing sperm cells and Y-chromosome bearing sperm cells as described in claim 1, wherein said species of mammal comprises a bovine mammal.

20. A method of isolating X-chromosome bearing sperm cells and Y-chromosome bearing sperm cells as described in claim 1, wherein said species of mammal comprises an equine mammal.

21. A method of isolating X-chromosome bearing sperm cells and Y-chromosome bearing sperm cells as described in claim 1, wherein said species of mammal comprises an ovine mammal.

22. A method of isolating X-chromosome bearing sperm cells and Y-chromosome bearing sperm cells as described in claim 1, further comprising the step of operating said photomultiplier tube at a voltage selected from a group consisting of about 280 volts, about 200 volts, just above 0 volts, and below 300 volts.

* * * * *